(12) United States Patent
Stern et al.

(10) Patent No.: US 10,982,254 B2
(45) Date of Patent: *Apr. 20, 2021

(54) METHODS FOR RAPID ANTIMICROBIAL SUSCEPTIBILITY TESTING

(71) Applicant: SeLux Diagnostics, Inc., Charlestown, MA (US)

(72) Inventors: Eric Stern, Charlestown, MA (US); Aleksandar Vacic, Charlestown, MA (US); Benjamin Spears, Charlestown, MA (US); Alec Flyer, Charlestown, MA (US); Kelly Flentie, Charlestown, MA (US)

(73) Assignee: SeLux Diagnostics, Inc., Charlestown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/685,737

(22) Filed: Nov. 15, 2019

(65) Prior Publication Data

US 2020/0080128 A1     Mar. 12, 2020

Related U.S. Application Data

(63) Continuation of application No. 15/717,569, filed on Sep. 27, 2017, now Pat. No. 10,501,772, which is a continuation of application No. 15/464,240, filed on Mar. 20, 2017, now Pat. No. 9,834,808, which is a continuation of application No. PCT/US2017/014343, filed on Jan. 20, 2017.

(60) Provisional application No. 62/383,198, filed on Sep. 2, 2016, provisional application No. 62/370,579, filed on Aug. 3, 2016, provisional application No. 62/338,376, filed on May 18, 2016, provisional application No. 62/326,545, filed on Apr. 22, 2016, provisional application No. 62/298,821, filed on Feb. 23, 2016, provisional application No. 62/281,698, filed on Jan. 21, 2016.

(51) Int. Cl.
*C12Q 1/18* (2006.01)
*C12Q 1/02* (2006.01)

(52) U.S. Cl.
CPC .............. *C12Q 1/18* (2013.01); *C12Q 1/025* (2013.01); *G01N 2333/195* (2013.01); *G01N 2458/00* (2013.01); *G01N 2500/10* (2013.01)

(58) Field of Classification Search
CPC .................................................. G01N 2500/10
See application file for complete search history.

(56) References Cited

FOREIGN PATENT DOCUMENTS

| JP | 2007526245 A | 9/2007 | |
|----|--------------|--------|---|
| JP | 2012525574 A | 10/2012 | |
| JP | 2014523914 A | 9/2014 | |
| WO | WO 2006066216 A2 * | 6/2006 | ....... G01N 33/54366 |

OTHER PUBLICATIONS

Mukkala, V.-M., et al., The Synthesis and Use of Activated N-Benzyl Derivatives of Diethylenetriaminetetraacetic Acids: Alternative Reagents for Labeling of Antibodies with Metal Ions, Analytical Biochemistry 176:319-325 (1989).

Knall, A-C., et al., Polynorbornenes With Pendant Europium (III) Coordination Compounds, Macromolecular Chemistry and Physics, 213:2618-2627 (2012).

Bian, Z., et al., Syntheses of new amphiphilic europium(III) complexes for Langmuir-Blodgett films, Colloids and Surfaces A: Physicochem Eng Aspects 257-258 (2005).

Means, G.E., and Feeney, R.E., Chemical Modifications of Proteins: History and Applications 1:2-12 (1990).

* cited by examiner

*Primary Examiner* — Bin Shen
(74) *Attorney, Agent, or Firm* — Kacvinsky Daisak Bluni PLLC

(57) ABSTRACT

The present invention relates, in part, to methods and kits for rapidly determining antimicrobial susceptibility of microorganisms.

22 Claims, 49 Drawing Sheets

| Species/antimicrobial | Strain type (ATCC) | MIC (μg/ml): Fast-AST | MIC (μg/ml): $OD_{600}$ |
|---|---|---|---|
| *Staphylococcus aureus*/ methicillin | Susceptible (29213) | 2 | 2 |
| | Resistant (43300) | 4 | 4 |
| *Pseudomonas aeruginosa*/ imipenem | Susceptible (27853) | 2 | 4 |
| | Resistant (BAA-2108) | 32 | 32 |
| *Escherichia coli*/ ampicillin | Susceptible (25922) | 4 | 4 |
| | Resistant (35218) | 32 | 32 |

FIG. 8

| | E. coli | S. aureus | P. aeruginosa | K. pneumoniae | E. faecalis | S. epidermidis |
|---|---|---|---|---|---|---|
| Antibody/WGA-HRP conjugate | Abcam ab68450 | Fitzgerald 60C-CR1274RX | Abcam ab156654 | Thermo PA1-73176 | Thermo PA1-73122 | Vector Labs PL-1026 (WGA-HRP) |
| Drug | Ampicillin | Oxacillin | Ampicillin | Ampicillin | Oxacillin | Oxacillin |
| Strains | ATCC 25922, 35218, BAA-2340, 52 Clinical isolates | ATCC 29213, 43300, 13565, 7660, 12 Clinical isolates | ATCC 27853, BAA-2108, 4 Clinical isolates | ATCC 700603, BAA-1705, 4 Clinical isolates | ATCC 29212, 51299, 2 Clinical isolates | 4 Clinical isolates |

| a Antibiotic | FAST | Reference |
|---|---|---|
| Chloramphen | 2 | S (1) |
| Daptomycin | 2 | S (1) |
| Clindamycin | ≤0.25 | S (≤0.25) |
| Gentamycin | ≥8 | I (6) |
| Levofloxacin | ≥4 | R (4) |
| DT1 | Neg | Neg |
| Linezolid | ≤1 | S (1) |
| Vancomycin | 4 | I (3) |
| Cefoxitin screen | Pos | Pos |
| Penicillin | ≥2 | R (≥0.5) |
| Moxifloxacin | ≥8 | R (2) |
| Oxacillin | ≥2 | R (≥4) |
| Rifampin | ≥2 | R (≥32) |
| Tigecycline | ≤0.25 | S (≤0.25) |
| Nitrofurantoin | - | S (≤16) |
| Erythromycin | 2 | S (≤0.25) |
| Tetracycline | ≥8 | R (≥16) |
| Ciprofloxacin | ≥4 | R (≥8) |

| b Antibiotic | FAST | Reference |
|---|---|---|
| Amikacin | 8 | S |
| Tigecycline | ≤0.5 | S |
| Ticarcillin/Clauv | ≥64/2 | R |
| Levofloaxin | ≥8 | R |
| Tetracycline | ≥4 | S |
| Doripenem | 2 | R |
| Minocycline | 4 | S |
| Ertapenem | ≥8 | R |
| Trimetho/Sulf | ≥4/76 | R |
| Imipenem | 2 | R |
| Piperacillin | ≥64 | R |
| Meropenem | ≥8 | R |
| Gentamycin | ≥8 | R |
| Cefazolin | ≥16 | R |
| Tobramycin | ≥8 | R |
| Ceftazidime | ≥16 | R |
| Amp/Sulbac | ≥16/8 | R |
| Aztreonam | ≥32 | R |
| Ampicillin | ≥16 | R |
| Cefepime | ≥32 | R |
| Ciprofloxacin | ≥2 | R |
| Ceftriaxone | ≥32 | R |

FIG. 12B

| c Error/Discrepancy | Description |
|---|---|
| Very major (vmj) | CLSI method gives R and FAST gives S |
| Major | CLSI method gives S and FAST gives R |
| Minor | CLSI gives R or S and FAST gives I; or CLSI gives I and FAST R or S |

Drug: Levofloxacin

| | Reference Results (CLSI O/N) | | | | | | |
|---|---|---|---|---|---|---|---|
| SeLux Results (4 hr) | ≤0.25 | 0.5 | 1 | 2 | 4 | 8 | ≥16 |
| ≤0.25 | 1 | | | | | | |
| 0.5 | 1 | | | | | | |
| 1 | | | | | | | |
| 2 | | | | | | | |
| 4 | | | | | 4 | 1 | |
| 8 | | | | | | 1 | |
| ≥16 | | | | | | | |
| | | 0 | 0 | 0 | 4 | 2 | |
| EA | 100 | | | | | | |
| CA | 100 | | | | | | |

FIG. 13C

Drug: Ampicillin

| SeLux Results (4 hr) \ Reference Results (CLSI O/N) | ≤0.5 | 1 | 2 | 4 | 8 | 16 | ≥32 |
|---|---|---|---|---|---|---|---|
| ≤0.5 | 2 | 2 | | | | | |
| 1 | 1 | 4 | 3 | | | | |
| 2 | | | 1 | 1 | | | |
| 4 | | | 1 | 2 | 1 | | |
| 8 | | | | | | | |
| 16 | | | | | | 1 | 1 |
| ≥32 | | | | | | | 12 |
| | | 4 | 5 | 3 | 1 | 1 | |
| EA | 100 | | | | | | |
| CA | 100 | | | | | | |

FIG. 14A

Drug: Ciprofloxacin

| SeLux Results (4 hr) \ Reference Results (CLSI O/N) | ≤0.25 | 0.5 | 1 | 2 | 4 | 8 | ≥16 |
|---|---|---|---|---|---|---|---|
| ≤0.25 | | | | | | | |
| 0.5 | | | | | | | |
| 1 | | | | | | | |
| 2 | | | 1 | 1 | | | |
| 4 | | | | | | | |
| 8 | | | | | | | |
| ≥16 | | | | | | | |
| | | | 0 | 1 | 1 | 0 | 0 |
| EA | 100 | | | | | | |
| CA | 100 | | | | | | |

METHODS FOR RAPID ANTIMICROBIAL SUSCEPTIBILITY TESTING

RELATED APPLICATIONS

This application is a continuation of U.S. application Ser. No. 15/717,569, filed Sep. 27, 2017, which is a continuation of U.S. application Ser. No. 15/464,240, filed Mar. 20, 2017, which is a continuation of International Patent Application No. PCT/US17/14343, filed Jan. 20, 2017. PCT/US17/14343 designates the United States and claims priority to and benefit of U.S. Provisional Patent Application No. 62/281,698, filed Jan. 21, 2016; U.S. Provisional Patent Application No. 62/298,821, filed Feb. 23, 2016; U.S. Provisional Patent Application No. 62/326,545, filed Apr. 22, 2016; U.S. Provisional Patent Application No. 62/338,376, filed May 18, 2016; U.S. Provisional Patent Application No. 62/370,579, filed Aug. 3, 2016; and U.S. Provisional Patent Application No. 62/383,198, filed Sep. 2, 2016. The contents of the aforementioned patent applications are incorporated herein by reference in their entireties.

BACKGROUND OF THE INVENTION

Antimicrobial-resistant microbial infections are associated with poor clinical outcomes including increased morbidity, mortality, and healthcare costs among infected patients. The prevalence of these organisms in such facilities in the United States has steadily increased over the last 30 years. Phenotypic antimicrobial susceptibility testing (AST) of microorganisms is critical for informing physicians of appropriate therapeutic regimens. Using current methods, AST determination typically requires a minimum of eight hours, rendering it an overnight process due to shift work in many clinical microbiology laboratories. While awaiting a determination from current AST methods, patients are often administered broad-spectrum antimicrobials which often have significant detrimental effects on patient health and/or contribute to the growing antimicrobial resistance epidemic. Furthermore, this time delay to getting accurate antimicrobial treatment information increases patient stays in hospitals, thereby increasing costs and inconvenience to the patient.

Accordingly, a need exists for a method that rapidly determines antimicrobial susceptibility of a microbial infection. The method described here is further advantageous in that it addresses this need in a cost-effective manner because it is compatible with existing assay hardware components.

SUMMARY OF THE INVENTION

The present invention permits rapid determination of antibiotic susceptibility of microbial infections. The invention is based in part upon the surprising discovery of non-specific surface binding assays that provide accurate and rapid Antimicrobial Susceptibility Testing (AST) determinations in fewer than twelve hours—and, specifically, under four hours. The present invention ("Fast-AST") provides accurate results that are consistent with results obtained using the Clinical Laboratory Standards Institute (CLSI) reference methods when tested with multiple antimicrobials and on a plurality of microorganisms; however, the present invention takes significantly less time to obtain results than the CLSI methods. Moreover, the present invention accurately differentiates an antimicrobial's MIC for clinically-relevant microbial strains that are resistant to one or more antimicrobials and the antimicrobial's MIC for strains of the same microorganism that are sensitive to the antimicrobials. Furthermore, the present invention may include signaling agents (e.g., Europium compounds) that are bound to microorganisms non-specifically rather than specifically (e.g., via chemically conserved groups or biochemically conserved binding sites on microorganisms), thereby expanding the generalization of the present invention to any microorganism and allowing onset of an appropriate treatment without first needing to identify the particular infectious microorganism. Also, the present invention permits signal amplification such that microbes may be rapidly detected at lower concentrations, e.g., from a dilute culture of microorganisms or via a patient's biological sample. Additionally, the present invention may use Europium formulations as chemical moiety, thereby expanding the dynamic range of the methods and allowing for more accurate determinations from a range of microbial samples. Finally, the present invention is compatible with existing equipment, thereby enabling rapid adoption in current clinical laboratories. Accordingly, the present invention, in a greatly reduced amount of time and expense, relative to standard methods, can provide a patient with an appropriate treatment regimen, i.e., a specific antimicrobial and at a particular dosage. Thus, the present invention will improve patient outcomes, lower hospital costs, and help reduce further evolution of antimicrobial resistant microorganisms; thus, the present invention represents a significant breakthrough in the AST field.

An aspect of the present invention is a method for determining antimicrobial susceptibility of microorganisms. The method includes steps of incubating a liquid suspension of microorganisms in the presence of an antimicrobial and a signaling agent, which is capable of binding to a surface of the microorganisms, under conditions that promote growth of the microorganisms; separating the microorganisms bound by the signaling agent from the unbound signaling agent; and determining signal levels associated with the microorganisms as compared to one or more controls.

Another aspect of the present invention is a method for determining antimicrobial susceptibility of microorganisms. The method includes steps of incubating a liquid suspension of microorganisms in the presence of an antimicrobial under conditions that promote growth of the microorganisms; adding a signaling agent capable of binding to a surface of the microorganisms; separating the microorganisms bound by the signaling agent from the unbound signaling agent; and determining signal levels associated with the microorganisms as compared to one or more controls.

Yet another aspect of the present invention is a method for determining antimicrobial susceptibility of microorganisms. The method includes steps of incubating a liquid suspension of microorganisms in a cartridge including a plurality of chambers, each chamber containing one or more antimicrobials, under conditions that promote growth of the microorganisms; adding a signaling agent, which is capable of binding to a surface of the microorganisms, to the plurality of chambers; removing unbound signaling agent; and determining signaling levels in the plurality of chambers as compared to one or more controls.

An aspect of the present invention is a method for determining antimicrobial susceptibility of microorganisms. The method includes incubating microorganisms in the presence of an antimicrobial and a signaling agent, which includes a signal amplifier and one or more chemical moieties capable of binding non-specifically to a surface of the microorganisms, under conditions that promote growth of the microorganisms; separating the microorganisms bound by the signaling agent from the unbound signaling agent; and determining signal levels associated with the microorganisms as compared to one or more controls.

Another aspect of the present invention is a method for determining antimicrobial susceptibility of microorganisms. The method includes incubating microorganisms in the presence of an antimicrobial under conditions that promote growth of the microorganisms; adding a signaling agent including a signal amplifier and one or more chemical moieties capable of binding non-specifically to a surface of the microorganisms; separating the microorganisms bound by the signaling agent from the unbound signaling agent; and determining signal levels associated with the microorganisms as compared to one or more controls.

Yet another aspect of the present invention is a kit for determining antimicrobial susceptibility of microorganisms. The kit includes a signaling agent capable of binding to a surface of the intact microorganisms of interest; a solution for incubating a sample containing microorganisms; and one or more reagents for generating signals from the signaling agent.

Any aspect or embodiment described herein can be combined with any other aspect or embodiment as disclosed herein. While the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

Other features and advantages of the invention will be apparent from the Drawings and the following detailed description and claims.

BRIEF DESCRIPTION OF THE DRAWINGS

The above and further features will be more clearly appreciated from the following detailed description when taken in conjunction with the accompanying drawings. The drawings however are for illustration purposes only; not for limitation.

FIG. 8 is a table summarizing data from Example 2. It compares MIC calls by the "fast-AST" technique with those of the standard overnight $OD_{600}$ procedure. The data shown represents the average of four wells, with values for each assay type relative to an antimicrobial-free control.

FIG. 11 is a table identifying the bacteria, antimicrobials, and the signaling agent/chemical moiety used in Example 4.

FIG. 12A to FIG. 12C are tables showing representative SensiTitre® results for *S. aureus* (FIG. 12A) and *K. pneumonia* (FIG. 12B). Data is not presented using the present invention for the nitrofurantonin *S. aureus* experiment because only two wells were dedicated to this antimicrobial.

Figures 13A, 13B:
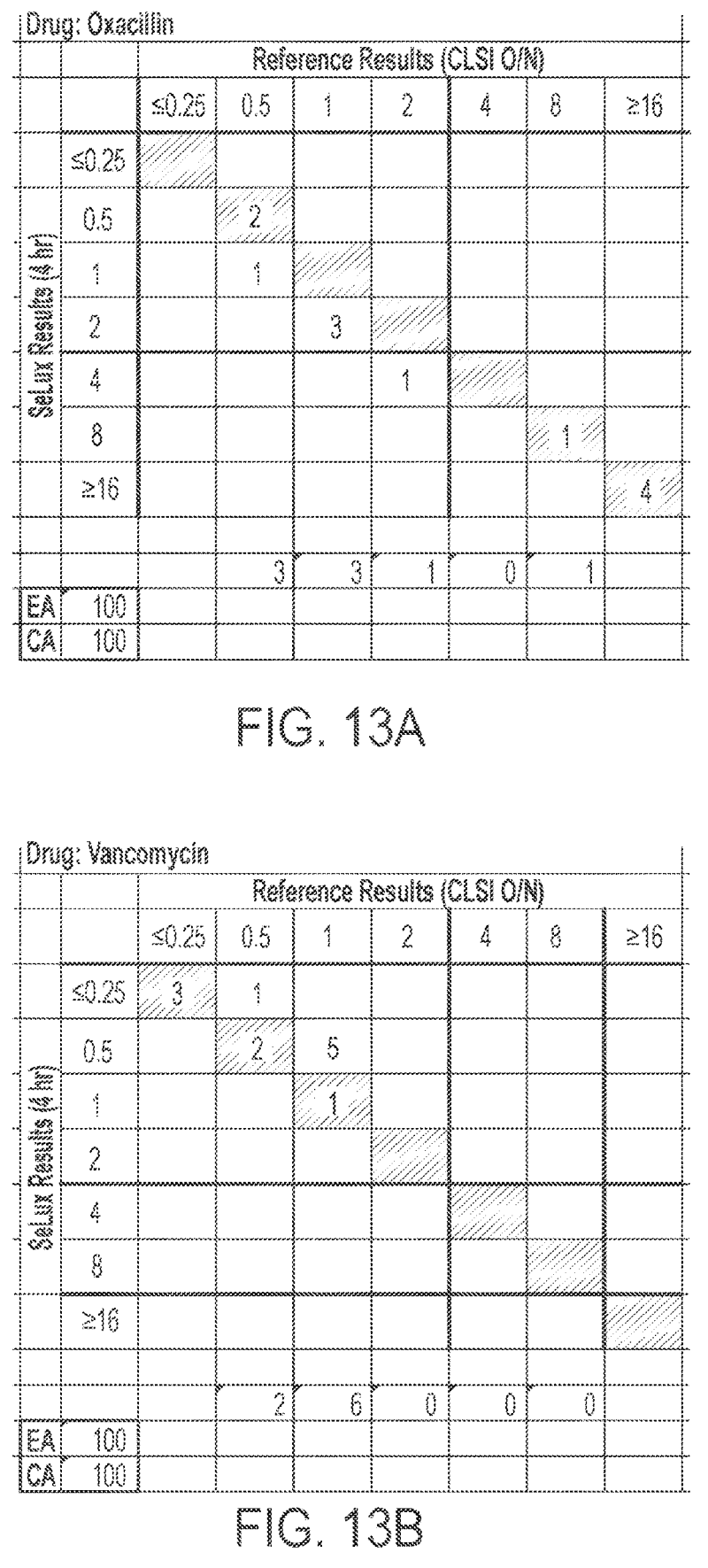

FIG. 13A to FIG. 13C is a graph showing a comparison between MIC results obtained by the present invention and the CLSI reference method for the antimicrobials oxacillin (FIG. 13A), vancomycin (FIG. 13B), and levofloxacin (FIG. 13C) on *S. aureus* clinical strains.

Figures 14C, 14D:
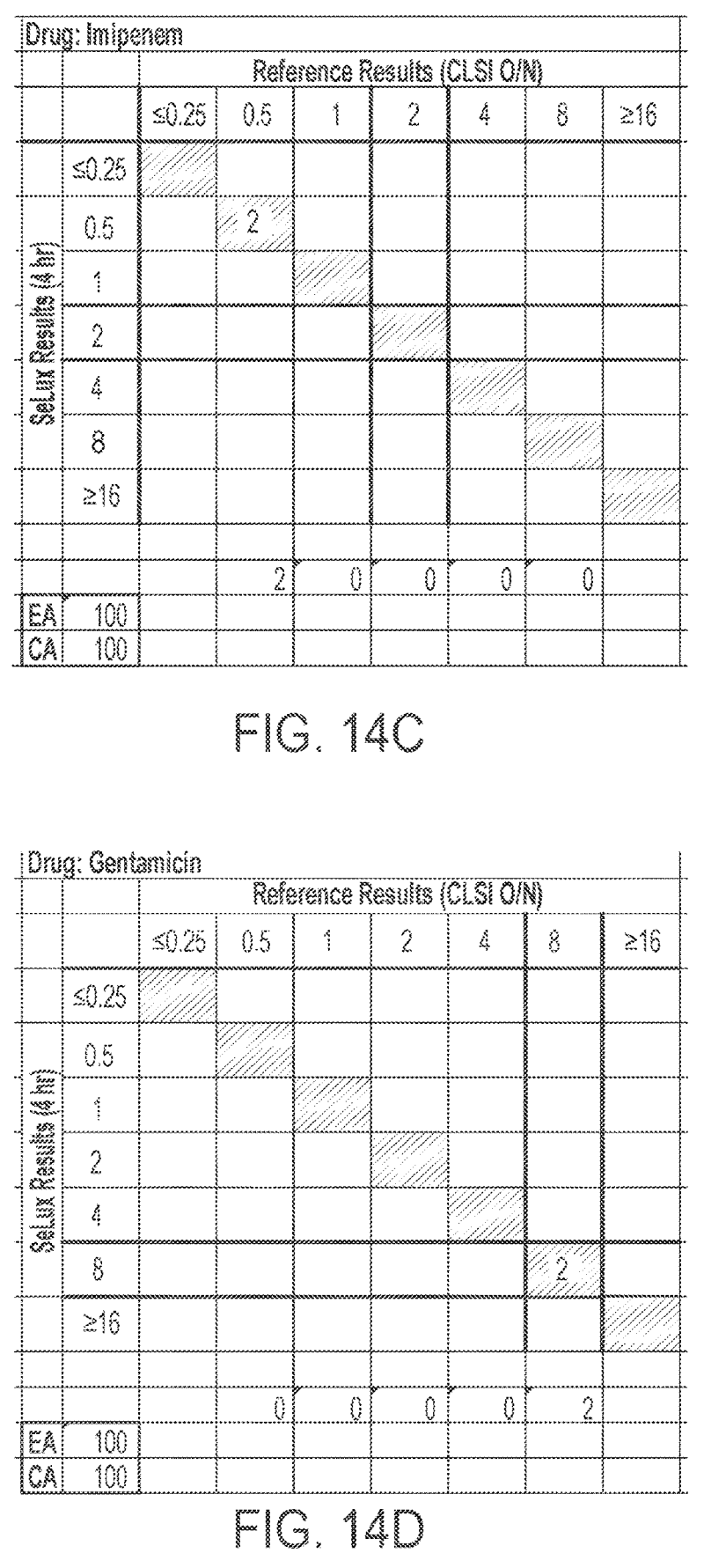

FIG. 14A to FIG. 14D is a graph showing a comparison between MIC results obtained by the present invention and the CLSI reference method for the antimicrobials ampicillin (FIG. 14A), ciprofloxacin (FIG. 14B), imipenem (FIG. 14C), and gentamicin (FIG. 14D) on *E. coli* clinical strains.

FIG. 46A to FIG. 46C show tetra-amino metalorganic ligand (TAML®) nanolabel design and performance. FIG. 46A is a schematic showing nanolabel constituents. FIG. 46B is a graph showing catalytic comparison of HRP and TAML (inset); the dashed lines are linear best fits for each dataset with R2 of 0.997 for HRP and 0.987 for TAML. FIG. 46C is a graph showing the TAML nanolabel vs. HRP comparison for *C. difficile* Toxin A immunoassay. In FIG. 46B and FIG. 46C, the signals were normalized to "1" at zero concentration, errors were propagated, and error bars represent ±1 standard deviation. Experiments were repeated three times in triplicate with similar results.

DEFINITIONS

Figure 1:
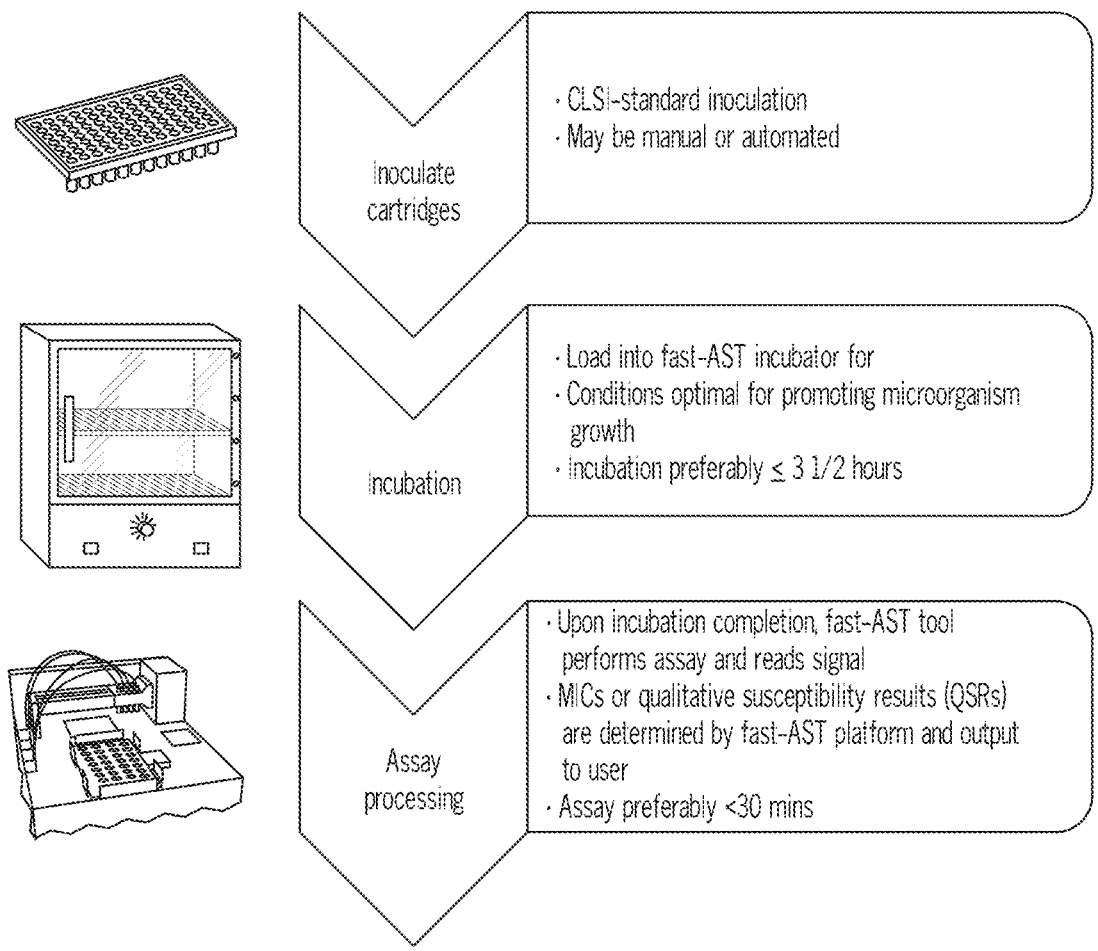
FIG. 1 is a schematic showing generalized steps of the present invention.

In order for the present invention to be more readily understood, certain terms are first defined below. Additional definitions for the following terms and other terms are set forth throughout the Specification.

As used in this Specification and the appended claims, the singular forms "a," "an" and "the" include plural referents unless the context clearly dictates otherwise.

Unless specifically stated or obvious from context, as used herein, the term "or" is understood to be inclusive and covers both "or" and "and".

The terms "e.g.," and "i.e." as used herein, are used merely by way of example, without limitation intended, and should not be construed as referring only those items explicitly enumerated in the specification.

The terms "one or more", "at least one", "more than one", and the like are understood to include but not be limited to at least 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more and any number in between.

Conversely, the term "no more than" includes each value less than the stated value. For example, "no more than 100 nucleotides" includes 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, and 0 nucleotides.

The terms "plurality", "at least two", "two or more", "at least second", and the like, are understood to include but not limited to at least 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more and any number in between.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

Unless specifically stated or obvious from context, as used herein, the term "about" is understood as within a range of normal tolerance in the art, for example within 2 standard deviations of the mean. "About" can be understood to be within 10%, 9%, 8%, 7%, 6%, 5%, 4%, 3%, 2%, 1%, 0.5%, 0.1%, 0.05%, 0.01%, or 0.001% of the stated value. Unless otherwise clear from the context, all numerical values provided herein are modified by the term "about".

A surface can be an external surface of cell wall, cell envelope, plasma membrane, or cell capsule; internal surface of cell wall, cell envelope, plasma membrane, or cell capsule; or within a cell wall, cell envelope, plasma membrane, or cell capsule. The surface may include structures of the cell projecting extracellularly, including but not limited to cilium, pilus, and flagellum. The surface may include an organelle. The surface may include transmembrane proteins, cell-wall proteins, extracellular proteins, intracellular proteins, extracellular-associated polysaccharides, intracellular-associated polysaccharides, extracellular lipids, intracellular lipids, membrane lipids, cell-wall lipids, proteins, polysaccharides, and/or lipids integral to or associated with a cell envelop. The surface may include a nucleic acid.

The surface may include a biomolecule to which the signaling agent binds or associates. Exemplary biomolecules include peptidoglycans, mureins, mannoproteins, porins, beta-glucans, chitin, glycoproteins, polysaccharides, lipopolysaccharides, lipooligosaccharides, lipoproteins, endotoxins, lipoteichoic acids, teichoic acids, lipid A, carbohydrate binding domains, efflux pumps, other cell-wall and/or cell-membrane associated proteins, other anionic phospholipids, and a combination thereof.

Growth, as in growth of microorganisms, includes a proliferation in number, an increase in length, an increase in volume, and/or an increase in nucleic acid and/or protein content of the microorganisms.

Controls may include antimicrobials for which the microorganism are not susceptible. As examples, if the assay is used to determine the susceptibility of gram-positive bacteria, then the controls (and the test incubations) may include one or more antimicrobials that target gram-negative bacteria and if the assay is used to determine the susceptibility of eukaryotic microorganisms, the control (and the test incubations) may include one or more antibacterial antimicrobials.

A control may be a positive control measured from microorganisms under otherwise identical conditions but without antimicrobials or with one or more antimicrobials for which the microorganisms are not susceptible.

A control may be measured from microorganisms under otherwise identical conditions but without nutrients.

A control may be measured from microorganisms under otherwise identical conditions with one or more toxins known to inhibit growth of the microorganisms.

Controls may be historic controls. Here, the test incubations may be performed after control incubations have been performed.

Alternately, controls may be performed in a cartridge distinct from the cartridge comprising the test incubations.

By "processed" is meant a step that isolates microorganisms from a biological sample, a step that increases the concentration of microorganisms obtained from a biological sample, and/or a step that increases the number of microorganisms obtained from a biological sample, e.g., by culturing the microorganisms under conditions that promote proliferation of the microorganisms.

Compounds of this invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "heterocycle", "heterocyclyl", or "heterocyclic" as used herein means nonaromatic, monocyclic, bicyclic, or tricyclic ring systems in which one or more ring members are an independently selected heteroatom. In some embodiments, the "heterocycle", "heterocyclyl", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" refers to one or more of oxygen, sulfur, nitrogen, phosphorus, and silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR+ (as in N-substituted pyrrolidinyl)).

The term "alkoxy", or "thioalkyl", as used herein, refers to an alkyl group, as previously defined, attached through an oxygen ("alkoxy") or sulfur ("thioalkyl") atom.

The terms "haloalkyl", "haloalkenyl", "haloaliphatic", and "haloalkoxy" mean alkyl, alkenyl or alkoxy, as the case may be, substituted with one or more halogen atoms. This term includes perfluorinated alkyl groups, such as —CF3 and —CF2CF3.

The terms "halogen", "halo", and "hal" mean F, Cl, Br, or I.

The terms "aryl" and "ar-", used alone or as part of a larger moiety, e.g., "aralkyl", "aralkoxy", or "aryloxyalkyl", refer to an optionally substituted C6-14aromatic hydrocarbon moiety comprising one to three aromatic rings. For example, the aryl group is a C6-10aryl group (i.e., phenyl and naphthyl). Aryl groups include, without limitation, optionally substituted phenyl, naphthyl, or anthracenyl. The terms "aryl" and "ar-", as used herein, also include groups in which an aryl ring is fused to one or more cycloaliphatic rings to form an optionally substituted cyclic structure such as a tetrahydronaphthyl, indenyl, or indanyl ring. The term "aryl" may be used interchangeably with the terms "aryl group", "aryl ring", and "aromatic ring".

The compounds of this invention can exist in free form for treatment, or where appropriate, as a pharmaceutically acceptable salt.

As used herein, the term "aromatic" includes aryl and heteroaryl groups as described generally below and herein The term "aliphatic" or "aliphatic group", as used herein, means an optionally substituted straight-chain or branched $C_1$-12 hydrocarbon which is completely saturated or which contains one or more units of unsaturation. For example, suitable aliphatic groups include optionally substituted linear or branched alkyl, alkenyl, and alkynyl groups. Unless otherwise specified, in various embodiments, aliphatic groups have 1-12, 1-10, 1-8, 1-6, 1-4, 1-3, or 1-2 carbon atoms. It is apparent to a skilled person in the art that in some embodiments, the "aliphatic" group described herein can be bivalent.

The term "alkyl", used alone or as part of a larger moiety, refers to a saturated, optionally substituted straight or branched chain hydrocarbon group having 1-12, 1-10, 1-8, 1-6, 1-4, 1-3, or 1-2 carbon atoms.

The term "alkenyl", used alone or as part of a larger moiety, refers to an optionally substituted straight or branched chain hydrocarbon group having at least one double bond and having 2-12, 2-10, 2-8, 2-6, 2-4, or 2-3 carbon atoms.

The term "alkynyl", used alone or as part of a larger moiety, refers to an optionally substituted straight or branched chain hydrocarbon group having at least one triple bond and having 2-12, 2-10, 2-8, 2-6, 2-4, or 2-3 carbon atoms.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures where there is a replacement of hydrogen by deuterium or tritium, or a replacement of a carbon by a 13C- or 14C-enriched carbon are within the scope of this invention. Such compounds are useful, as a nonlimiting example, as analytical tools or probes in biological assays:

It is to be understood that, when a disclosed compound has at least one chiral center, the present invention encompasses one enantiomer of inhibitor free from the corresponding optical isomer, racemic mixture of the inhibitor and mixtures enriched in one enantiomer relative to its corresponding optical isomer. When a mixture is enriched in one enantiomer relative to its optical isomers, the mixture contains, for example, an enantiomeric excess of at least 50%, 75%, 90%, 95% 99% or 99.5%.

Unless otherwise defined, all technical and scientific terms used herein have the same meaning as commonly understood by one of ordinary skill in the art to which this application belongs and as commonly used in the art to which this application belongs; such art is incorporated by reference in its entirety. In the case of conflict, the present Specification, including definitions, will control.

DETAILED DESCRIPTION OF THE INVENTION

The present invention permits rapid determination of antibiotic susceptibility of microbial infections. The invention is based in part upon the surprising discovery of non-specific surface binding assays that provide accurate and rapid Antimicrobial Susceptibility Testing (AST) determinations in fewer than twelve hours—and, specifically, under four hours. The present invention ("fast-AST") provides accurate results that are consistent with results obtained using the Clinical Laboratory Standards Institute (CLSI) reference methods and when tested with multiple antimicrobials and on a plurality of microorganisms; however, the present invention takes significantly less time to obtain results than the CLSI methods. Moreover, the present invention accurately differentiates an antimicrobial's MIC for clinically-relevant microbial strains that are resistant to one or more antimicrobials and the antimicrobial's MIC for strains of the same microorganism that are sensitive to the antimicrobials. Furthermore, the present invention may include signaling agents (e.g., Europium compounds) that are bound to microorganisms non-specifically rather than specifically (e.g., via chemically conserved groups or biochemically conserved binding sites on microorganisms), thereby expanding the generalization of the present invention to any microorganism and allowing onset of an appropriate treatment without first needing to identify the particular infectious microorganism. Also, the present invention permits signal amplification such that microbes may be rapidly detected at lower concentrations, e.g., from a dilute culture of microorganisms or via a patient's biological sample. Additionally, the present invention may use Europium formulations as chemical moiety, thereby expanding the dynamic range of the methods and allowing for more accurate determinations from a range of microbial samples. Finally, the present invention is compatible with existing equipment, thereby enabling rapid adoption in current clinical laboratories. Accordingly, the present invention, in a greatly reduced amount of time and expense, relative to standard methods, can provide a patient with an appropriate treatment regimen, i.e., a specific antimicrobial and at a particular dosage. Thus, the present invention will improve patient outcomes, lower hospital costs, and help reduce further evolution of antimicrobial resistant microorganisms; thus, the present invention represents a significant breakthrough in the AST field.

Aspects of the present invention deliver accurate, low-cost phenotypic AST results by chemically amplifying microorganism surfaces. This novel approach offers two primary advances over currently-used methods: 1) Quantification of microorganism growth by determining relative surface area, which overcomes limitations of current platforms with regard to filamentous growth regimes, as are well known to those skilled in the art; and 2) Microorganism amplification with optimal sensitivity in the $1\times10^3$ to $1\times10^8$ CFU/ml range using standard optical detection equipment.

As disclosed herein (e.g., in the Examples), the present invention has been shown to deliver equivalent results to the gold-standard for a broad range of microorganism species, including all six (*Enterococcus faecium, Staphylococcus aureus, Klebsiella pneumoniae, Acinetobacter baumannii, Pseudomonas aeruginosa,* and *Enterobacter* species) ("ES-KAPE") pathogens. Because of the generality of the present invention, it is flexible, in that it can be easily and cheaply adapted to new microorganism species strains and diagnostic tests.

The present invention provides low-cost, phenotypic ASTs from standard microbial colony isolates or from direct-from-positive blood samples, in less than 8 hours, preferably less than 5 hours. This allows standard clinical microbiology laboratories same-shift, phenotypic AST results. The below working Examples demonstrate that chemical amplification of microorganism surfaces produces accurate minimum inhibitory concentration (MIC) and breakpoint calls in less than four hours. This will shorten current wait times by over twenty hours and will match direct-from-positive blood culture MALDI-TOF identifications currently nearing FDA trials, as well as direct-from-positive blood culture multiplex PCR identification platforms that have already obtained FDA clearance. This design enables the present invention ("fast-AST" platform) to break the traditional speed vs. cost tradeoff. The present invention is compatible both with standard microplate formats (e.g., having 6, 12, 24, 48, 96, 384, or 1536 wells) and conventional optical detectors.

Identification and antimicrobial susceptibility testing (AST) of the invading pathogen with speed and accuracy allow for timely administration of the most effective therapeutic agent. Such treatment ameliorates the infection, decreases length of stay for hospitalized patients, and diminishes the time patients are subject to broad spectrum antimicrobials, the latter contributing the global epidemic of antimicrobial resistance. In contrast, the currently-accepted over thirty hour wait for microorganism identification and susceptibility results necessitates overuse of broad-spectrum antimicrobials and longer than necessary patient stay. For this reason, the Presidential Advisory Council on Combating Antibiotic-Resistant Bacteria recently made the development and use of rapid diagnostics for the detection of antibiotic resistant bacteria one of its main goals.

The present invention, which generates more rapid and accurate AST determinations, may provide actual cost benefits of over $2,000 per patient. These value points include the more easily quantifiable (reduced length of stay and expensive treatments) and the more intangible, difficult to value (patient mortality and societal impacts from improved antimicrobial stewardship). Some of these intangible values, such as the value of antimicrobial stewardship, may become more quantified as regulatory bodies start to impose costs on hospitals for not adopting more rigorous antimicrobials stewardship programs. In September 2014, California Senate Bill 1311 was signed into law, further requiring hospitals to adopt and implement an antimicrobial stewardship policy in accordance with guidelines established by federal government and professional organizations, and to establish a physician-supervised multidisciplinary antimicrobial stewardship committee with at least one physician or pharmacist who has undergone specific training related to stewardship. In June 2016, the Centers for Medicare and Medicaid Systems (CMS) used proposed roles promoting antimicrobial stewardship in hospitals, with many industry experts expecting financial incentives to be implemented in the coming two years. The present invention will further the government's and the healthcare industry's goals of better antimicrobial stewardship.

Generalized steps of aspects of the present invention are shown in FIG. 1. Images in FIG. 1 show an aspect with distinct process steps; however, aspects of the present invention may be automated.

Figure 2A:
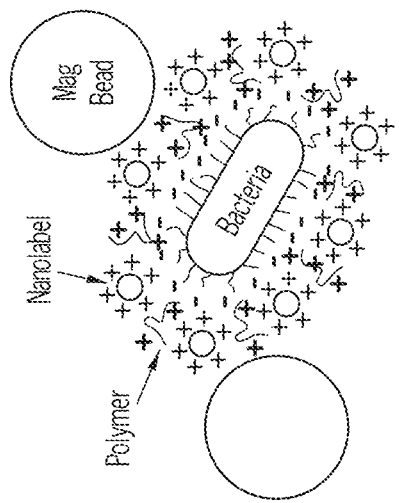
FIG. 2A to FIG. 2D are graphs and illustrations showing key features of aspects of the present invention ("fast-AST").
Figure 2B:
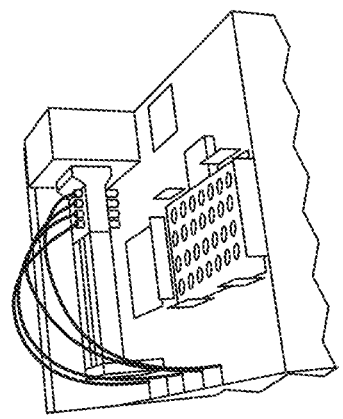
Figure 2C:
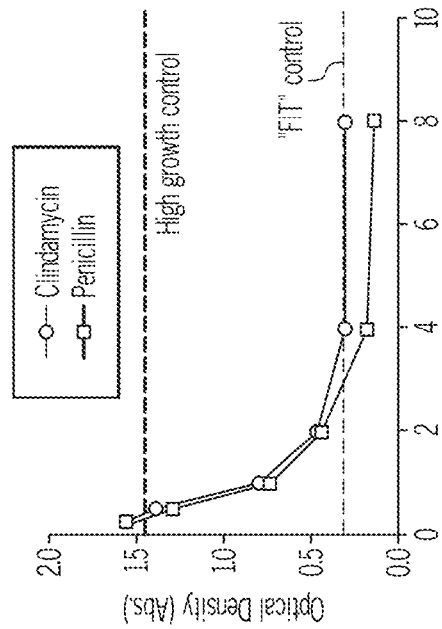
Figure 2D:
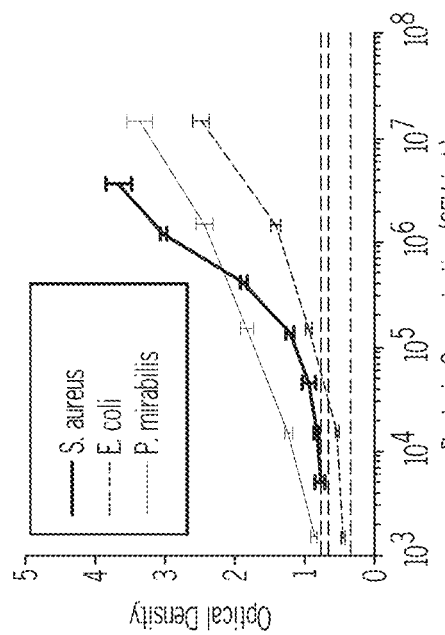

FIG. 2A to FIG. 2D show features of aspects of the present invention. FIG. 2A shows a detection sensitivity range for three representative pathogens. Dashed lines show zero-concentration signal levels. FIG. 2B shows the "Crocodile" (Titertek-Berthold) automated fast-AST prototype platform which may be used in the present invention. FIG. 2C is a schematic showing anionic bacteria interacting with cationic nanolabels and polymers. The decreased solubility of the resulting neutral complexes allows magnetic beads to bind. FIG. 2D shows data for *S. aureus* with a SensiTitre® Gram Positive panel (GPALL3F) showing a bacteriostatic (clindamycin) and bactericidal (penicillin) antimicrobial results relative to the high-growth and "frozen-in-time (FIT)" controls.

As is known to those skilled in the art, AST platforms may yield minimum inhibitory concentration (MIC) results and/or qualitative susceptibility results (QSRs) for each antimicrobial tested. MICs are commonly known to be the lowest concentration of antimicrobial that inhibits microorganism growth and provides physicians with dosing information. QSRs may also provide physicians with similar dosing information but may not provide a numerical MIC. AST assays are predominantly configured to test multiple antimicrobials in parallel for each obtained biological sample. In order to produce MIC or QSR results, dilution series are required for each antimicrobial. Thus, for liquid-based ASTs, termed "broth microdilution" by the CLSI, assays are commonly performed in cartridges and/or microplates, which enable parallel testing of different antimicrobials at different concentrations.

Long times to obtain an AST determination result in incomplete information being delivered to physicians. These long times often prevent the identification of rates of antimicrobial efficacy, or kill kinetics. This additional information may be important for informing treatment. Current ASTs, which are not determined until over six hours (and generally over twelve hours) after treatment commences, often lose the ability to discern differences between the rate of antimicrobial efficacy: an antimicrobial that kills a microorganism instantly looks the same after twelve hours as one that killed it within four hours.

Table 1 estimates the effects of different treatments on the number of bacteria after a two-hour incubation. Assuming a thirty minute doubling time, untreated controls should increase by sixteen-fold. Treatment groups with a "potent" antimicrobial (defined as one having efficacy against the bacteria, for example) above the MIC should result in minimal microorganism growth and, in the case of bactericidal antimicrobials, death of the microorganism. Thus, fewer bacteria are expected than the starting concentration. Treatment groups with a "potent" antimicrobial below its MIC should result in microorganism growth equal to or lesser than the no-antimicrobial control. Slow-acting antimicrobials, defined in this case as those requiring more than two hours to kill the bacteria (e.g., as it the case for bacteriostatic antimicrobials) will produce a signal between the starting concentration and the sixteen-fold increase.

TABLE 1

| Step | No antimicrobial | Potent antimicrobial at conc. | Step | No antimicrobial |
|---|---|---|---|---|
| Starting bacteria concentration | $5 \times 10^5$ | $5 \times 10^5$ | $5 \times 10^5$ | $5 \times 10^5$ |

TABLE 1-continued

| Step | No antimicrobial | Potent antimicrobial at conc. | Step | No antimicrobial |
|---|---|---|---|---|
| Estimated bacteria concentration after 2 hours, with 30 min. doubling time | $8 \times 10^6$ | $\leq 8 \times 10^6$ | $<5 \times 10^5$ | $5 \times 10^5$ to $<8 \times 10^6$ |

The starting concentration of bacteria of $5 \times 10^5$ CFU/ml is given in the American Society for Microbiology's "Manual of Antimicrobial Susceptibility Testing" © 2005, with Marie B. Coyle as the coordinating editor, for the broth micro dilution technique. Since each well contains approx. 100 µL, there are approx. $5 \times 10^4$ bacteria per well. Standard fluorescent dyes begin to be quantifiable at approx. 0.1 nM concentrations, which correspond to approximately $1.2 \times 10^{10}$ molecules. Thus, for a thirty minute doubling time bacteria to be visible after two hours, each individual bacterium would have to be labeled with $1.5 \times 10^4$ fluorescent molecules. Practical considerations, such as fluorescent background and non-specific binding, may increase this number by orders of magnitude. In order to enable compatibility with standard optical detectors, it may thus be advantageous to use a chemical and/or biochemical amplifier that produces a detectable signal at lower concentrations.

Without wishing to be bound by theory, the present invention is based in part on the principle of broth micro dilution. A culture to be assessed is diluted, most preferably to $1$-$10 \times 10^5$ CFU/ml, and introduced to wells containing different antimicrobials at different concentrations, such that MICs can be determined for an appropriate panel of antimicrobials. The plate is then introduced into an incubator at the appropriate temperature, most preferably 31-37° C., and under appropriate conditions, most preferably aerobic, for growing bacteria. During this time, the microorganism can grow.

The broth may be cation-adjusted Mueller Hinton broth and may contain additional supplements known by those skilled in the art to be advantageous for microbial growth, such as lysed horse blood, and/or for determining antimicrobial efficacies, such as high sodium chloride concentrations. The microplates may be agitated during this growth period, which may be advantageous for dispersing nutrients and/or gas exchange and/or antimicrobials in each well and/or decreasing biofilm formation.

Within zero to eight hours of the AST onset (most preferably zero to four hours), a known quantity of signaling agent is added to each well. Adding reagents (including signal generators) may be performed by an automated instrument or a semi-automated instrument or may be performed manually.

Signaling agents (which may be referred to as "sticky-amps") comprise a moiety capable of binding to a microorganism (e.g., an antibody and/or a lectin that bind to a microorganism surface, a charged moiety and/or a functional moiety that non-specifically binds to the microorganism surface) and a chemical moiety capable of providing a signal or contributing to production of a signal (e.g., an enzyme chemiluminophore, and lanthanide chelate). Exemplary enzymes include horseradish peroxidase, alkaline phosphatase, acetyl cholinesterase, glucose oxidase, beta-D-galactosidase, beta-lactamase, and a combination thereof.

As used herein, signal generator may include one or more chemical moieties (i.e., "signal generators") conjugated to one or more "microorganism receptors." Signal generators include, but are not limited to, one or more catalysts (including enzymes, metal-oxide nanoparticles, organometallic catalysts, nanoparticles designed for signal amplification (such as those described in the U.S. Provisional Applications to which the present application claims priority and incorporates by reference in their entireties), bacteriophages comprising signal generating elements, fluorophores (including organic fluorophores, europium, or ruthenium(II), rhenium(I), palladium(II), platinum(II)-containing organometallics), and/or colorimetric dyes (including organic "stains"). Combinations of the above may be used, such as nanoparticles, dendrimers, and/or other nanoscale structures with enzymes, fluorophores, and/or organometallic molecules.

The chemical moiety may be conjugated to a signaling agent before contacting the signaling agent to a microorganism, while the signaling agent is initially contacted to a microorganism, or after the signaling agent has contacted a microorganism.

When the signaling agents are added to AST dilutions containing a microorganism, signaling agent receptors (e.g., moieties that can bind specifically or non-specifically to a microorganism) associate with microorganism surfaces. Thus, the more intact microorganisms, for example, there are in solution, the greater the number of signaling agents that will be associated with these bacteria. Consequently, there is an inverse relationship between the number of intact bacteria and the number of signaling agents that are "free" in solution, as defined by those not bound to intact bacteria. Note that free signaling agents may be bound to soluble microbial components if, for example, microorganisms lyse in response to antimicrobial treatment.

The number of signaling agents that associate with and/or intercalate into microorganism surfaces is proportional to the microorganism surface area. Microorganism surface area is strongly associated with truly resistant microorganisms. In particular, in the case of microorganisms that swell or elongate in response to MIC- and sub-MIC concentrations of antimicrobials (e.g., filament forming bacteria), metabolic and/or volumetric identifications are known to give false susceptibility profiles for "rapid" AST time points, defined as those less than six hours. To overcome this limitation, the present invention translates microorganism surface area (rather than volume) into a measurable signal, most preferably an optical signal. The present methods are able to accurately determine microorganism resistance profiles in less than six hours.

In order to separate signaling agents associated with and/or intercalated into microorganisms from free signaling agents, it may be necessary to perform one or more separation and/or competitive binding steps. Such steps include, but are not limited to, centrifugation (e.g., with a g-force $>500 \times g$), filtration (e.g., via a filter having pores smaller than or equal to 0.45 microns, and preferably smaller than or equal to 0.2 microns), electrophoresis, and/or magnetic capture; such steps are well-known to those skilled in the art.

In order to promote signaling agent binding and/or reduce background, it may further be advantageous, before adding signaling agents, to separate microorganisms from the liquid in which they were suspended during incubation. Such separations may include but are not limited to, centrifugation, filtration, electrophoresis, and/or magnetic capture.

When these data are compared across treatment groups, microbial resistance profiles may be determined, using steps similar to currently-used AST determinations. Additionally, these data may enable determination of rates of antimicrobial efficacy, or kill kinetics.

Signaling agents may be added together with microorganisms and/or antimicrobials, such that they are present for the entire AST incubation period. This total period may be up to twenty-four hours but is preferably within eight hours and more preferably within five hours. Alternatively, signaling agents may be added to microorganisms and antimicrobial after a prescribed incubation period. This period may be up to twenty-four hours but is preferably within eight hours and more preferably within four hours.

Signaling agents are designed to associate with and/or intercalate in microorganism surfaces, including walls and/or membranes. Signaling agents designed for association comprise binding moieties including, but are not limited to, one or more antibodies, lectins, other proteins, small molecules with one or more charged chemical groups, small molecules with one or more functional chemical groups, phages, glycoproteins, peptides, aptamers, charged small molecules, small molecules with fixed charges, charged polymers, charged polymers with fixed charges, hydrophobic small molecules, charged peptide, charged peptides with fixed charges, peptides with alternating hydrophilic and hydrophobic regions, and/or small molecule ligands, which may or may not be organometallic complexes. Molecules designed for microorganism association are well-known to those skilled in the art. Signaling agents may remain bound to microorganisms and/or may be internalized, thus all associations are included. Signaling agents designed for intercalation may include, but are not limited to, small hydrophobic molecules, hydrophobic peptides, and/or peptides with alternating hydrophobic and hydrophilic regions. Molecules designed for microorganism intercalation are well-known to those skilled in the art. Signaling agents may further be specific to one or more types of microorganisms. Signaling agents may have multiple receptors. These may enhance binding and/or enable simultaneous binding to two or more microorganisms, which may further serve to "agglutinate" bacteria. Prior to or concurrently with the addition of signaling agents it may be advantageous to adjust the solution pH. This may be beneficial for enhancing charge-charge interactions between microorganisms and signaling agents. The anionic charge of microorganisms may be increased by titrating the solution pH above neutral (more basic). It may thus be beneficial to utilize moieties with one or more fixed, cationic charges.

It is noteworthy that the signaling agent may specifically bind to a microorganism (e.g., an antibody that specifically binds to a microorganism species or a strain of microorganism) or my non-specifically binds to a microorganism (e.g., by a generic covalent or non-covalent bond formation and another non-specific chemical association known in the art).

It is preferred that signaling agents bind native microorganism surfaces.

Alternately, chemicals and/or biochemicals which are capable of associating with signaling agents may be added to the liquid in which the microorganisms are suspended during growth, such that chemicals and/or biochemicals are incorporated into microorganisms during incubation. This may serve to enhance signaling agent association with microorganisms. In alternative embodiments, the signaling agents themselves may be present in the liquid in which the microorganisms are suspended during incubation and may be incorporated into microorganisms during growth.

Preferably the signaling agents comprise an amplifier signal generator, such that the signal from each intact microorganism may be amplified beyond the number of signaling agents associated with each microorganism. For example, the enzyme horseradish peroxidase (HRP) is known to be able to amplify signals $>1\times10^4$-fold. Thus, if one hundred HRP molecules are bound to each microorganism surface, an amplification of $10^6$ may be achieved. This may increase the speed with which AST determinations may be made by enabling discrimination of microorganism concentrations that cannot otherwise be differentiated. Use of Europium formulations similarly provides signal amplification.

Alternatively, the signaling agents may comprise optical dye precursors known to those skilled in the art as "membrane dyes" that are designed to greatly increase fluorescence emission upon intercalation into a hydrophobic region, such as a cell membrane. Assays designed with these signaling agents may require microorganisms to be concentrated into a smaller volume, approaching a plane, to produce sufficient signals so as to be easily optically measured. Interfering species may require the use of near-IR fluorophores.

Potential separation techniques include, but are not limited to, filtering (e.g., via a filter having pores smaller than or equal to 0.45 microns, preferably smaller than or equal to 0.2 microns), centrifugation (e.g., with a g-force $>500\times g$), electrophoresis, dielectrophoresis, and magnetic capture. These techniques are employed to separate signaling agents associated with microorganisms, which are stuck in a filter, pelleted in a centrifuge, and/or separated electrophoretically and/or magnetically, from those free in solution. Free signaling agents pass through a filter ("filtrate"), remain in solution after centrifugation or magnetic separation ("supernatant"), and/or run separately electrophoretically. Centrifugation may be standard, density gradient, or differential centrifugation. Magnetic separation may require the addition of one or more magnetic particles specifically targeted to associate with or bind to microorganisms. These may be added prior to or concurrently with signaling agent addition.

Such separation techniques may also isolate microorganisms that change morphology in response to an antimicrobial treatment and may confound a determination. An example of such a microorganism is filamentous bacteria which initially elongate in response to antimicrobial treatment. This growth regime is known to those skilled in the art. Isolating and excluding filamentous bacteria from an assay, using a herein-described separation technique, will increase the accuracy of the obtained results.

Microorganism separation may be enhanced through the association of particles with microorganism species. For example, in the case of magnetic separation, magnetic beads may associate with microorganisms (specifically or non-specifically). Moieties present on magnetic bead surfaces may bind the same surface (or a biomolecule thereof) of microorganisms as the singling agent or different surface (or a biomolecule thereof). The magnetic beads may have the same and/or different moieties as the signaling agents. For example, if a signaling agent comprises an antibody that binds to E. coli, then a magnetic bead may be functionalized with the same antibody. In other examples, the signaling agent may include a motif that binds a microorganism and the magnetic bead is functionalized to non-specifically bind to microorganisms.

The one or more binding moieties associated with the magnetic beads may be identical of different to the chemical moiety associated with or of the signaling agent.

The one or more binding moieties associated with the magnetic beads may bind the microorganisms prior to, simultaneously with, or subsequent to the biding of the signaling agent with the microorganism.

The one or more binding moieties associated with the magnetic beads may associate with one or more polymers that precipitate microorganisms. The one or more polymers that precipitate microorganisms may cationic. The one or more polymers that precipitate microorganisms may be poly(ethylene glycol).

Magnetic beads, as are known to those skilled in the art, may range in size from 20 nm to 20 microns.

After separation, one or more assays to determine the number of signaling agents remaining after microorganism separation and/or the number of signaling agents removed during microorganism separation ("free" signaling agents) may be performed. Performing an assay for free signaling agents provides a signal inversely proportional to microorganism concentration. In this case signaling agents associated with microorganisms may be either bound to or internalized by microorganisms. Alternatively, an assay may be performed for signaling agents associated with microorganisms. In this case, unless microorganisms are specifically lysed, only bound signaling agents will contribute to the signal.

In order to maximize separation efficiency, i.e., minimize the number of free signaling agents remaining, one or more washing steps may be performed. These may be continuous, as in the cases of filtering, magnetic capture, or electrophoresis, and/or discrete, as in the cases of centrifugation or magnetic capture.

In alternative embodiments, signaling agents may not require washing. This may be the case when "membrane dye" signaling agents are used. Molecules not intercalated into microorganism membranes have significantly lower optical activities than intercalated species, thus washing may not be required.

One or more washes may be performed before signaling agents are added to the microorganisms. These washes may, for example, remove interfering species present in the liquid in which the microorganisms were suspended during incubation.

In embodiments, no wash is performed.

Signal development may require the addition of a "development solution." For signaling agents comprising catalysts, the development solution may comprise one or more signal precursors that can be converted to an optically and/or electrically active signaling molecule. For signaling agents comprising encapsulated molecules, such as within nanoparticles, the development solution may comprise one or more reagents to release the encapsulated species. At a specified time after addition of the development solution, a colorimetric and/or electrochemical signal may be measured. Such signals include, but are not limited to, absorbance, fluorescence, time-resolved fluorescence, chemiluminescence, electrochemiluminescence, amperometric, voltammetric, impedance, and/or impedance spectroscopy. The data may then be compared to determine ASTs and MICs, similarly to current AST protocols.

In embodiments, determining signal levels includes measuring the signal levels associated with intact microorganisms. Alternately or additionally, determining signal levels includes measuring the signal levels not associated with intact microorganisms.

These processes may be performed directly from cultures, sub-cultures, positive blood cultures, samples. Treatments to concentrate microorganisms and/or remove potential interfering species may be performed prior to AST or prior to signaling agent addition.

Signaling agents may also be used with plate-based methods for AST determination, such as gradient diffusion. They may be added simultaneously upon microorganism addition to plates or following a set incubation period. Spatial information for the optical and/or electrical signal is important in these cases. With this approach an assay for intact microorganism-bound signaling agents may be preferable in order to retain spatial information. In this case, one or more wash steps may be performed prior to the addition of the development solution in order to remove free signaling agents.

In embodiments, no wash is performed.

Alternatively, signaling agents may be designed to be up-taken by bacteria, e.g., which may be achieved through the use of bacteriophages. In such methods, an assay for free signaling agents is performed.

Alternatively, a blot-transfer approach, such as is standard with nitrocellulose paper, may be used to transfer bacteria or free signaling agents and a spatial assay then performed on the blotted paper.

Separation step(s) may not be required if the signaling agent produces a signal upon binding. Alternatively, a separation step-free process may be achieved if the signaling agent becomes susceptible or resistant to a specific developer solution constituent upon binding.

Final MIC and/or QSR output data may be interpreted by a user directly from the data produced by the assays described herein. Alternatively, these data may be processed by one or more algorithms to yield MICs and/or QSRs. Reported MIC and/or QSR values may be derived from one or more of the assays described herein or may be derived from one or more of the assays described herein together with one or more known assays for microorganism growth including, but not limited to, metabolic dye indicator assays, pH indicator assays, nucleic acid assays, and ATP assays.

Methods of the Present Invention

An aspect of the present invention is a method for determining antimicrobial susceptibility of microorganisms. The method includes steps of incubating a liquid suspension of microorganisms in the presence of an antimicrobial and a signaling agent under conditions that promote growth of the microorganisms, wherein the signaling agent is capable of binding to a surface of the microorganisms; separating the microorganisms bound by the signaling agent from the unbound signaling agent; and determining signal levels associated with the microorganisms as compared to one or more controls, thereby determining the antimicrobial susceptibility of the microorganisms.

Another aspect of the present invention is a method for determining antimicrobial susceptibility of microorganisms. The method includes steps of incubating a liquid suspension of microorganisms in the presence of an antimicrobial under conditions that promote growth of the microorganisms; adding a signaling agent capable of binding to a surface of the microorganisms; separating the microorganisms bound by the signaling agent from the unbound signaling agent; and determining signal levels associated with the microorganisms as compared to one or more controls, thereby determining the antimicrobial susceptibility of the microorganisms. In embodiments, adding the signaling agent occurs prior to or during the incubating step or adding the signaling agent occurs after the incubating step.

Another aspect of the present invention is a method for determining antimicrobial susceptibility of microorganisms. The method includes steps of incubating a liquid suspension of microorganisms in a cartridge comprising a plurality of chambers, each chamber containing one or more antimicrobials, under conditions that promote growth of the microorganisms; adding a signaling agent to the plurality of chambers, wherein the signaling agent is capable of binding to a surface of the microorganisms; removing unbound signaling agent; and determining signaling levels in the plurality of chambers as compared to one or more controls, thereby determining the susceptibility of microorganisms to the one or more antimicrobials. In embodiments, the cartridge further includes one or more control chambers (e.g., at least 2, 4, 6, 8, 12, 24, 48, 96, 192, 384, 1536 or more chambers) that do not contain antimicrobials or one or more antimicrobials for which the microorganisms are not susceptible.

In embodiments of an above aspect, binding to a surface of the microorganisms is non-specific, e.g., comprising a non-covalent interaction and via forming a covalent bond.

In embodiments of an above aspect, the signaling agent may include a chemical and/or biochemical group capable of binding a surface of the microorganisms, wherein the surface comprises one or more of membranes, walls, proteins, organelles, saccharides, lipids, cell envelope, and/or nucleic acids.

In embodiments of an above aspect, the signaling agent may include a chemical and/or biochemical group capable of binding a biomolecule of the surface of the microorganisms, wherein the surface biomolecule is selected from peptidoglycans, mureins, mannoproteins, porins, beta-glucans, chitin, glycoproteins, polysaccharides, lipopolysaccharides, lipooligosaccharides, lipoproteins, endotoxins, lipoteichoic acids, teichoic acids, lipid A, carbohydrate binding domains, efflux pumps, other cell-wall and/or cell-membrane associated proteins, other anionic phospholipids, and a combination thereof.

In embodiments of an above aspect, the signaling agent may include a signal amplifier and one or more chemical moieties capable of binding non-specifically to a surface of the microorganisms.

Another aspect of the present invention is a method for determining antimicrobial susceptibility of microorganisms. The method includes incubating microorganisms in the presence of an antimicrobial and a signaling agent under conditions that promote growth of the microorganisms, wherein the signaling agent comprises a signal amplifier and one or more chemical moieties capable of binding non-specifically to a surface of the microorganisms; separating the microorganisms bound by the signaling agent from the unbound signaling agent; and determining signal levels associated with the microorganisms as compared to one or more controls, thereby determining the antimicrobial susceptibility of the microorganisms.

Another aspect of the present invention is a method for determining antimicrobial susceptibility of microorganisms. The method includes incubating microorganisms in the presence of an antimicrobial under conditions that promote growth of the microorganisms; adding a signaling agent comprising a signal amplifier and one or more chemical moieties capable of binding non-specifically to a surface of the microorganisms; separating the microorganisms bound by the signaling agent from the unbound signaling agent; and determining signal levels associated with the microorganisms as compared to one or more controls, thereby determining the antimicrobial susceptibility of the microorganisms. In embodiments, the signaling agent occurs prior to, at the beginning of, or during the incubating step, preferably during the incubating step. In embodiments, the microorganisms are incubated in a liquid suspension.

In embodiments of an above aspect, the liquid suspension may be prepared by inoculating a liquid media with a microbial isolate grown from a biological sample.

In embodiments of an above aspect, the liquid suspension of microorganisms may be prepared from an unprocessed biological sample, e.g., an unprocessed biological sample has not undergone a culturing step.

In embodiments of an above aspect, the liquid suspension of microorganisms may be prepared from a cultured or processed biological sample.

In embodiments of an above aspect, the biological sample is selected from blood, cerebrospinal fluid, urine, stool, vaginal, sputum, bronchoalveolar lavage, throat, nasal/wound swabs, and a combination thereof.

In embodiments of an above aspect, the method does not involve a step of capturing microorganisms on a solid surface prior to or during incubation.

In embodiments of an above aspect, the method does not include a step of growing microorganisms on a solid surface during or subsequent to the incubating step.

In embodiments of an above aspect, the incubating may include agitating the liquid suspension of microorganisms.

In embodiments of an above aspect, the liquid suspension of microorganisms may be agitated by means of mechanical, acoustic, and/or magnetic agitation continuously or discretely during the incubating.

In embodiments of an above aspect, the incubating occurs at 31-37° C. Comparison of the present invention to currently-used AST systems The present invention is superior to currently-used AST methods, in part because it provides accurate AST results in significantly less time.

Figure 3:
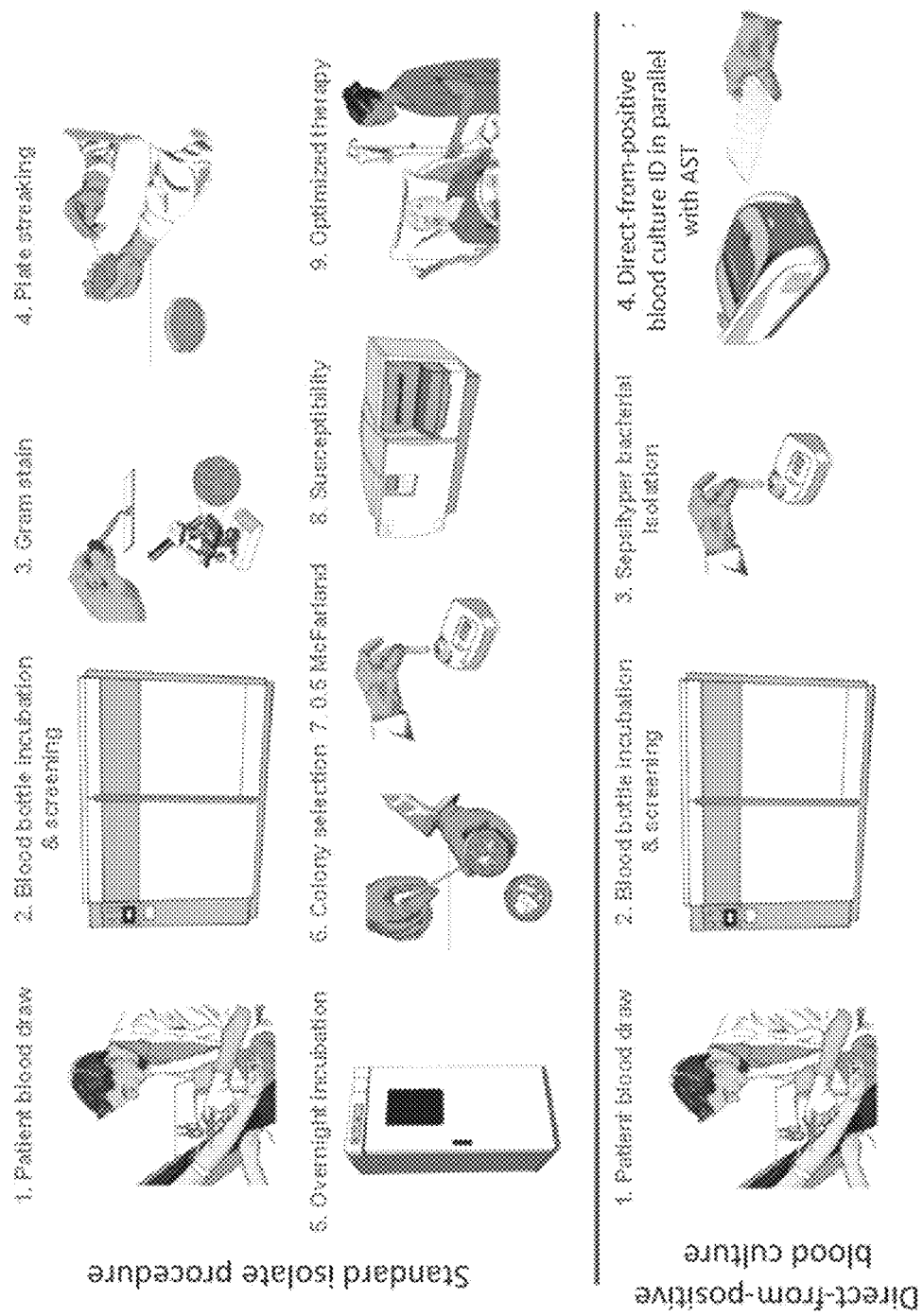
FIG. 3 is a schematic comparing steps required in currently-used Antimicrobial Susceptibility Testing (AST) systems and aspects of the present invention.

Three automated AST systems that are currently used in clinics are BioMeriéux's Vitek2, Beckman Dickinson's Phoenix, and Beckman-Coulter's MicroScan. A comparison between steps in currently-used AST systems and the present invention are shown in FIG. 3. The processes described in this invention may be performed in at least two modes. The first is for standard isolates, with no changes to current laboratory workflows. The second is direct from positive blood cultures.

For standard isolate processing, the present invention is compatible with existing clinical laboratory workflows and, thus, requires no changes. As shown in "step 8" of FIG. 3, current susceptibility (AST) testing is performed after colony isolation (step 6) and microorganism concentration standardization (step 7). In this workflow, the present invention would replace current systems at "step 8." Because AST results with the present invention are available within a healthcare worker's the shift (<5 hours), utility may increase the speed with which patients receive optimized therapies (step 9) by up to one day in practice. Automation may be designed to include "step 7" and, potentially, additional steps in the workflow. Such automation is known to those skilled in the art. Note that FIG. 3 illustrates the workflow for blood samples. Many sample types, such as urine and swabs, may be streaked directly on plates (step 4). In this case, the gram stain may be performed at step 6.

For a blood test, the currently-used AST systems require an obtained blood culture to become detectibly positive (which takes ten or more hours), followed by a sub-culture step (of at least twelve hours), and then an AST test (which requires a minimum of eight hours): this totals over forty-eight hours, depending on the pathogen, and often takes greater than three days in practice. In most workflows, the identification of the organism happens after the sub-culture step and increasingly done by mass spectrometry. Since both identification and AST results are required for clinicians or pharmacists to prescribe proper targeted antimicrobials, this delay to AST results directly extends the duration of broad-spectrum antimicrobial treatment. Furthermore, the wait is often compounded by one-shift operation common in many clinical microbiology laboratories.

Alternatively, the present invention may be used directly from positive blood cultures. After the standard step 1 and step 2 of blood draw and incubation/culture, if the culture is positive, the culture bottle would move directly to a microorganism isolation (step 3) and then into an automated system (step 4). The present invention can be fully automated, requiring a technician to only load the system with a standard cartridge with microorganism dilutions and then initiate the four-hour "fast-AST" process. The lab technician would then receive the same standard phenotypic results for AST of a minimum inhibitory concentration ("MIC"). However, the streamlined process would reduce the time to AST by over twenty-four hours in theory, and potentially two days in practice, and simplify lab workflow.

The currently used AST systems perform variants of the Clinical Laboratory Standards Institute (CLSI) broth microdilution procedure. Bacteria are inoculated into multiple wells in parallel, each of which contains one (or more) antimicrobials at a known concentration and a nutrient broth. Wells are inoculated at $5 \times 10^5$ CFU/ml to ensure bacteria are in the log growth phase, important for detecting accurate responses to antimicrobials. Microorganism detection is then performed visually.

The slow speed of phenotypic AST testing is due, in part, to its reliance on microorganism growth in order to produce a detectable optical signal. Bacteria cannot be quantified by optical density measurements below a concentration of $\sim 1 \times 10^8$ CFU/ml, rendering the CLSI starting concentration invisible for a minimum of eight doubling times. Since differentiation of microorganism growth in the slowest-growing well from the no-growth well is critical for minimum inhibitory concentration (MIC) determinations, significantly longer times are required. As is known to those skilled in the art, some existing platforms overcome these growth issues by including metabolic probes in the liquid in which the microorganisms are suspended during incubation. However, inclusion of these probes may miss growth regimes, such as filamentous growth, and may impact the accuracy of results.

Figure 4:
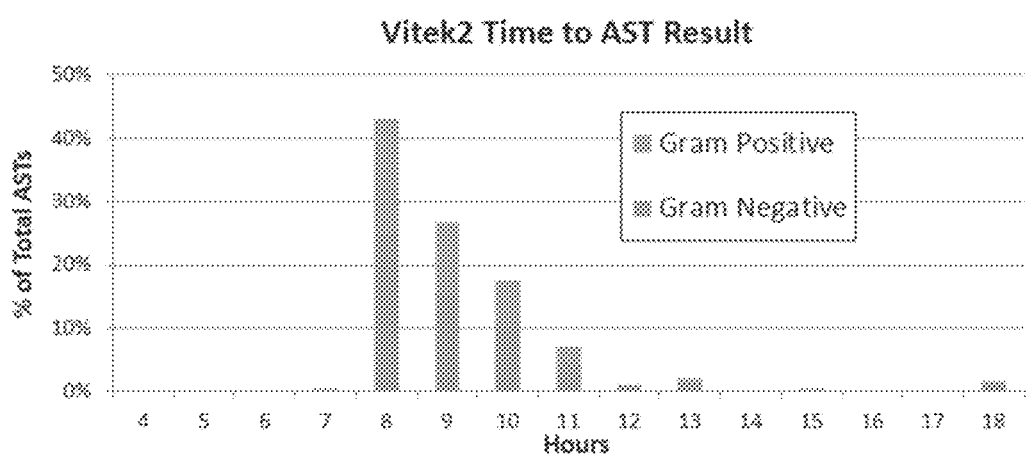
FIG. 4 is a graph showing the time delay required to obtain results using a currently-used AST system (i.e., BioMerieux's Vitek2).

Once the AST-specific steps have commenced, the currently-used AST systems still typically require over eight hours to report results for simple, highly-susceptible bacteria and require over ten hours for pathogens with complex resistance profiles or slow growth kinetics, see FIG. 4.

Additionally, the currently-used automated AST systems suffer from two shortcomings that prevent the reporting of accurate results in less than six hours: 1) very major errors, inaccurate "susceptible" calls for truly-resistant strains; and 2) major errors, inaccurate "resistant" calls for truly-susceptible strains. Indeed, these issues have required BioMeriéux and BD to revise their initial four-hour speed claims for the Vitek2® and Phoenix®.

The existence of very major errors is explained in part by the metabolic energy expended by the microorganisms in achieving antimicrobial resistance. Resistant microorganisms may alter energy expenditures in response to antimicrobials, confounding the results of metabolic probes around the MIC. These may also result from the present of additives, such as redox indicators, in the growth media. The prevalence of major errors is due primarily to filamentous growth of certain bacteria. This growth regime is a common antimicrobial response amongst gram-negative bacteria, in particular to cell-wall-acting antimicrobials, such as β-lactams. Filamentous bacteria continue to replicate their internal contents but do not septate. Thus, again, metabolic probes give erroneous near-MIC results. The removal of filamentous bacteria was shown to significantly reduce major errors for the AST method.

Figure 39:
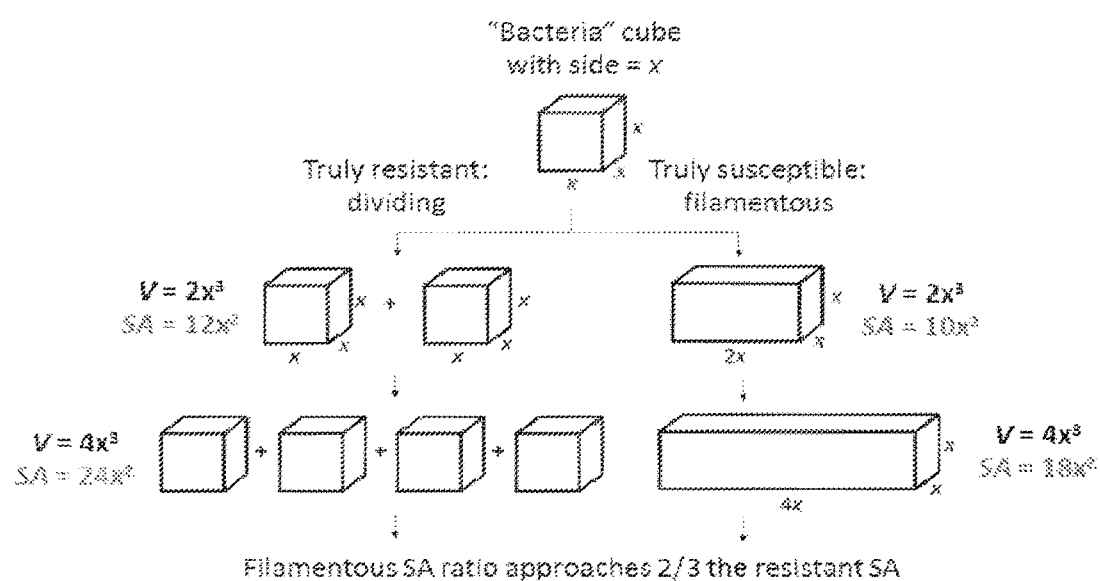
FIG. 39 is a schematic that illustrates the confounding effect that filamentous growth has on volumetric-based determinations of microorganism's antimicrobial susceptibilities. Susceptible bacteria entering filamentous growth may appear falsely resistant due to their increased volume.

Measurements of relative microorganism surface area, as used in the present invention, overcome the pitfalls of metabolic probes for AST. First, since relative surface area is not confounded by shifts in metabolic activity, fast-AST enables rapid, accurate resistance calls. Second, surface area measurements prevent over-resistance calls. In contrast to volumetric measurements obtained with metabolic probes of the currently-used AST systems, surface area measurements enable accurate differentiation between true resistance and filamentous growth. As illustrated in the schematic of FIG. 39, volumes of resistant and susceptible filamentous bacteria are difficult to distinguish. But the lack of septation creates a filamentous surface area significantly lower than that of truly resistant bacteria. Thus, by amplifying each bacteria's surface area, the present invention is able to accurately call four-hour, β-lactam (ampicillin) MICs for *E. coli* samples (see, the below Examples). As illustrated in FIG. 39, the surface area differential between elongation and "true" resistance approaches ⅔, which may be detected with an amplified signal.

Patient

As used herein, the term "patient" (also interchangeably referred to as "host" or "subject") refers to any host that can serve as a source of one or more of the biological samples or specimens as discussed herein. In certain aspects, the donor will be a vertebrate animal, which is intended to denote any animal species (and preferably, a mammalian species such as a human being). In certain embodiments, a "patient" refers to any animal host, including but not limited to, human and non-human primates, avians, reptiles, amphibians, bovines, canines, caprines, cavities, corvines, epines, equines, felines, hircines, lapines, leporines, lupines, ovines, porcines, racines, vulpines, and the like, including, without limitation, domesticated livestock, herding or migratory animals or birds, exotics or zoological specimens, as well as companion animals, pets, and any animal under the care of a veterinary practitioner.

Biological Samples

The biological sample is any sample that contains a microorganism, e.g., a bacterium and a fungal cell.

Exemplary biological samples include, but are not limited to, whole blood, plasma, serum, sputum, urine, stool, white blood cells, red blood cells, buffy coat, tears, mucus, saliva, semen, vaginal fluids, lymphatic fluid, amniotic fluid, spinal or cerebrospinal fluid, peritoneal effusions, pleural effusions, exudates, punctates, epithelial smears, biopsies, bone marrow samples, fluids from cysts or abscesses, synovial fluid, vitreous or aqueous humor, eye washes or aspirates, bronchoalveolar lavage, bronchial lavage, or pulmonary lavage, lung aspirates, and organs and tissues, including but not limited to, liver, spleen, kidney, lung, intestine, brain, heart, muscle, pancreas, and the like, swabs (including, without limitation, wound swabs, buccal swabs, throat swabs, vaginal swabs, urethral swabs, cervical swabs, rectal swabs, lesion swabs, abscess swabs, nasopharyngeal swabs, and the like), and any combination thereof. Also included are bacteria cultures or bacteria isolates, fungal cultures or fungal isolates. The ordinary-skilled artisan will also appreciate that isolates, extracts, or materials obtained from any of the above exemplary biological samples are also within the scope of the invention.

Microorganisms obtained from a biological sample may be cultured or otherwise processed as is routinely performed in the art.

Exemplary Microorganisms

As used herein, infection is meant to include any infectious agent of a microbial origin, e.g., a bacterium, a fungal cell, an archaeon, and a protozoan. In preferred examples, the infectious agent is a bacterium, e.g., a gram-positive bacterium, a gram-negative bacterium, and an atypical bacteria. The term "antimicrobial resistant microorganism" is a microorganism (e.g., bacterium, fungus, archeaon, and protozoan) that is resistant to one or more distinct antimicrobials, i.e., anti-bacterial drugs, antifungal drugs, anti-archaea medications, and anti-protozoan drugs.

The microorganisms (e.g., a liquid suspension of microorganisms) may include one strain of microorganism. The microorganisms may include one species of microorganism. The microorganisms may include more than one strain of microorganism. The microorganisms may include one order of microorganism. The microorganisms may include one class of microorganism. The microorganisms may include one family of microorganism. The microorganisms may include one kingdom of microorganism.

The microorganisms (e.g., a liquid suspension of microorganisms) may include more than one strain of microorganism. The microorganisms may include more than one species of microorganism. The microorganisms may include more than one genus of microorganism. The microorganisms may include more than one order of microorganism. The microorganisms may include more than one class of microorganism. The microorganisms may include more than one family of microorganism. The microorganisms may include more than one kingdom of microorganism.

The microorganism may be a bacterium. Examples of bacterium include and are not limited to *Acetobacter aurantius, Acinetobacter bitumen, Acinetobacter* spp., *Actinomyces israelii, Actinomyces* spp., *Aerococcus* spp., *Agrobacterium radiobacter, Agrobacterium tumefaciens, Anaplasma, Anaplasma phagocytophilum, Azorhizobium caulinodans, Azotobacter vinelandii, Bacillus, Bacillus anthraces, Bacillus brevis, Bacillus cereus, Bacillus fusiformis, Bacillus licheniformis, Bacillus megaterium, Bacillus mycoides, Bacillus* spp., *Bacillus stearothermophilus, Bacillus subtilis, Bacillus Thuringiensis, Bacteroides, Bacteroides fragilis, Bacteroides gingivalis, Bacteroides melaninogenicus* (also known as *Prevotella melaninogenica*), *Bartonella, Bartonella henselae, Bartonella quintana, Bartonella* spp., *Bordetella, Bordetella bronchiseptica, Bordetella pertussis, Bordetella* spp., *Borrelia burgdorferi, Brucella, Brucella abortus, Brucella melitensis, Brucella* spp., *Brucella suis, Burkholderia, Burkholderia cepacia, Burkholderia mallei, Burkholderia pseudomallei, Calymmatobacterium granulomatis, Campylobacter, Campylobacter coli, Campylobacter fetus, Campylobacter jejuni, Campylobacter pylori, Campylobacter* spp., *Chlamydia, Chlamydia* spp., *Chlamydia trachomatis, Chlamydophila, Chlamydophila pneumoniae* (previously called *Chlamydia pneumoniae*), *Chlamydophila psittaci* (previously called *Chlamydia psittaci*), *Chlamydophila* spp., *Clostridium, Clostridium botulinum, Clostridium difficile, Clostridium perfringens* (previously called *Clostridium welchii*), *Clostridium* spp., *Clostridium tetani, Corynebacterium, Corynebacterium diphtheriae, Corynebacterium fusiforme, Corynebacterium* spp., *Coxiella burnetii, Ehrlichia chaffeensis, Ehrlichia* spp., *Enterobacter cloacae, Enterobacter* spp., *Enterococcus, Enterococcus avium, Enterococcus durans, Enterococcus faecalis, Enterococcus faecium, Enterococcus galllinarum, Enterococcus maloratus, Enterococcus* spp., *Escherichia coli, Francisella* spp., *Francisella tularensis, Fusobacterium nucleatum, Gardenerella* spp., *Gardnerella vaginalis, Haemophilius* spp., *Haemophilus, Haemophilus ducreyi, Haemophilus influenzae, Haemophilus parainfluenzae, Haemophilus pertussis, Haemophilus vaginalis, Helicobacter pylori, Helicobacter* spp., *Klebsiella pneumoniae, Klebsiella* spp., *Lactobacillus, Lactobacillus acidophilus, Lactobacillus bulgaricus, Lactobacillus casei, Lactobacillus* spp., *Lactococcus lactis, Legionella pneumophila, Legionella* spp., *Leptospira* spp., *Listeria monocytogenes, Listeria* spp., *Methanobacterium extroquens, Microbacterium multiforme, Micrococcus luteus, Moraxella catarrhalis, Mycobacterium, Mycobacterium avium, Mycobacterium bovis, Mycobacterium diphtheriae, Mycobacterium intracellulare, Mycobacterium leprae, Mycobacterium lepraemurium, Mycobacterium phlei, Mycobacterium smegmatis, Mycobacterium* spp., *Mycobacterium tuberculosis, Mycoplasma, Mycoplasma fermentans, Mycoplasma genitalium, Mycoplasma hominis, Mycoplasma penetrans, Mycoplasma pneumoniae, Mycoplasma* spp., *Neisseria, Neisseria gonorrhoeae, Neisseria meningitidis, Neisseria* spp., *Nocardia* spp., *Pasteurella, Pasteurella multocida, Pasteurella* spp., *Pasteurella tularensis, Peptostreptococcus, Porphyromonas gingivalis, Prevotella melaninogenica* (previously called *Bacteroides melaninogenicus*), *Proteus* spp., *Pseudomonas aeruginosa, Pseudomonas* spp., *Rhizobium radiobacter, Rickettsia, Rickettsia prowazekii, Rickettsia psittaci, Rickettsia quintana, Rickettsia rickettsia, Rickettsia* spp., *Rickettsia trachomae, Rochalimaea, Rochalimaea henselae, Rochalimaea quintana, Rothia dentocariosa, Salmonella, Salmonella enteritidis, Salmonella* spp., *Salmonella typhi, Salmonella typhimurium, Serratia marcescens, Shigella dysenteriae, Shigella* spp., *Spirillum volutans, Staphylococcus, Staphylococcus aureus, Staphylococcus epidermidis, Staphylococcus* spp., *Stenotrophomonas maltophilia, Stenotrophomonas* spp., *Streptococcus, Streptococcus agalactiae, Streptococcus avium, Streptococcus bovis, Streptococcus cricetus, Streptococcus faceium, Streptococcus faecalis, Streptococcus ferus, Streptococcus gallinarum, Streptococcus lactis, Streptococcus minor, Streptococcus mitis, Streptococcus mutans, Streptococcus oxalis, Streptococcus pneumoniae, Streptococcus pyogenes, Streptococcus rattus, Streptococcus salivarius, Streptococcus sanguis, Streptococcus sobrinus, Streptococcus* spp., *Treponema, Treponema denticola, Treponema pallidum, Treponema* spp., *Ureaplasma* spp., *Vibrio, Vibrio cholerae, Vibrio comma, Vibrio parahaemolyticus, Vibrio* spp., *Vibrio vulnificus, viridans streptococci, Wolbachia, Yersinia, Yersinia enterocolitica, Yersinia pestis, Yersinia pseudotuberculosis*, and *Yersinia* spp.

The microorganism may be a fungus. Examples of fungi include and are not limited to *Aspergillus* spp., *Blastomyces* spp., *Candida* spp., *Cladosporium, Coccidioides* spp., *Cryptococcus* spp., *Exserohilum, fusarium, Histoplasma* spp., *Issatchenkia* spp., *mucormycetes, Pneumocystis* spp., ringworm, *scedosporium, Sporothrix*, and *Stachybotrys* spp.

The microorganism may be a protozoan. Examples of protozoan include and are not limited to *Entamoeba histolytica, Plasmodium* spp., *Giardia lamblia*, and *Trypanosoma brucei*.

Exemplary Antimicrobials

When the microorganism is a bacterium, exemplary antimicrobials include Amikacin, Aminoglycoside, Aminoglycoside amoxicillin, Aminoglycosides, Amoxicillin, Amoxicillin/clavulanate, Ampicillin, Ampicillin/sulbactam, Antitoxin, Arsphenamine, Azithromycin, Azlocillin, Aztreonam, β-lactam, Bacitracin, Capreomycin, Carbapenems, Carbenicillin, Cefaclor, Cefadroxil, Cefalexin, Cefalothin, Cefalotin, Cefamandole, Cefazolin, Cefdinir, Cefditoren, Cefepime, Cefixime, Cefoperazone, Cefotaxime, Cefoxitin, Cefpodoxime, Cefprozil, Ceftaroline, Ceftaroline fosamil, Ceftazidime, Ceftibuten, Ceftizoxime, Ceftobiprole, Ceftriaxone, Cefuroxime, Cephalosporin, Chloramphenicol, Chloramphenicol (Bs), Ciprofloxacin, Clarithromycin, Clindamycin, Clofazimine, Cloxacillin, Colistin, Co-trimoxazole, Cycloserine, Dalbavancin, Dapsone, Daptomycin, Demeclocycline, Dicloxacillin, Dirithromycin, Doripenem, Doxycycline, Enoxacin, Ertapenem, Erythromycin, Ethambutol, Ethambutol (Bs), Ethionamide, Flucloxacillin, Fluoroquinolone, Fluoroquinolones, Fosfomycin, Furazolidone, Fusidic acid, Gatifloxacin, Geldanamycin, Gemifloxacin, Gentamicin, Grepafloxacin, Herbimycin, Imipenem/Cilastatin, Isoniazid, Kanamycin, Levofloxacin, Lincomycin, Linezolid, Lomefloxacin, Loracarbef, Macrolides, Mafenide, Meropenem, Methicillin, Metronidazole, Mezlocillin, Minocycline, Moxifloxacin, Mupirocin, Nafcillin, Nafcillin, Nalidixic acid, Neomycin, Netilmicin, Nitrofurantoin (Bs), Norfloxacin, Ofloxacin, Oritavancin, Oxacillin, Oxytetracycline, Paromomycin, Penicillin, Penicillin G, Penicillin V, Piperacillin, Piperacillin/tazobactam, Platensimycin, Polymyxin B, Posizolid, Pyrazinamide, Quinupristin/Dalfopristin, Radezolid, Raxibacumab, Rifabutin, Rifampicin, Rifampin, Rifapentine, Rifaximin, Roxithromycin, Silver sulfadiazine, Sparfloxacin, Spectinomycin, Spectinomycin (Bs), Spiramycin, Streptogramins, Streptomycin, Sulbactam, Sulfacetamide, Sulfadiazine, Sulfadimethoxine, Sulfamethizole, Sulfamethoxazole, Sulfanilimide, Sulfasalazine, Sulfisoxazole, Sulfonamidochrysoidine, Tedizolid, Teicoplanin, Teixobactin, Telavancin, Telithromycin, Temafloxacin, Temocillin, Tetracycline, Thiamphenicol, ticarcillin, Ticarcillin/clavulanate, Ticarcillin/clavulanic acid, Tigecycline, Tigecycline (Bs), Tinidazole, TMP/SMX, Tobramycin, Torezolid, Trimethoprim (Bs), Trimethoprim-Sulfamethoxazole, Troleandomycin, Trovafloxacin, Vancomycin, and generics thereof or a variant thereof.

Antimicrobials whose interactions with the microorganism affect and are affected by the negative charges on the microorganism surface include: polycationic aminoglycosides, which upon binding the cell surface displace $Mg^{2+}$ ions, which bridge lipid membrane components, thereby disrupting the outer membrane and enhancing drug uptake; cationic polymyxins (colistin and polymyxin B), whose binding to the microorganism cell is also dependent on the membrane's negative charge and for which both mutational and plasmid-mediated resistance occurs by reducing membrane negative charge; and daptomycin, a lipopeptide that resembles host innate immune response cationic antimicrobial peptides and requires $Ca^{2+}$ and phosphatidyl glycerol for its membrane-disrupting mechanism of action and for which resistance can also involve alteration in cell surface charge.

When the microorganism is a fungus, exemplary antimicrobials include 5-fluorocytosine, Abafungin, Albaconazole, Allylamines, Amphotericin B, Ancobon, Anidulafungin, Azole, Balsam of Peru, Benzoic acid, Bifonazole, Butoconazole, Candicidin, Caspofungin, Ciclopirox, Clotrimazole, Cresemba, Crystal violet, Diflucan, Echinocandins, Econazole, Efinaconazole, Epoxiconazole, Fenticonazole, Filipin, Fluconazole, Flucytosine, Grifulvin V, Griseofulvin, Gris-Peg, Haloprogin, Hamycin, Imidazoles, Isavuconazole, isavuconazonium, Isoconazole, Itraconazole, Ketoconazole, Lamisil, Luliconazole, Micafungin, Miconazole, Natamycin, Noxafil, Nystatin, Omoconazole, Onmel, Oravig, Oxiconazole, Posaconazole, Propiconazole, Ravuconazole, Rimocidin, Sertaconazole, Sporanox, Sulconazole, Terbinafine, Terconazole, Thiazoles, Thiocarbamate antifungal, Tioconazole, Tolnaftate, Triazoles, Undecylenic acid, Vfend, Voriconazole, and generics thereof or a variant thereof.

When the microorganism is a protozoan, exemplary antimicrobials include 8-Aminoquinoline, Acetarsol, Agents against amoebozoa, Ailanthone, Amodiaquine, Amphotericin B, Amprolium, Antitrichomonal agent, Aplasmomycin, Arsthinol, Artelinic acid, Artemether, Artemether/lumefantrine, Artemisinin, Artemotil, Arterolane, Artesunate, Artesunate/amodiaquine, Atovaquone, Atovaquone/proguanil, Azanidazole, Azithromycin, Benznidazole, Broxyquinoline, Buparvaquone, Carbarsone, Carnidazole, Chiniofon, Chloroquine, Chlorproguanil, Chlorproguanil/dapsone, Chlorproguanil/dapsone/artesunate, Chlorquinaldol, Chromalveolate antiparasitics, Cinchona, Cipargamin, Clazuril, Clefamide, Clioquinol, Coccidiostat, Codinaeopsin, Cotrifazid, Cryptolepine, Cycloguanil, Dehydroemetine, Difetarsone, Dihydroartemisinin, Diloxanide, Diminazen, Disulfiram, Doxycycline, Eflornithine, ELQ-300, Emetine, Etofamide, Excavata antiparasitics, Fumagillin, Furazolidone, Glycobiarsol, GNF6702, Halofantrine, Hydroxychloroquine, Imidocarb, Ipronidazole, Jesuit's bark, KAF156, Lumefantrine, Maduramicin, Mefloquine, Megazol, Meglumine antimoniate, Melarsoprol, Mepacrine, Metronidazole, Miltefosine, Neurolenin B, Nicarbazin, Nifurtimox, Nimorazole, Nitarsone, Nitidine, Nitrofural, Olivacine, Ornidazole, Oroidin, Pamaquine, Paromomycin, Pentamidine, Pentavalent antimonial, Phanquinone, Phenamidine, Piperaquine, Primaquine, Proguanil, Project 523, Propenidazole, Pyrimethamine, Pyronaridine, Quinfamide, Quinine, Ronidazole, Schedula Romana, SCYX-7158, Secnidazole, Semapimod, Sodium stibogluconate, Spiroindolone, Sulfadoxine, Sulfadoxine-Pyrimethamine, Sulfalene, Suramin, Tafenoquine, Teclozan, Tenonitrozole, Tilbroquinol, Tinidazole, Trimetrexate, Trypanocidal agent, Warburg's tincture, and generics thereof or a variant thereof.

An antimicrobial may be a drug that operates by a mechanism similar to a herein-recited drug.

Other antimicrobial drugs known in the art may be used in the present invention.

Liquid Suspensions

A liquid suspension of microorganisms may by agitated using mechanical, acoustic, and/or magnetic agitation. Examples of mechanical agitation include shaking or rocking and/or use of stir bars, stir paddles, stir blades, and/or stir propellers or impellers.

The microorganism separation is performed by centrifugation (e.g., with a g-force >500×g), magnetic separation, filtration (e.g., via a filter having pores smaller than or equal to 0.45 microns, and preferably smaller than or equal to 0.2 microns), electrophoresis, dielectrophoresis, precipitation, agglutination, or any combination thereof.

The liquid may include a growth media, such as cation-adjusted Mueller Hinton broth. This media may contain one or more additives, known to those skilled in the art to promote microorganism growth, and stability. In addition to different antimicrobials, different test wells may contain one or more additives known to improve AST accuracy for specific antimicrobials. For example, additional sodium chloride may be added to tests comprising oxacillin and additional calcium may be added to tests comprising daptomycin.

Cartridges

The type of cartridge is not limited. A cartridge is a container that is capable of holding and allowing growth of a liquid suspension of microorganisms. Non-limited examples of a cartridge include a culture flask, a culture dish, a petri dish, a bioassay dish, a culture tube, a test tube, a microfuge tube, a bottle, a microwell plate, a multiwell plate, a microtiter plate, a microplate. The cartridge may contain one chamber. The cartridge may include a plurality of chambers each chamber being a space capable of holding a liquid suspension in physical isolation from another space; an example of a chamber is a well in a multiwall plate. The cartridge may comprise 1, 2, 3, 4, 5, 6, 7, 8, 9, 10, 11, 12, 24, 48, 96, 192, 384, 1536, or more chambers, and any number of chambers in between.

Optical Device

Any optical device (e.g., microscope, microplate reader) with a number of varying features is capable of detecting a signal is useful in the present invention. For instance: broad spectrum lamp (e.g., xenon), narrow spectrum lamps, laser, LED, multi-photon, confocal or total-internal reflection illumination can be used for excitation. Cameras (single or multiple), single or arrays (1D or 2D) of photodiodes, avalanche photodiodes, CMOS or CCD sensors, solid-state photomultipliers (e.g. silicon photomultipliers), and/or Photomultiplier tube (single or multiple) with either filter-based or grating-based spectral resolution (one or more spectrally resolved emission wavelengths) are possible on the detection side.

Kits

The terms "kits" and "systems," as used herein in the present invention, are intended to refer to such things as combinations of multiple signaling agents with one or more other types of elements or components (e.g., other types of biochemical reagents, signal detection reagents, controls (i.e., positive and negative controls, e.g., chemically sensitive/resistant microorganisms), separation means (e.g., filters and magnetic beads), containers, packages such as packaging intended for commercial sale, substrates/cartridges to which microorganism suspensions can be cultured, processed, or contained, electronic hardware components, and software recorded on a non-transitory processor-readable medium).

Another aspect of the present invention is a kit for determining antimicrobial susceptibility of microorganisms. The kit includes a signaling agent capable of binding to a surface of the intact microorganisms of interest; a solution for incubating a sample containing microorganisms; and one or more reagents for generating signals from the signaling agent.

In embodiments, the signaling agent is associated with one or more binding moieties capable of binding directly or indirectly to the intact microorganisms of interest.

In embodiments, the one or more binding moieties are selected from antibodies, lectins, natural and/or synthetic peptides, synthetic and/or natural ligands, synthetic and/or natural polymers, synthetic and/or natural glycopolymers, carbohydrade-binding proteins and/or polymers, glycoprotein-binding proteins and/or polymers, charged small molecules, other proteins, bacteriophages, and/or aptamers.

In embodiments, the one or more binding moieties may be a polyclonal and/or monoclonal antibody.

In embodiments, the one or more binding moieties may be a synthetic and/or natural ligand and/or peptide. The ligand and/or peptide may be selected from bis(zinc-dipicolylamine), TAT peptide, serine proteases, cathelicidins, cationic dextrins, cationic cyclodextrins, salicylic acid, lysine, and a combinations thereof.

In embodiments, the one or more binding moieties may be a synthetic and/or natural polymer and/or glycopolymer. The natural and/or synthetic polymer may be amylopectin, Poly (N-[3-(dimethylamino)propyl] methacrylamide), poly(ethyleneimine), poly-L-lysine, poly[2-(N,N-dimethylamino) ethyl methacrylate], and combinations thereof. The natural and/or synthetic polymer and/or glycopolymer my include moieties including, but not limited to, chitosan, gelatin, dextran, trehalose, cellulose, mannose, cationic dextrans and cyclodextrans, or combinations thereof including, but not limited to, co-block, graft, and alternating polymers.

In embodiments, the one or more binding moieties may include a glycoprotein selected from mannose-binding lectin, other lectins, annexins, and combinations thereof.

In embodiments, the one or more binding moieties may include two or more binding moieties.

In embodiments, the one or more binding moieties may bind directly or indirectly to one or more biomolecules present on the microorganism surface. Exemplary biomolecules include peptidoglycans, mureins, mannoproteins, porins, beta-glucans, chitin, glycoproteins, polysaccharides, lipopolysaccharides, lipooligosaccharides, lipoproteins, endotoxins, lipoteichoic acids, teichoic acids, lipid A, carbohydrade binding domains, efflux pumps, other cell-wall and/or cell-membrane associated proteins, other anionic phospholipids, and a combination thereof.

In embodiments, the binding moiety is a nanoparticle.

In embodiments, the binding moiety is a bacteriophage.

In embodiments, the one or more binding moieties may bind to one or more biomolecules specifically.

In embodiments, the one or more binding moieties may bind to one or more species-specific biomolecules.

In embodiments, the one or more binding moieties may bind to the microorganisms non-specifically, e.g., via a non-covalent interaction and via forming a covalent bond.

In embodiments, the kit further includes magnetic beads to magnetically separate the microorganisms from the supernatant.

In embodiments, the magnetic beads are associated with one or more binding moieties that bind to microorganisms. The one or more binding moieties associated with the magnetic beads may identical to those associated with the signaling agents. The one or more binding moieties associated with the magnetic beads may be different than those associated with the signaling agents.

In embodiments, the magnetic beads have diameters ranging between 20 nm to 20 microns.

In embodiments, the kit further includes one or more ions or small molecules to enhance the binding between the binding moieties and the microorganism.

In embodiments, the solution comprises <0.15 M salt.

In embodiments, the kit further includes a microorganism binding agent, and wherein the binding moiety binds to the microorganisms indirectly via the microorganism binding agent. The binding moiety may be conjugated to streptavidin, neutravidin, or avidin and the microorganism binding agent may be biotinylated. The binding moiety may be an antibody that binds to a species specific Fc domain and the microorganism binding agent may be an antibody capable of binding to the microorganisms with the species specific Fc domain.

In embodiments, the signaling agent may include one or more of a chemiluminophore, a catalyst, or an enzyme. The enzyme may be at least one of horseradish peroxidase, alkaline phosphatase, acetyl cholinesterase, glucose oxidase, beta-D-galactosidase, beta-lactamase, and combinations thereof. The catalyst may be an organometallic compound.

In embodiments, the signaling agent is provided in a form of a nanoparticle, e.g., the signaling agent is encapsulated within a nanoparticle. The nanoparticle may be dissociable, which may include a metal oxide; the metal oxide may be or include iron oxide, cesium oxide, and/or cerium oxide.

In embodiments, zero, one, or two washes are performed prior to determining signal levels.

In embodiments, zero, one, or two washes are performed prior to addition of the signaling agents.

In embodiments, the kit further includes a developer reagent to produce a measurable signal.

In embodiments, the one or more reagents include reagents for a catalytic reaction and a reagent that stops the catalytic reaction.

In embodiments, the kit further comprises a device for measuring signal, e.g., an optical and/or electrical signal. The optical measurement may be fluorescent, time-resolved fluorescent, absorbent, and/or luminescent.

In embodiments, the kit further comprises a multiwell plate, e.g., a 24-well, 96-well, 192-well, or 384-well plate.

In embodiments, the further contains instructions for using the kit to perform a herein-disclosed method. The kit may additionally contain instructions for performing steps conducted prior to or subsequent to one or more methods as described herein.

In one embodiment, kits are provided which contain the necessary reagents to carry out one or more methods as described herein or reagents necessary to carry out steps prior to or subsequent to one or more methods as described herein.

Treatment Methods

As used herein, the terms "treat," "treating," "treatment," and the like refer to reducing or ameliorating a disorder and/or a symptom associated therewith. It will be appreciated that, although not precluded, treating a disorder or condition does not require that the disorder, condition or symptoms associated therewith be completely eliminated. Treating may include a health care professional or diagnostic scientist making a recommendation to a subject for a desired course of action or treatment regimen, e.g., a prescription.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

The term "methods of treating" includes methods of managing, and when used in connection with the infections microbial organism or infection, includes the amelioration, elimination, reduction, prevention, or other relief or management from the detrimental effects of the infections microbe.

As used herein, the terms "drug", "medication", "therapeutic", "active agent", "therapeutic compound", "composition", or "compound" are used interchangeably and refer to any chemical entity, pharmaceutical, drug, biological, botanical, and the like that can be used to treat or prevent a disease, illness, condition, or disorder of bodily function. A drug may comprise both known and potentially therapeutic compounds. A drug may be determined to be therapeutic by screening using the screening known to those having ordinary skill in the art. A "known therapeutic compound", "drug", or "medication" refers to a therapeutic compound that has been shown (e.g., through animal trials or prior experience with administration to humans) to be effective in such treatment. A "therapeutic regimen" relates to a treatment comprising a "drug", "medication", "therapeutic", "active agent", "therapeutic compound", "composition", or "compound" as disclosed herein and/or a treatment comprising behavioral modification by the subject and/or a treatment comprising a surgical means.

An antimicrobial, e.g., an antibiotic, is an agent capable of killing a microorganism or inhibiting the growth of a microorganism.

Signaling Agents and Chemical Attachment

In embodiments, the invention features a signaling agent capable of binding to the surface of a microorganism. In embodiments, said binding is non-specific. In embodiments, said binding is specific.

In embodiments, a signaling agent is present during an incubating step of a method described herein. In embodiments, a signaling agent is present after an incubating step of a method described herein.

In embodiments, binding comprises the formation of a covalent bond. In embodiments, a signaling agent is capable of binding to the surface of a microorganism, wherein said binding comprises the formation of a covalent bond. In embodiments, a method as described herein results in the formation of a covalent bond between a group on a microorganism surface (e.g., via a reactive group such as an electrophilic or nucleophilic group as described herein) and a signaling agent as described herein. In embodiments, a signaling agent has formed a covalent bond to the surface of a microorganism.

In embodiments, binding comprises the formation of a non-covalent interaction. In embodiments, a signaling agent is capable of binding to the surface of a microorganism, wherein said binding comprises the formation of a non-covalent interaction. In embodiments, a method as described herein results in the formation of non-covalent interaction between a group on a microorganism surface (e.g., via a reactive group such as an electrophilic or nucleophilic group as described herein) and a signaling agent as described herein. In embodiments, a signaling agent has formed a non-covalent interaction with the surface of a microorganism.

In embodiments, a non-covalent interaction comprises: ionic interaction, ion-ion interaction, dipole-dipole interaction, ion-dipole interaction, electrostatic interaction, London dispersion, van der Waals interaction, hydrogen bonding, $\pi$-$\pi$ interaction, hydrophobic interaction, or any combination thereof. In embodiments, a non-covalent interaction is: ionic interaction, ion-ion interaction, dipole-dipole interaction, ion-dipole interaction, electrostatic interaction, London dispersion, van der Waals interaction, hydrogen bonding, $\pi$-$\pi$ interaction, hydrophobic interaction, or any combination thereof.

In embodiments, a non-covalent interaction comprises ionic interactions, van der Waals interactions, hydrophobic interactions, $\pi$-$\pi$ interactions, or hydrogen bonding, or any combination thereof. In embodiments, a non-covalent interaction comprises ionic interaction, van der Waals interaction, hydrogen bonding, or $\pi$-$\pi$ interaction, or any combination thereof.

In embodiments, a signaling agent capable of binding to a microorganism's surface comprises a group (e.g., a chemical or biochemical group) capable of binding microorganism membranes, walls, proteins, organelles, saccharides, lipids, cell envelope, or nucleic acids, or any combination thereof. In embodiments, a signaling agent capable of binding to a microorganism's surface comprises a chemical group (e.g., a nucleophilic group or an electrophilic group) capable of binding microorganism membranes, walls, proteins, organelles, saccharides, lipids, cell envelope, or nucleic acids, or any combination thereof. In embodiments, a signaling agent capable of binding to a microorganism's surface comprises a biochemical group capable of binding microorganism membranes, walls, proteins, organelles, saccharides, lipids, cell envelope, or nucleic acids, or any combination thereof.

In embodiments, the surface may include a biomolecule to which the signaling agent binds or associates. Exemplary biomolecules include peptidoglycans, mureins, mannoproteins, porins, beta-glucans, chitin, glycoproteins, polysaccharides, lipopolysaccharides, lipooligosaccharides, lipoproteins, endotoxins, lipoteichoic acids, teichoic acids, lipid A, carbohydrate binding domains, efflux pumps, other cell-wall and/or cell-membrane associated proteins, other anionic phospholipids, and a combination thereof.

In embodiments, a signaling agent capable of binding to a microorganism's surface comprises a biochemical group capable of binding microorganism membranes, walls, proteins, organelles, saccharides, lipids, cell envelope, or nucleic acids, or any combination thereof.

In embodiments, a signaling agent capable of binding to a microorganism's surface comprises a chemical group (e.g., a nucleophilic or electrophilic functional group) capable of binding microorganism membranes, walls, proteins, organelles, saccharides, lipids, cell envelope, or nucleic acids, or any combination thereof. In embodiments, said chemical group is a nucleophilic functional group. In embodiments, said chemical group is an electrophilic functional group.

In embodiments, a signaling agent is a biochemical signaling agent. In embodiments, a biochemical signaling agent comprises a biomolecule such as an antibody, ligand, protein, aptamer, ss-DNA, ss-RNA, or ss-PNA).

In embodiments, a signaling agent is a chemical signaling agent. In embodiments, a chemical signaling agent is a chemical compound (e.g., a synthetic chemical compound). In embodiments, a chemical signaling agent does not comprise a biomolecule such as an antibody, ligand, protein, aptamer, ss-DNA, ss-RNA, or ss-PNA).

In embodiments, a signaling agent capable of binding to a microorganism's surface comprises
a linker group L; and
an amplifier group (e.g., an amplifier group 104 that is a chemical or biochemical amplifier).

In embodiments, an amplifier group is an amplifier group 104, which is a chemical or biochemical amplifier. In embodiments, an amplifier group 104 is a chemical amplifier. In embodiments, an amplifier group 104 is a biochemical amplifier.

In embodiments, a signaling agent is a chemical compound. In embodiments, a chemical compound comprises a chemical amplifier group such as those described herein).

In embodiments, a linker group L comprises the conserved (Fc) region of an antibody.

In embodiments, a linker group L is capable of forming a covalent bond to an amplifier group (e.g., an amplifier group 104 that is a chemical or biochemical amplifier).

In embodiments, a linker group L forms a covalent bond to a signal amplifier group (e.g., an amplifier group 104 that is a chemical or biochemical amplifier).

In embodiments, a linker group L is capable of forming one or more non-covalent interactions to an amplifier group (e.g., an amplifier group 104 that is a chemical or biochemical amplifier).

In embodiments, a linker group L forms one or more non-covalent interactions to an amplifier group (e.g., an amplifier group 104 that is a chemical or biochemical amplifier).

In embodiments, a linker group L comprises a group (e.g., a chemical or biochemical group) capable of binding a microorganism surface. In embodiments, a linker group L comprises a group (e.g., a chemical or biochemical group) that binds a microorganism surface.

In embodiments, a linker group L comprises a group (e.g., a chemical or biochemical group) that is capable of forming a covalent bond to a microorganism's surface. In embodiments, a linker group L comprises a group (e.g., a chemical or biochemical group) that forms a covalent bond to a microorganism's surface.

In embodiments, a linker group L comprises a group (e.g., a chemical or biochemical group) that is capable of forming one or more non-covalent interactions with a microorganism's surface. In embodiments, a linker group L comprises a group (e.g., a chemical or biochemical group) that forms one or more non-covalent interactions with a microorganism's surface.

In embodiments, a linker group L comprises a chemical moiety 101, wherein said chemical moiety is capable of forming a non-covalent interaction with the surface of a microorganism. In embodiments, a linker group L comprises a chemical moiety 101, wherein said chemical moiety is capable of forming a covalent bond with the surface of a microorganism. In embodiments, a linker group L comprises a chemical moiety 101, wherein said chemical moiety forms a non-covalent interaction with the surface of a microorganism. In embodiments, a linker group L comprises a chemical moiety 101, wherein said chemical moiety forms a covalent bond with the surface of a microorganism.

In embodiments, a linker group L comprises a spacer moiety 102. In embodiments, spacer moiety 102 is covalently attached to chemical moiety 101 and/or to chemical moiety 103. In embodiments, spacer moiety 102 is covalently attached to chemical moiety 101. In embodiments, spacer moiety 102 is covalently attached to chemical moiety 103. In embodiments, spacer moiety 102 is covalently attached to chemical moiety 101 and to chemical moiety 103. In embodiments, spacer moiety 102 forms a non-covalent interaction with chemical moiety 101 and/or with chemical moiety 103. In embodiments, spacer moiety 102 forms a non-covalent interaction with chemical moiety 101. In embodiments, spacer moiety 102 forms a non-covalent interaction with chemical moiety 103. In embodiments, spacer moiety 102 forms a non-covalent interaction with chemical moiety 101 and with chemical moiety 103.

In embodiments, a linker group L comprises a chemical moiety 103, wherein said chemical moiety is capable of forming a covalent bond to an amplifier group (e.g., an amplifier group 104 that is a chemical or biochemical amplifier). In embodiments, a linker group L comprises a chemical moiety 103, wherein said chemical moiety has formed a covalent bond to an amplifier group (e.g., an amplifier group 104 that is a chemical or biochemical amplifier). In embodiments, a linker group L comprises a chemical moiety 103, wherein said chemical moiety is capable of forming a non-covalent interaction with an amplifier group (e.g., an amplifier group 104 that is a chemical or biochemical amplifier). In embodiments, a linker group L comprises a chemical moiety 103, wherein said chemical moiety has formed a non-covalent interaction with an amplifier group (e.g., an amplifier group 104 that is a chemical or biochemical amplifier).

In embodiments, a signaling agent is a chemical compound comprising a linker group L that comprises:

a chemical moiety 101, wherein said chemical moiety is capable of forming a covalent bond or a non-covalent interaction with the surface of the microorganisms;

a spacer moiety 102, wherein spacer moiety is covalently attached to chemical moiety 101 and to chemical moiety 103; and a chemical moiety 103, wherein said chemical moiety has formed or can form a covalent bond to an amplifier group 104 that is a chemical or biochemical amplifier.

In embodiments, a signaling agent is a chemical compound comprising a linker group L that comprises:

a chemical moiety 101, wherein said chemical moiety is capable of forming a covalent bond or a non-covalent interaction with the surface of a microorganism;

a spacer moiety 102, wherein spacer moiety is covalently attached to chemical moiety 101 and to chemical moiety 103; and a chemical moiety 103, wherein said chemical moiety has formed or can form a non-covalent interaction with an amplifier group 104 that is a chemical or biochemical amplifier.

In embodiments, a linker group comprises one chemical moiety 101. In embodiments, a linker group comprises more than one chemical moiety 101 (e.g., a linker group comprises 1, 2, 3, 4, 5, or 6 chemical moieties 101).

In embodiments, a linker group comprises one spacer moiety 102. In embodiments, a linker group comprises more than one spacer moiety 102 (e.g., a linker group comprises 1, 2, 3, 4, 5, or 6 spacer moieties 102).

In embodiments, a linker group comprises one chemical moiety 103. In embodiments, a linker group comprises more than one chemical moiety 103 (e.g., a linker group comprises 1, 2, 3, 4, 5, or 6 chemical moieties 103).

In embodiments, a linker group comprises: one chemical moiety 101, one spacer moiety 102, and one chemical moiety 103. In embodiments, a linker group consists of: one chemical moiety 101, one spacer moiety 102, and one chemical moiety 103.

In embodiments, a linker group has the structure of substructure (I):

-101-102-103-    (I)

wherein

"101" represents a chemical moiety 101;

"102" represents a spacer moiety 102; and

"103" represents a chemical moiety 103.

In embodiments, a chemical moiety 101 is capable of forming a covalent bond with the surface of a microorganism.

In embodiments, a chemical moiety 101 is capable of forming a covalent bond with the surface of a microorganism in the presence of one or more agents that promote coupling (also referred to herein as coupling agents).

In embodiments, agents that promote coupling include glutaraldehyde, formaldehyde, paraformaldehyde, 1-ethyl-3-(3-dimethylaminopropyl)carbodiimide (EDC), N,N'-dicyclohexylcarbodiimide (DCC), N-cyclohexyl-N'-(2-morpholinoethyl)carbodiimide-methyl-p-toluenesulfonate (CMC), diisopropylcarbodiimide (DIC), (1-[bis(dimethylamino)methylene]-1H-1,2,3-triazolo[4,5-b]pyridinium 3-oxid hexafluorophosphate) (HATU), Woodward's Reagent, N,N'-carbonyl diimidazole, N-hydroysuccinimide (NHS), or N-hydroxysulfosuccinimide (sulfo-NHS), or any combination thereof.

In embodiments, agents that promote coupling include aldehydes, acrylates, amides, imides, anhydrides, chlorotriazines, epoxides, isocyanates, isothiocyanates, organic acids, monomers, polymers, silanes, or silcates, or any combination thereof.

In embodiments, agents that promote coupling include a carbodiimide, a phosphonium salt, or an ammonium salt, or any combination thereof.

In embodiments agents that promote coupling include glutaraldehyde, N-(3-dimethylaminopropyl)-N'-ethylcarbonate (EDC), (1-[bis(dimethylamino)methylene]-1H-1,2,3-triazolo[4,5-b]pyridinium 3-oxid hexafluorophosphate) (HATU), (O-benzotriazol-1-yl-N,N,N,N-tetramethyluronium hexafluorophosphate) (HBTU), N-hydroxysuccinimide (NHS), N,N'-dicyclohexylcarbodiimide (DCC), diisopropylcarbodiimide (DIC), hydroxy-3,4-dihydro-4-oxo-1,2,3-benzotriazine (HOOBt), hydroxybenzotriazole (HOBT), 1-hydroxy-7-azabenzotriazole (HOAt), (N-(3-dimethylaminopropyl)-N'-ethylcarbodiimide (EDAC), 4-(N,N-dimethylamino)pyridine (DMAP), benzotriazol-1-yloxy-tris(dimethylamino)-phosphonium hexafluorophosphate (BOP), benzotriazol-1-yloxy-tripyrrolidino-phosphonium hexafluorophosphate (PyBOP), bromo-tripyrrolidino-phosphonium hexafluorophosphate (PyBrOP), 7-aza-benzotriazol-1-yloxy-tripyrrolidinophosphonium hexafluorophosphate (PyAOP), ethyl cyano(hydroxyimino)acetato-O2)-tri-(1-pyrrolidinyl)-phosphonium hexafluorophosphate (PyOxim), 3-(diethoxy-phosphoryloxy)-1,2,3-benzo[d] triazin-4(3H)-one (DEPBT), 2-(6-chloro-1H-benzotriazol-1-yl)-N,N,N',N'-tetramethylaminium hexafluorophosphate (HCTU), N-[(5-chloro-1H-benzotriazol-1-yl)-dimethylamino-morpholino]-uronium hexafluorophosphate N-oxide (HDMC), 1-[1-(cyano-2-ethoxy-2-oxoethylideneaminooxy)-dimethylamino-morpholino]-uronium hexafluorophosphate (COMU), 2-(1-oxy-pyridin-2-yl)-1,1,3,3-tetramethylisothiouronium tetrafluoroborate (TOTT), tetramethylfluoroformamidinium hexafluorophosphate (TFFH), N-Ethoxycarbonyl-2-ethoxy-1,2-dihydroquinoline (EEDQ), 2-propanephosphonic acid anhydride (PPA), triphosgene, 1,1'-carbonyldiimidazole (CDI), [(6-nitrobenzotriazol-1-yl)oxy]tris(pyrrolidino)phosphonium hexafluorophosphate (PyNOP), [[6-(trifluoromethyl)benzotriazol-1-yl]oxy]tris(pyrroli-dino)phosphonium hexafluorophosphate (PyFOP), [[4-nitro-6-(trifluoromethyl)benzotriazol-1-yl]oxy]tris(pyrrolidino)phosphonium hexafluorophosphate (PyNFOP), [(6-nitrobenzo-triazol-1-yl)oxy]tris(dimethyl-amino)phosphonium hexafluorophosphate (NOP), 1-β-naphthalenesulfonyloxy benzotriazole (NSBt), 1-β-naphthalenesulfonyloxy-6-nitrobenzotriazole (N-NSBt), tetramethylfluoroformamidinium hexafluorophosphate (TFFH), bis(tetramethylene)fluoroformamidinium hexafluorophosphate (BTFFH), 1,3-dimethyl-2-fluoro-4,5-dihydro-1H-imidazolium hexafluorophosphate (DFIH), Cyanuric chloride (CC), or 2,4-dichloro-6-methoxy-1,3,5-triazine (DCMT), and 2-chloro-4,6-dimethoxy-1,3,5-triazine (CDMT), or any combination thereof.

In embodiments, agents that promote coupling include EDC, HATU, HBTU, NHS, DCC, HOBT, or PyBOP, or any combination thereof.

In embodiments, agents that promote coupling include EDC, DCC, CMC, DIC, or HATU, or any combination thereof.

In embodiments, agents that promote coupling include glutaraldehyde, formaldehyde, or paraformaldehyde, or any combination thereof.

In embodiments, a chemical moiety 101 is capable of forming a non-covalent interaction with the surface of a microorganism (e.g., any non-covalent interaction described herein). In embodiments, a non-covalent interaction comprises: ionic, ion-ion, dipole-dipole, ion-dipole, electrostatic, London dispersion, van der Waals, hydrogen bonding, or π-π, or any combination thereof.

In embodiments, a chemical moiety 101 is capable of forming a non-covalent interaction with the surface of a microorganism, wherein said non-covalent interaction comprises ionic interactions, van der Waals interactions, hydrophobic interactions, π-π interactions, or hydrogen bonding, or any combination thereof.

In embodiments, a chemical moiety 101 comprises a nucleophilic functional group. In embodiments, a chemical moiety 101 comprises a group formed from a nucleophilic functional group.

In embodiments, a nucleophilic functional group is: amino, amido, hydrazino, hydroxyamino, hydroxy, or thio. In embodiments, a nucleophilic functional group is: amino, hydrazino, hydroxyamino, or thio. In embodiments, a nucleophilic functional group comprises: amino, hydrazino, hydroxyamino, hydroxy, or thio. In embodiments, a nucleophilic functional group is carboxamide, N-hydroxycarboxamide, carboxyl hydrazide, or guanidino.

In embodiments, a nucleophilic functional group is —NH$_2$, —NHNH$_2$, —CONHOH, —CONHNH$_2$, —ONH$_2$, —OH, or —SH. In embodiments, a nucleophilic functional group is —NH$_2$, —NHNH$_2$, —CONHNH$_2$, or —ONH$_2$.

In embodiments, a chemical moiety 101 comprises an electrophilic functional group.

In embodiments, a chemical moiety 101 comprises a group formed from an electrophilic functional group.

In embodiments, an electrophilic functional group comprises an aldehyde, a ketone, a carboxylic acid, a carboxylic ester, a carboxylic acid halide (e.g., acetyl chloride), or a carboxylic acid anhydride (e.g., acetic anhydride).

In embodiments, an electrophilic functional group comprises an aldehyde, an α-halo ketone, a maleimide, a succinimide, a hydroxysuccinimide, an isothiocyanate, an isocyanate, an acyl azide, a sulfonyl chloride, a tosylate ester, a glyoxal, an epoxide, an oxirane, a carbonate, an imidoester, an anhydride, a fluorophenyl ester, a hydroxymethyl phosphine derivative, a carbonate, a haloacetyl, a chlorotriazine, a haloacetyl, an alkyl halide, an aziridine, or an acryloyl derivative. In embodiments, an electrophilic functional group is an aldehyde, an α-halo ketone, a maleimide, a succinimide, a hydroxysuccinimide, an isothiocyanate, an isocyanate, an acyl azide, a sulfonyl chloride, a tosylate ester, a glyoxal, an epoxide, an oxirane, a carbonate, an imidoester, an anhydride, a fluorophenyl ester, a hydroxymethyl phosphine derivative, a carbonate, a haloacetyl, a chlorotriazine, a haloacetyl, an alkyl halide, an aziridine, or an acryloyl derivative.

In embodiments, an electrophilic functional group comprises an aldehyde, an α-halo ketone, a maleimide, a succinimide, or a hydroxysuccinimide group.

In embodiments, an electrophilic functional group comprises —CHO, —C(O)CH$_2$I,

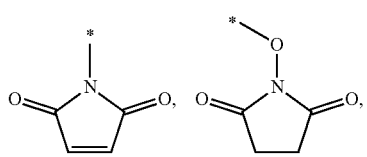

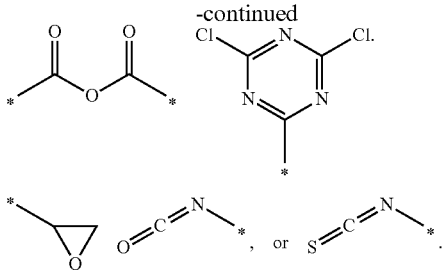

In embodiments, an electrophilic functional group comprises —CHO, —C(O)CH$_2$I,

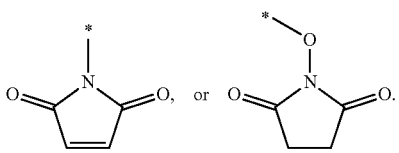

In embodiments, chemical moiety 101 comprises a group that is alkyl, alkenyl, alkynyl, phenyl, heteroaryl, haloalkyl, hydroxy, carbonyl, acyl halide, alkoxycarbonyl)oxy, carboxy, haloketone, alkoxy, alkoxyol (hemiacetal or) hemiketal, dialkoxy (e.g., ketal or acetal), trialkoxy(orthoether), carbamoyl, amino, ammonio, imino, imido, succinamido, maleidido, hydroxysuccinamido, biotin, D-Biotin, azido, azo, cyanate, isocyanato, nitroxy, cyano, isocyano, nitrosooxy, nitro, nitroso, oxime, sulfanyl, sulfinyl, sulfonyl, sulfino, sulfo, thiocyanato, isothiocyanato, thioyl, phosphate, or boronate.

In embodiments, spacer moiety 102 is hydrophobic. In embodiments, spacer moiety 102 is hydrophilic.

In embodiments, spacer moiety 102 is peptidic (e.g., derived from peptide linkages).

In embodiments, spacer moiety 102 comprises inorganic linkages. In embodiments, spacer moiety 102 comprises organic linkages. In embodiments, spacer moiety 102 comprises only organic linkages.

In embodiments, spacer moiety 102 is oligomeric. In embodiments, spacer moiety 102 is polymeric. In embodiments, spacer moiety 102 comprises segments (e.g., 1 to about 300, 1 to about 200, 1 to about 100, 1 to about 50, 1 to about 25, or 1 to about 10, or 1, 2, 3, 4, 5, 6, 7, 8, 9, or 10 segments) of methylene (—CH$_2$—), ethylene glycol (—CH$_2$CH$_2$O—), iminoethylene (—CH$_2$CH$_2$NH—), vinyl alcohol (—CH$_2$CHOH—)$_x$, lactic acid (—CH(CH$_3$)—C(O)—O—), acrylic acid (—CH$_2$CH$_2$(CO$_2$H)—), methacrylic acid (—CH$_2$C(CH$_3$)(CO$_2$H)—), or methyl methacrylate (—CH$_2$C(CH$_3$)(CO$_2$CH$_3$)—).

In embodiments, spacer moiety 102 comprises a segment that is

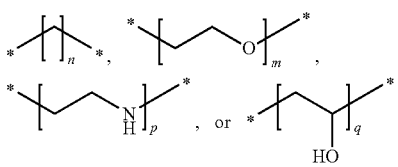

In embodiments, n, m, p, and q independently is an integer of 1 to about 300 (e.g., 1 to about 200, 1 to about 100, 1 to about 50, 1 to about 25, or 1 to about 10). In embodiments, each of n, m, p, and q is independently 1, 2, 3, 4, 5, 6, 7, 8, 9, or 10.

In embodiments, spacer moiety 102 comprises

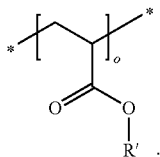

In embodiments, R' is independently hydrogen or a group that is $C_1$-$C_{12}$ alkyl, $C_2$-$C_{12}$ alkenyl, or $C_2$-$C_{12}$ alkynyl. In embodiments, o is an integer of 1 to about 300 (e.g., 1 to about 200, 1 to about 100, 1 to about 50, 1 to about 25, or 1 to about 10). In embodiments, o is independently 1, 2, 3, 4, 5, 6, 7, 8, 9, or 10.

In embodiments, spacer moiety 102 comprises

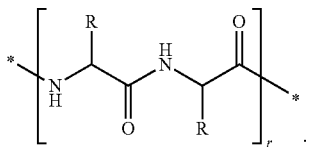

In embodiments, R is independently hydrogen or a group that is $C_1$-$C_{12}$ alkyl, $C_2$-$C_{12}$ alkenyl, or $C_2$-$C_{12}$ alkynyl. In embodiments, r is an integer of 1 to about 300 (e.g., 1 to about 200, 1 to about 100, 1 to about 50, 1 to about 25, or 1 to about 10). In embodiments, r is independently 1, 2, 3, 4, 5, 6, 7, 8, 9, or 10.

In embodiments, spacer moiety 102 comprises

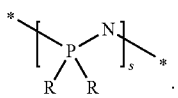

In embodiments, R is independently hydrogen or a group that is $C_1$-$C_{12}$ alkyl, $C_2$-$C_{12}$ alkenyl, or $C_2$-$C_{12}$ alkynyl. In embodiments, s is an integer of 1 to about 300 (e.g., 1 to about 200, 1 to about 100, 1 to about 50, 1 to about 25, or 1 to about 10). In embodiments, s is independently 1, 2, 3, 4, 5, 6, 7, 8, 9, or 10.

In embodiments, spacer moiety 102 comprises

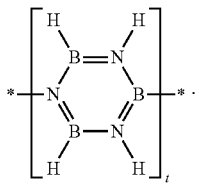

In embodiments, t is an integer of 1 to about 300 (e.g., 1 to about 200, 1 to about 100, 1 to about 50, 1 to about 25, or 1 to about 10). In embodiments, t is independently 1, 2, 3, 4, 5, 6, 7, 8, 9, or 10.

In embodiments, spacer moiety 102 comprises:

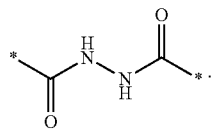 [SMILES: *C(=O)NNC(*)=O]

In embodiments, spacer moiety 102 is a polymer comprising repeating groups, comprising alkyl, alkoxy, ester, acrylic, amino, hydroxyl, or acyl hydrazine functional groups, or any combination thereof.

In embodiments, the spacer moiety 102 is:

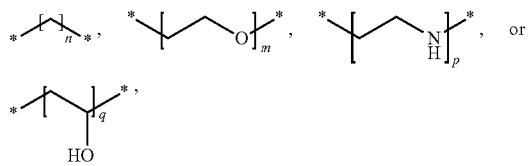

wherein n, m, p, and q are as defined herein

In embodiments, each of n, m, o, p, q, r, s, or t independently is an integer of 1 to 100, of 10 to 90, of 10 to 80, of 10 to 70, of 10 to 60, of 10 to 50, of 10 to 40, of 10 to 30, of 10 to 20, or of 1 to 10.

In embodiments, a chemical moiety 103 comprises a group that is a nucleophilic functional group.

In embodiments, a chemical moiety 103 comprises a group formed from a nucleophilic functional group.

In embodiments, a nucleophilic functional group is: amino, amido, hydrazino, hydroxyamino, hydroxy, or thio. In embodiments, a nucleophilic functional group is: amino, hydrazino, hydroxyamino, or thio.

In embodiments, a nucleophilic functional group comprises: amino, hydrazino, hydroxyamino, hydroxy, or thio. In embodiments, a nucleophilic functional group is carboxamide, N-hydroxycarboxamide, carboxyl hydrazide, or guanidino.

In embodiments, a nucleophilic functional group is —$NH_2$, —$NHNH_2$, —$CONHOH$, —$CONHNH_2$, —$ONH_2$, —OH, or —SH. In embodiments, a nucleophilic functional group is —$NH_2$, —$NHNH_2$, —$CONHNH_2$, or —$ONH_2$.

In embodiments, a chemical moiety 103 comprises a group that is a electrophilic functional group.

In embodiments, a chemical moiety 103 comprises a group formed from a electrophilic functional group.

In embodiments, an electrophilic functional group comprises an aldehyde, a ketone, a carboxylic acid, a carboxylic ester, a carboxylic acid halide (e.g., acetyl chloride), or a carboxylic acid anhydride (e.g., acetic anhydride).

In embodiments, an electrophilic functional group comprises an aldehyde, an α-halo ketone, a maleimide, a succinimide, a hydroxysuccinimide, an isothiocyanate, an isocyanate, an acyl azide, a sulfonyl chloride, a tosylate ester, a glyoxal, an epoxide, an oxirane, a carbonate, an imidoester, an anhydride, a fluorophenyl ester, a hydroxymethyl phosphine derivative, a carbonate, a haloacetyl, a chlorotriazine, a haloacetyl, an alkyl halide, an aziridine, or an acryloyl derivative. In embodiments, an electrophilic functional group is an aldehyde, an α-halo ketone, a maleimide, a succinimide, a hydroxysuccinimide, an isothiocyanate, an isocyanate, an acyl azide, a sulfonyl chloride, a tosylate ester, a glyoxal, an epoxide, an oxirane, a carbonate, an imidoester, an anhydride, a fluorophenyl ester, a hydroxymethyl phosphine derivative, a carbonate, a haloacetyl, a chlorotriazine, a haloacetyl, an alkyl halide, an aziridine, or an acryloyl derivative.

In embodiments, an electrophilic functional group comprises an aldehyde, an α-halo ketone, a maleimide, a succinimide, or a hydroxysuccinimide group.

In embodiments, an electrophilic functional group comprises —CHO, —C(O)CH₂I,

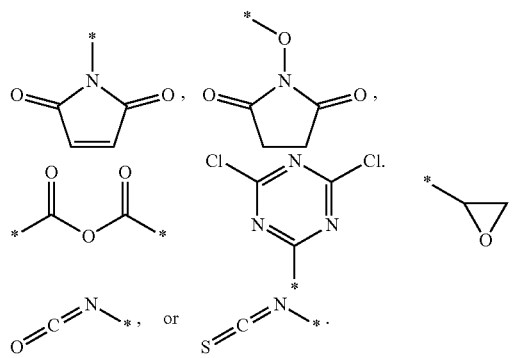

In embodiments, an electrophilic functional group comprises —CHO, —C(O)CH₂I,

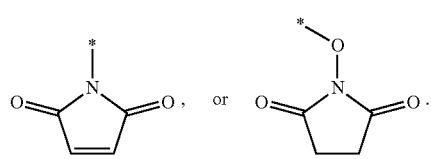 [SMILES: *N1C(=O)C=CC1=O ; *ON1C(=O)CCC1=O]

In embodiments, a chemical moiety 103 comprises a chemical structure that is carbonyl, alkenyl, alkynyl, hydroxyl, amino, thiol, maleimide, succinimide, hydroxysuccinimide, biotinyl, anhydride, chlorotriazine, epoxide, isocyanate, or isothiocyanate. In embodiments, said group that is carbonyl, alkenyl, alkynyl, hydroxyl, amino, thiol, maleimide, succinimide, hydroxysuccinimide, biotinyl, anhydride, chlorotriazine, epoxide, isocyanate, or isothiocyanate is capable of forming a covalent bond to an amplifier group (e.g., an amplifier group 104). In embodiments, said group that is carbonyl, alkenyl, alkynyl, hydroxyl, amino, thiol, maleimide, succinimide, hydroxysuccinimide, biotinyl, anhydride, chlorotriazine, epoxide, isocyanate, or isothiocyanate is capable of forming non-covalent interaction with an amplifier group (e.g., an amplifier group 104).

In embodiments, a chemical moiety 103 is formed from a chemical structure comprising a group that is carbonyl, alkenyl, alkynyl, hydroxyl, amino, thiol, maleimide, succinimide, hydroxysuccinimide, biotinyl, anhydride, chlorotriazine, epoxide, isocyanate, or isothiocyanate. In embodiments, said group that is carbonyl, alkenyl, alkynyl, hydroxyl, amino, thiol, maleimide, succinimide, hydroxysuccinimide, biotinyl, anhydride, chlorotriazine, epoxide, isocyanate, or isothiocyanate has formed a covalent bond to an amplifier group (e.g., an amplifier group 104). In embodiments, said group that is carbonyl, alkenyl, alkynyl, hydroxyl, amino, thiol, maleimide, succinimide, hydroxysuccinimide, biotinyl, anhydride, chlorotriazine, epoxide, isocyanate, or isothiocyanate has formed a non-covalent interaction with an amplifier group (e.g., an amplifier group 104).

In embodiments, a chemical moiety 103 comprises a group that is carbonyl, alkenyl, alkynyl, hydroxyl, amino, thiol, maleimide, succinimide, hydroxysuccinimide, or biotinyl.

In embodiments, a chemical moiety 103 comprises a carbonyl, alkenyl, alkynyl, hydroxyl, amino, thiol, maleimide, succinimide, hydroxysuccinimide, or biotinyl functional group.

In embodiments, a chemical moiety 103 comprises:

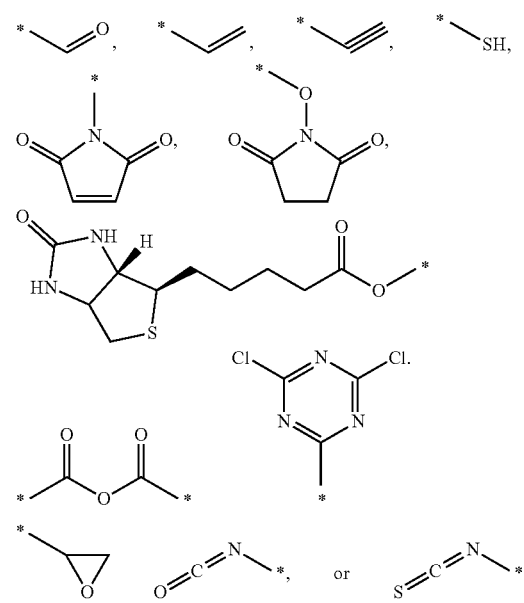

In embodiments, a chemical moiety 103 comprises a group formed from a chemical structure comprising a group that is carbonyl, alkenyl, alkynyl, hydroxyl, amino, thiol, maleimide, succinimide, hydroxysuccinimide, or biotinyl functional group.

In embodiments, a linker group L has the structure of substructure (II):

(II)

wherein

X represents a chemical moiety 101 (e.g., any chemical moiety 101 as described herein);

R represents a spacer moiety 102 (e.g., any spacer moiety 102 as described herein);

Y represents a chemical moiety 103 (e.g., any chemical moiety 103 as described herein); and each of j and k independently is an integer of 0 to 100.

In embodiments, X is

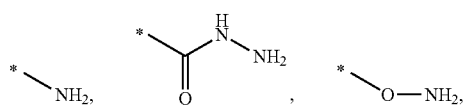

-continued

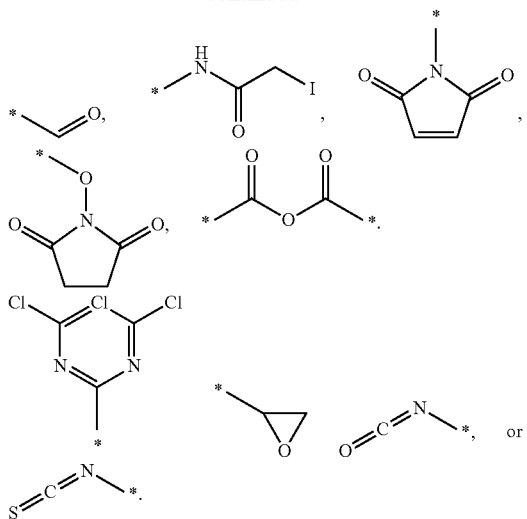

In embodiments, R is

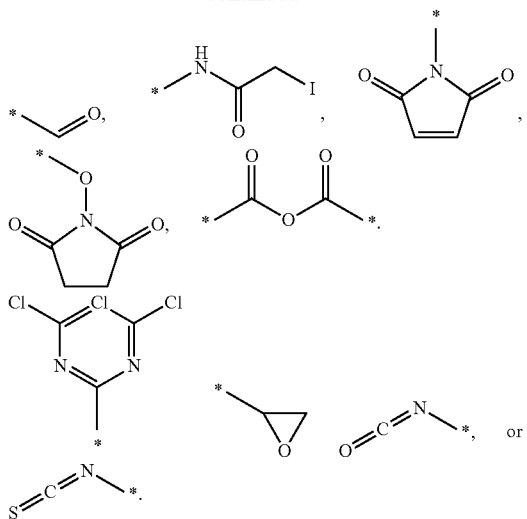

wherein each of n, m, o, p, q, r, s, or t is as described herein (e.g., an integer of 1 to about 300).

In embodiments, Y is

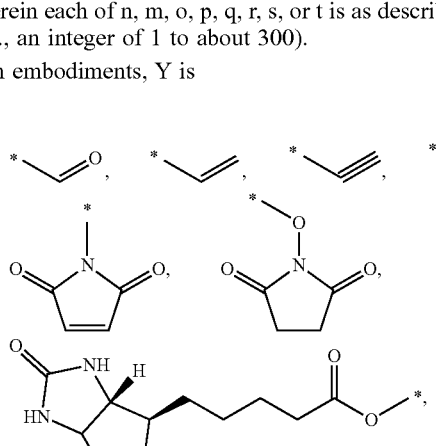

-continued

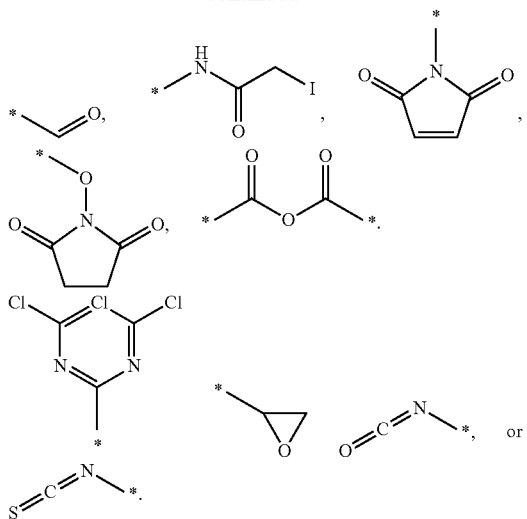

In embodiments, X is capable of forming a covalent bond to a microorganism's surface. In embodiments, X forms a covalent bond to a microorganism's surface.

In embodiments, X is capable of forming one or more non-covalent interactions with a microorganism's surface. In embodiments, X forms one or more non-covalent interactions with a microorganism's surface.

In embodiments, Y is capable of forming a covalent bond to an amplifier group 104 (e.g., a chemical or biochemical amplifier). In embodiments, Y forms a covalent bond to an amplifier group such as an amplifier group 104 (e.g., a chemical or biochemical amplifier.)

In embodiments, Y is capable of forming one or more non-covalent interactions to an amplifier group 104 (e.g., a chemical or biochemical amplifier). In embodiments, Y forms one or more non-covalent interactions to an amplifier group such as an amplifier group 104 (e.g., a chemical or biochemical amplifier.)

In embodiments, a linker group L is:

(13)

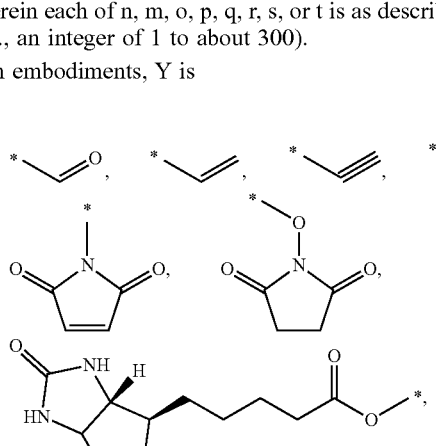

(14)

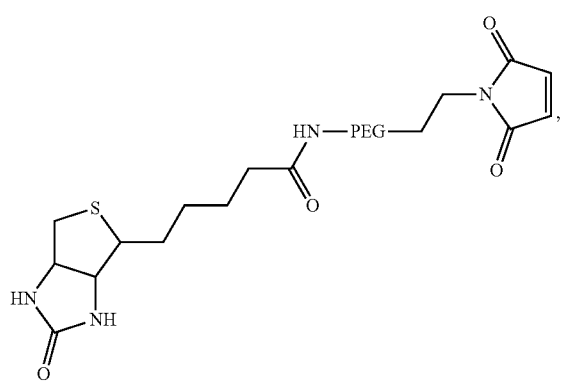

(15)

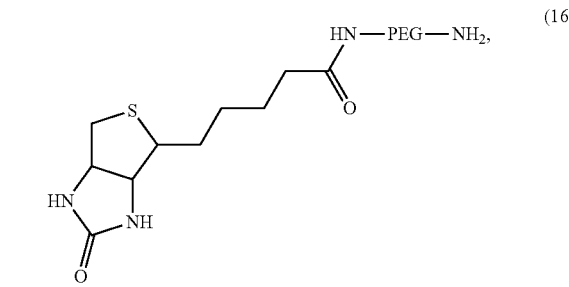

(16)

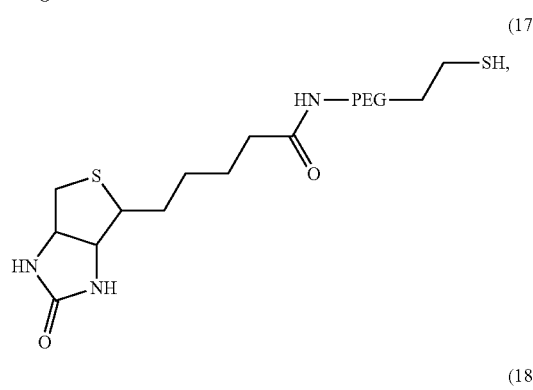

(17)

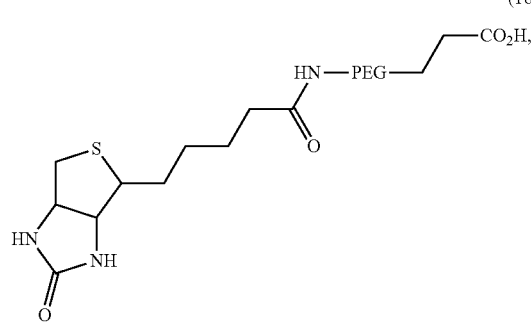

(18)

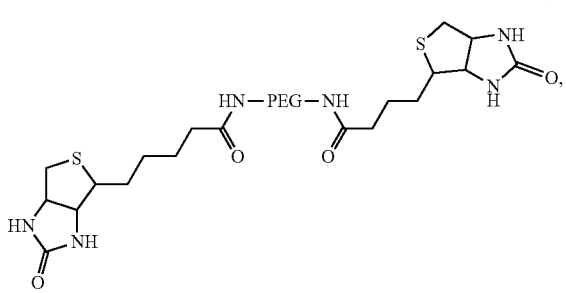

(19)

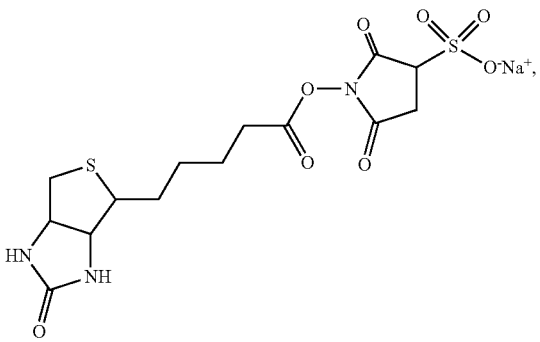

(20)

WGA-Biotin, PolymixinB-Biotin, monoclonal antibody, polyclonal antibody, biotinylated monoclonal antibody, biotinylated polyclonal antibody, europium chelate-antibody, horseradish peroxidase-conjugated antibody, and antibody variants (e.g., Fab: fragment, antigen-binding (one arm); F(ab')2: fragment, antigen-binding, including hinge region (both arms); Fab': fragment, antigen-binding, including hinge region (one arm); scFv: single-chain variable fragment; di-scFv: dimeric single-chain variable fragment; sdAb: single-domain antibody; Bispecific monoclonal antibodies; trifunctional antibody; and BiTE: bi-specific T-cell engager), Exemplary amplifier groups include those described in, e.g., International Publication No. WO 2016/015027 and in International Application No. PCT/US16/42589, each of which is incorporated by reference in its entirety.

In embodiments, an amplifier group (e.g., an amplifier group 104) comprises a catalyst, a fluorophore, or a colormetric dye. In embodiments, an amplifier group (e.g., an amplifier group 104) is a catalyst, a fluorophore, or a colormetric dye.

In embodiments, an amplifier group (e.g., an amplifier group 104) comprises an enzyme, a catalyst, or a nanoparticle. In embodiments, an amplifier group (e.g., an amplifier group 104) is an enzyme, a catalyst, or a nanoparticle.

In embodiments, a chemical amplifier group comprises a catalyst, a fluorophore, a nanoparticle, or a colormetric dye. In embodiments, a chemical amplifier group is a catalyst, a fluorophore, a nanoparticle, or a colormetric dye.

In embodiments, an amplifier group (e.g., an amplifier group 104) comprises a catalyst. In embodiments, an amplifier group (e.g., an amplifier group 104) is a catalyst.

In embodiments, an amplifier group (e.g., an amplifier group 104) comprises a fluorophore. In embodiments, an amplifier group (e.g., an amplifier group 104) is a fluorophore. Exemplary fluorophores include those described in Table 1 of International Application No. PCT/US16/42589, which is incorporated by reference in its entirety.

In embodiments, an amplifier group (e.g., an amplifier group 104) comprises a colormetric dye. In embodiments, an amplifier group (e.g., an amplifier group 104) is a colormetric dye.

In embodiments, an amplifier group (e.g., an amplifier group 104) comprises an enzyme. In embodiments, an amplifier group (e.g., an amplifier group 104) is an enzyme.

In embodiments, an amplifier group (e.g., an amplifier group 104) comprises a nanoparticle. In embodiments, an amplifier group (e.g., an amplifier group 104) is a nanoparticle.

In embodiments, an amplifier group (e.g., an amplifier group 104) comprises a lanthanide.

In embodiments, an amplifier group (e.g., an amplifier group 104) comprises a lanthanide that is europium, strontium, terbium, samarium, or dysprosium. In embodiments, an amplifier group (e.g., an amplifier group 104) comprises a lanthanide selected from the group consisting of: europium, strontium, terbium, samarium, and dysprosium.

In embodiments, an amplifier group (e.g., an amplifier group 104) comprises an organic fluorophore.

In embodiments, an amplifier group (e.g., an amplifier group 104) comprises a fluorophore that is a coordination complex.

In embodiments, an amplifier group (e.g., an amplifier group 104) comprises a europium coordination complex. In embodiments, a coordination complex is a europium coordination complex. In embodiments, an amplifier group (e.g., an amplifier group 104) comprises a ruthenium coordination complex. In embodiments, a coordination complex is a ruthenium coordination complex. In embodiments, an amplifier group (e.g., an amplifier group 104) comprises a rhenium coordination complex. In embodiments, a coordination complex is a rhenium coordination complex. In embodiments, an amplifier group (e.g., an amplifier group 104) comprises a palladium coordination complex. In embodiments, a coordination complex is a palladium coordination complex. In embodiments, an amplifier group (e.g., an amplifier group 104) comprises a platinum coordination complex. In embodiments, a coordination complex is a platinum coordination complex.

In embodiments, an amplifier group (e.g., an amplifier group 104) comprises a chemiluminophore, a quantum dot, an enzyme, an iron coordination catalyst, a europium coordination complex, a ruthenium coordination complex, a rhenium coordination complex, a palladium coordination complex, a platinum coordination complex, a samarium coordination complex, a terbium coordination complex, or a dysprosium coordination complex.

In embodiments, an amplifier group (e.g., an amplifier group 104) comprises a chemiluminophore. In embodiments, an amplifier group (e.g., an amplifier group 104) comprises a quantum dot. In embodiments, an amplifier group (e.g., an amplifier group 104) comprises an enzyme. In embodiments, an amplifier group (e.g., an amplifier group 104) comprises an iron coordination catalyst. In embodiments, an amplifier group (e.g., an amplifier group 104) comprises a europium coordination complex. In embodiments, an amplifier group (e.g., an amplifier group 104) comprises a ruthenium coordination complex. In embodiments, an amplifier group (e.g., an amplifier group 104) comprises a rhenium coordination complex. In embodiments, an amplifier group (e.g., an amplifier group 104) comprises a palladium coordination complex. In embodiments, an amplifier group (e.g., an amplifier group 104) comprises a platinum coordination complex. In embodiments, an amplifier group (e.g., an amplifier group 104) comprises a samarium coordination complex. In embodiments, an amplifier group (e.g., an amplifier group 104) comprises a terbium coordination complex. In embodiments, an amplifier group (e.g., an amplifier group 104) comprises a dysprosium coordination complex.

In embodiments, an amplifier group 104 comprises a moiety that is:

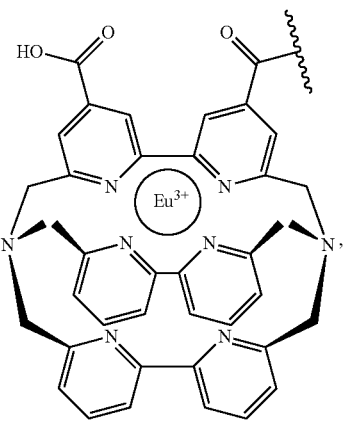

(III)

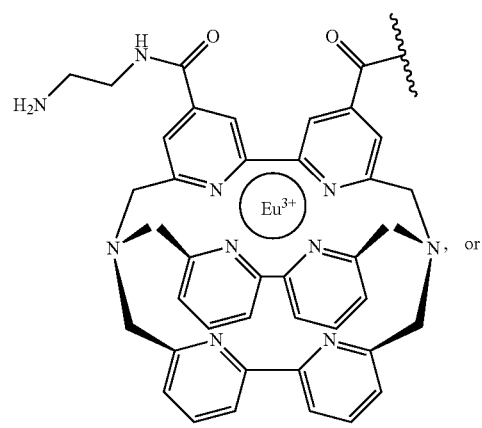

(IV)

, or

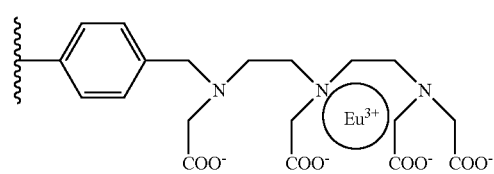

(V)

In embodiments, an amplifier group 104 comprises a moiety that is:

(VI)
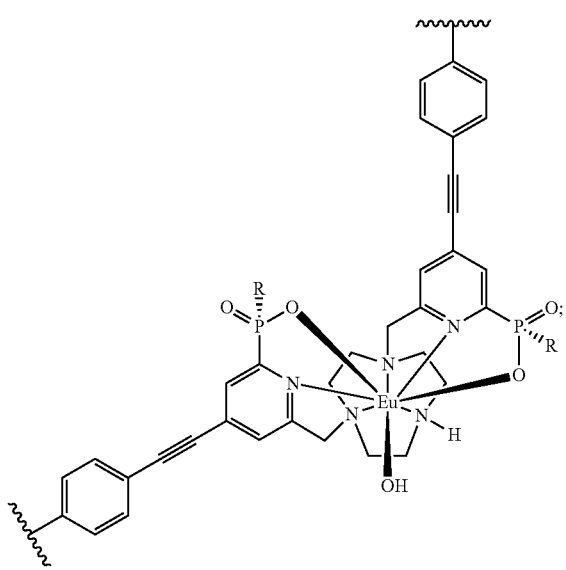

(VII)
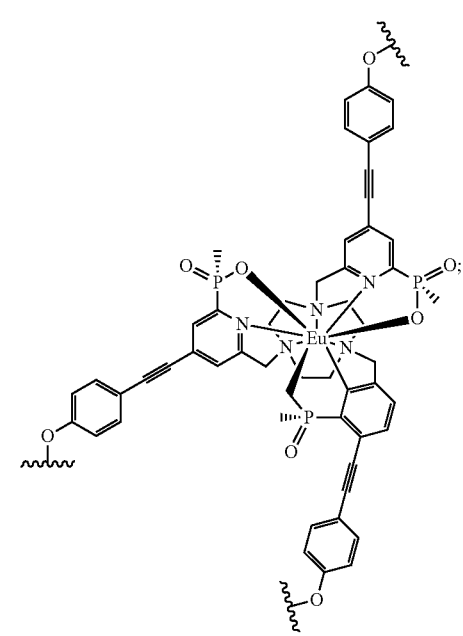

(VIII)
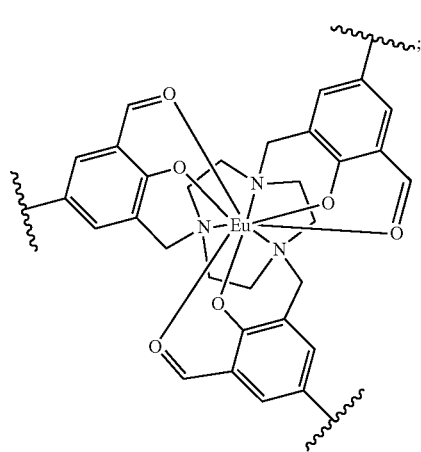

-continued (IX)
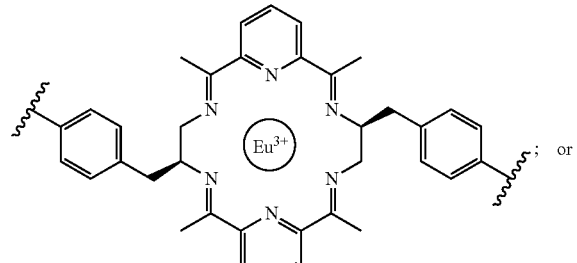
; or (X)
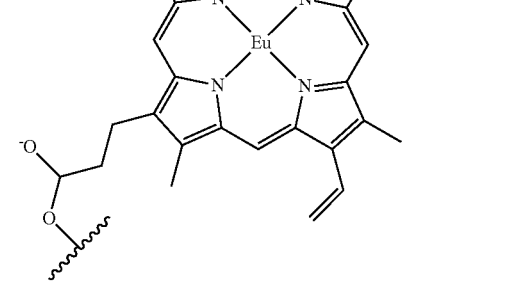

In embodiments, an amplifier group 104 is a catalyst or enzyme. In embodiments, an amplifier group is horseradish peroxidase, alkaline phosphatase, acetyl cholinesterase, glucose oxidase, beta-D-galactosidase, or beta-lactamase.

In embodiments, amplifier group 104 is horseradish peroxidase.

In embodiments, amplifier group 104 is a fluorophore or colormetric dye.

Suitable fluorophores and colormetric dyes are well known to those skilled in the art and are described in *The Molecular Probes® Handbook: A Guide to Fluorescent Probes and Labeling Technologies,* 11th Ed. (2010) and Gomes, Fernandes, and Lima *J. Biochem. Biophys. Methods* 65 (2005) pp 45-80, which are herein incorporated by reference in their entirety. Exemplary fluorophores also include those described in, e.g., International Publication No. WO 2016/015027 and in International Application No. PCT/US16/42589, each of which is incorporated by reference in its entirety.

Examples of suitable fluorophore or colormetric dyes include, but are not limited to, ethidium bromide, propidium iodide, SYTOX green, phenanthridines, acridines, indoles, imidazoles, cyanine, TOTO, TO-PRO, SYTO, 5-carboxy-2,7-dichlorofluorescein, 5-Carboxyfluorescein (5-FAM), 5-Carboxynapthofluorescein, 5-Carboxytetramethylrhodamine (5-TAMRA), 5-FAM (5-Carboxyfluorescein), 5-HAT (Hydroxy Tryptamine), 5-ROX (carboxy-X-rhodamine), 6-Carboxyrhodamine 6G, 7-Amino-4-methylcoumarin, 7-Aminoactinomycin D (7-AAD), 7-Hydroxy-4-methylcoumarin, 9-Amino-6-chloro-2-methoxyacridine, ACMA (9-Amino-6-chloro-2-methoxyacridine), Acridines, Alexa Fluors, Alizarin, Allophycocyanin (APC), AMCA (Aminomethylcoumarin), Bodipy, Carboxy-X-rhodamine, Catecholamine, Fluorescein (FITC), Hydroxycoumarin, Lissamine Rhodamine, Monobromobimane, Oregon Green, Phycoerythrin, SYTO, Thiadicarbocyanine (DiSC3), Thioflavin, X-Rhodamine, C or TetramethylRodamineIsoThioCyanate.

In embodiments, amplifier group 104 is an organometallic compound, transition metal complex, or coordination complex. Exemplary examples are described in but not limited to EP 0 180 492, EP 0 321 353, EP 0 539 435, EP 0 539 477, EP 0 569 496, EP139675, EP64484, U.S. Pat. Nos. 4,283,382, 4,565,790, 4,719,182, 4,735,907, 4,808,541, 4,927,923, 5,162,508, 5,220,012, 5,324,825, 5,346,996, 5,373,093, 5,432,101, 5,457,185, 5,512,493, 5,527,684, 5,534,622, 5,627,074, 5,696,240, 6,100,394, 6,340,744, 6,524,727, 6,717,354, 7,067,320, 7,364,597, 7,393,599, 7,456,023, 7,465,747, 7,625,930, 7,854,919, 7,910,088, 7,955,859, 7,968,904, 8,007,926, 8,012,609, 8,017,254, 8,018,145, 8,048,659, 8,067,100, 8,129,897, 8,174,001, 8,183,586, 8,193,174, 8,221,719, 8,288,763, 8,362,691, 8,383,249, 8,492,783, 8,632,753, 8,663,603, 8,722,881, 8,754,206, 8,890,402, 8,969,862, 9,012,034, 9,056,138, 9,118,028, 9,133,205, 9,187,690, 9,193,746, 9,312,496, 9,337,432, 9,343,685, 9,391,288, and 9,537,107, which are incorporated by reference in their entirety. Exemplary organometallic compounds, transition metal complexes, or coordination complexes also include those described in, e.g., International Publication No. WO 2016/015027 and in International Application No. PCT/US16/42589, each of which is incorporated by reference in its entirety.

In embodiments, amplifier group 104 is a lanthanide coordination complex.

In embodiments, a lanthanide coordination complex is a complex between a lanthanide (e.g., Eu or Tb) and a tetradentate ligand.

In embodiments, a lanthanide coordination complex is a complex between a lanthanide (e.g., Eu or Tb) and a cryptate ligand.

In embodiments, amplifier group 104 is a coordination complex of Lanthanum (La), Cerium (Ce), Praseodymium (Pr), Neodymium (Pm), Samarium (Sm), Europium (Eu), Gadolinium (Gd), Terbium (Tb), Dysprosium (Dy), Holmium (Ho), Erbium (Er), Thulium (Tm), Ytterbium (Yb), Lutetium (Lu), Ruthenium (Ru), Rhodium (Rh), Palladium (Pd), Osmium (Os), Iridium (Ir), or Platinum (Pt).

In embodiments, amplifier group 104 is a coordination complex of a rare earth metal collectively refers to 17 elements consisting of a group of 15 elements from lanthanum having an atomic number of 57 to lutetium having an atomic number of 71 (lanthanides), and two additional elements consisting of scandium having an atomic number of 21 and yttrium having an atomic number of 39. Specific examples of rare earth metals include europium, terbium, lanthanum, cerium, praseodymium, neodymium, promethium, samarium, gadolinium, dysprosium, holmium, erbium, thulium, ytterbium, lutetium, scandium and yttrium, with europium and terbium being preferable, and europium being more preferable.

In embodiments, amplifier group 104 is a coordination complex of a lanthanide (e.g., Europium or Terbium) with diethylenetriaminetetraacetic acid or a cryptate ligand.

In embodiments, amplifier group 104 is a coordination complex of a lanthanide (e.g., Europium or Terbium) with diethylenetriaminetetraacetic acid.

In embodiments, amplifier group 104 is a coordination complex of a lanthanide (e.g., Europium or Terbium) with a cryptate ligand.

In embodiments, a signaling agent (e.g., a chemical signaling agent) comprises or is formed from:

(1)

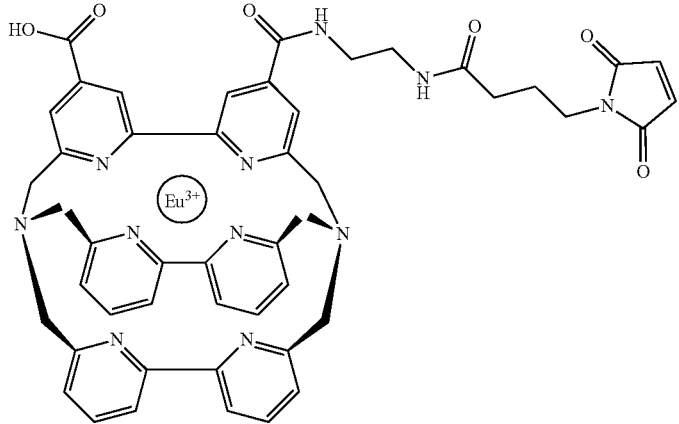

Eu-cryptate-maleimide (2)

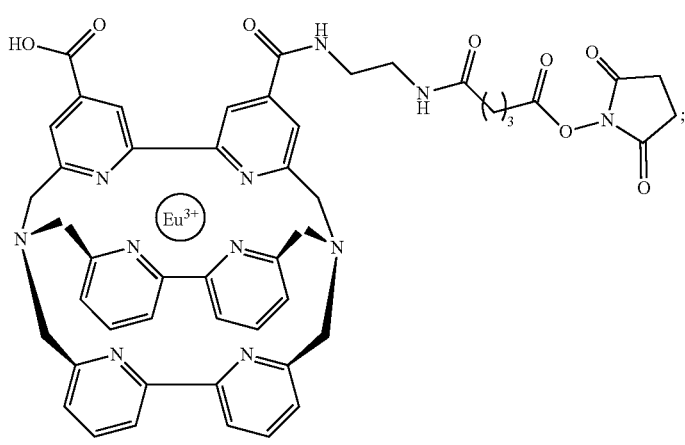

Eu-cryptate-NHS

-continued
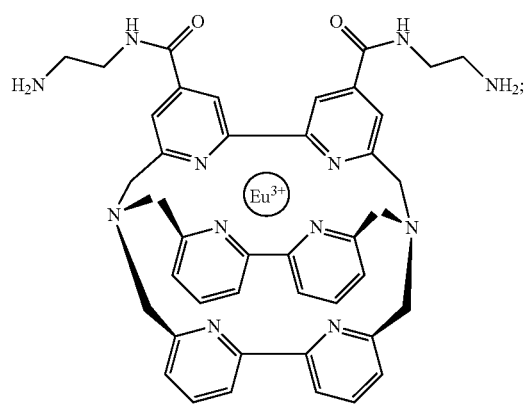
Eu-cryptate-diamine (3)
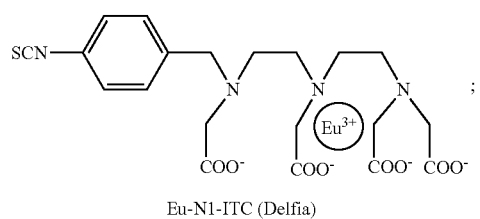
Eu-N1-ITC (Delfia) (4)
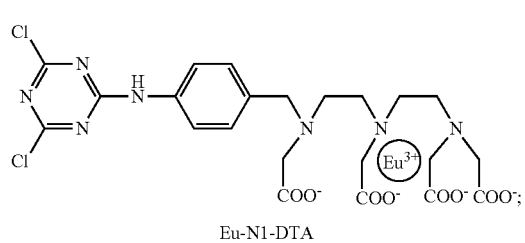
Eu-N1-DTA (5)
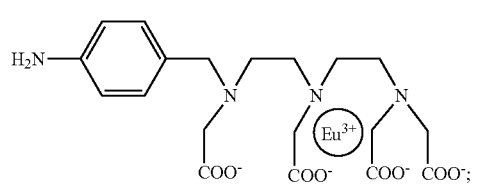
Eu-N1-amino (6)
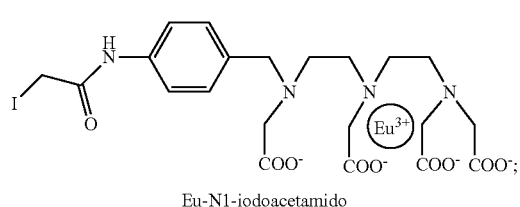
Eu-N1-iodoacetamido (7)
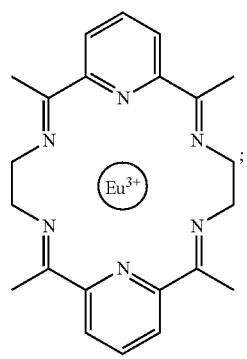
(8)
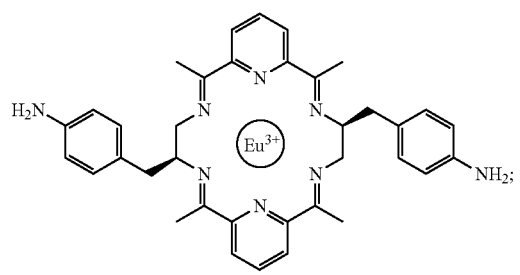
(9)
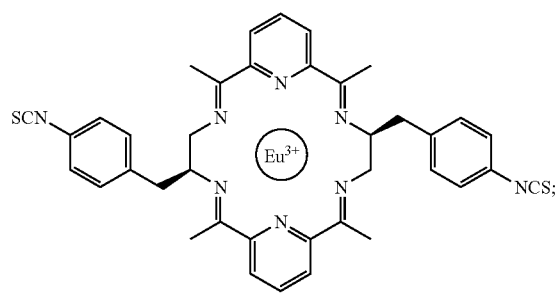
(10)

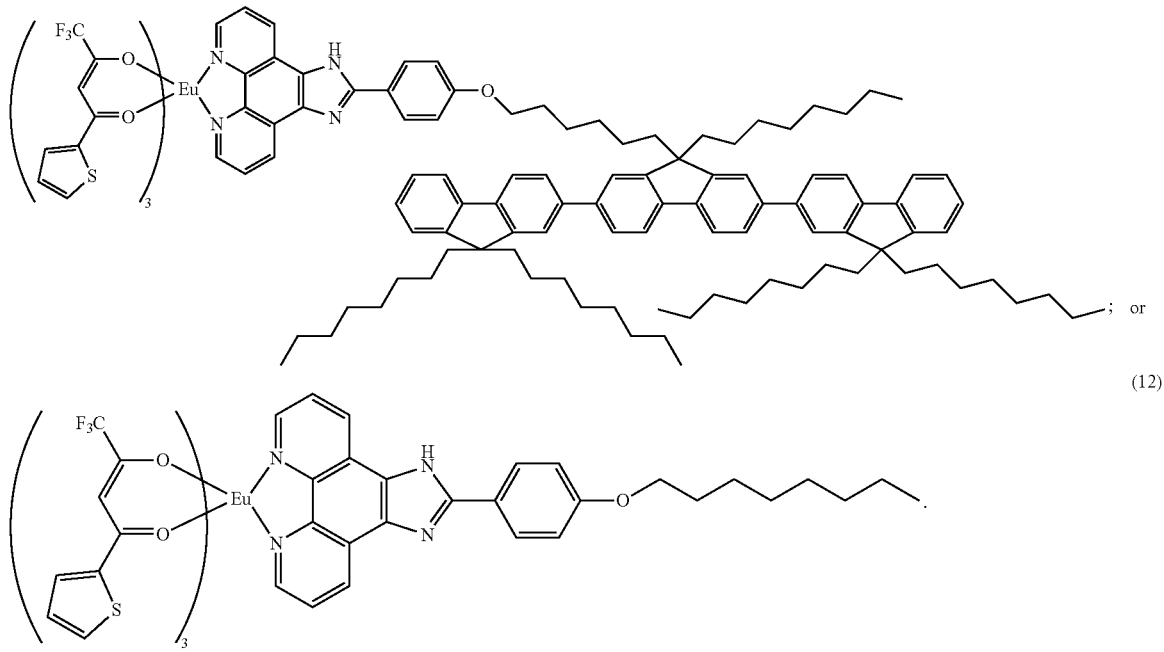

In embodiments, a signaling agent may comprise one or more paramagnetic metal chelates in order to form a contrast agent. Preferred paramagnetic metal ions have atomic numbers 21-29, 42, 44, or 57-83. This includes ions of the transition metal or lanthanide series which have one, and more preferably five or more, unpaired electrons and a magnetic moment of at least 1.7 Bohr magneton. Preferred paramagnetic metals include chromium (III), manganese (II), manganese (III), iron (II), iron (III), cobalt (II), nickel (II), copper (II), praseodymium (III), neodymium (III), samarium (III), gadolinium (III), terbium (III), dysprosium (III), holmium (III), erbium (III), europium (III) and ytterbium (III). Additionally, a signaling agent of the present invention may also comprise one or more superparamagnetic particles:

In embodiments, a signaling agent may comprise one or more metals that are included in a metal complex along with or as a part of a fluorescent compound: The metal complex includes metal complexes having Al, Zn, Be, or the like; a rare-earth metal such as Tb, Eu, or Dy; or a transition metal such as Pt or Ir as a central metal, and having an oxadiazole, thiadiazole, phenylpyridine, phenylbenzimidazole, or quinoline structure as a ligand, such as aluminum quinolinol complexes, benzoquinolinol beryllium complexes, benzoxazole zinc complexes, benzothiazole zinc complexes, azomethyl zinc complexes, porphyrin zinc complexes, and europium complexes.

In embodiments, a signaling agent may comprise a luminophore (donor) which features high luminescence quantum efficiency and long luminescence decay time (>100 ns). Preferred luminophores are cationic, metalorganic complexes of palladium, rhodium, platinum, ruthenium, osmium, rare earths (in particular, europium and lanthanum). The organic portion of these metalorganic complexes may consist, for example, of ligands from the group of porphyrins, bipyridyls, phenanthrolines or other heterocyclical compounds.

In embodiments, a signaling agent capable of binding a microorganism surface comprises an antibody (e.g., monoclonal or polyclonal), modified antibodies (e.g., biotinylated monoclonal antibody, biotinylated polyclonal antibody, europium chelate-antibody, horseradish peroxidase-conjugated antibody), antibody variants (e.g., Fab: fragment, antigen-binding (one arm); F(ab')$_2$: fragment, antigen-binding, including hinge region (both arms); Fab': fragment, antigen-binding, including hinge region (one arm); scFv: single-chain variable fragment; di-scFv: dimeric single-chain variable fragment; sdAb: single-domain antibody; Bispecific monoclonal antibodies; trifunctional antibody; and BiTE: bi-specific T-cell engager), WGA-Biotin, PolymixinB-Biotin, lectin, natural peptide, synthetic peptides, synthetic and/or natural ligands, synthetic and/or natural polymers, synthetic and/or natural glycopolymers, carbohydrate-binding proteins and/or polymers, glycoprotein-binding proteins and/or polymers, charged small molecules, other proteins, bacteriophages, and/or aptamers.

As used herein, the term "antibody" referrers to any herein-described type of antibody, modified antibody, or antibody fragment or type of antibody, modified antibody, or antibody fragment as known in the art. Thus, "a signaling agent comprising an antibody" includes, as examples, a signaling agent comprising an unmodified monoclonal antibody, a Fab fragment, and a trifunctional antibody.

In embodiments, a signaling agent capable of binding a microorganism surface comprises a lanthanide coordination complex, biotin, antibody, and/or an enzyme.

In embodiments, a signaling agent capable of binding a microorganism surface comprises or is formed from a structure comprising an antibody, lectin, natural peptide, synthetic peptides, synthetic and/or natural ligands, synthetic and/or natural polymers, synthetic and/or natural glycopolymers, carbohydrate-binding proteins and/or polymers, glycoprotein-binding proteins and/or polymers, charged small molecules, other proteins, bacteriophages, and/or aptamers.

In embodiments, a signaling agent capable of binding a microorganism surface comprises an amplifier group 104 that comprises a lanthanide coordination complex, and/or an enzyme and streptavidin and/or an antibody and/or aptamer.

In embodiments, a signaling agent capable of binding a microorganism surface comprises a binding moiety comprising a polyclonal and/or monoclonal antibody.

In embodiments, a signaling agent capable of binding a microorganism surface comprises a binding moiety comprising a modified antibody. Exemplary modified antibodies include a biotinylated monoclonal antibody, biotinylated polyclonal antibody, a europium chelate-antibody, and a horseradish peroxidase-conjugated antibody.

In embodiments, a signaling agent capable of binding a microorganism surface comprises a binding moiety comprising an antibody variant. Exemplary antibody variants include Fab: fragment, antigen-binding (one arm); F(ab')$_2$: fragment, antigen-binding, including hinge region (both arms); Fab': fragment, antigen-binding, including hinge region (one arm); scFv: single-chain variable fragment; di-scFv: dimeric single-chain variable fragment; sdAb: single-domain antibody; Bispecific monoclonal antibodies; trifunctional antibody; and BiTE: bi-specific T-cell engager), In embodiments, a signaling agent capable of binding a microorganism surface comprises WGA-Biotin or PolymixinB-Biotin.

In embodiments, a signaling agent capable of binding a microorganism surface comprises a binding moiety comprising a synthetic and/or natural ligand and/or peptide.

In embodiments, a ligand and/or peptide is selected from bis(zinc-dipicolylamine), TAT peptide, serine proteases, cathelicidins, cationic dextrins, cationic cyclodextrins, salicylic acid, lysine, and combinations thereof.

In embodiments, a signaling agent capable of binding a microorganism surface comprises a binding moiety comprising a synthetic and/or natural polymer and/or glycopolymer.

In embodiments, a natural and/or synthetic polymer is linear or branched and selected from amylopectin, Poly(N-[3-(dimethylamino)propyl] methacrylamide), poly(ethyleneimine), poly-L-lysine, poly[2-(N,N-dimethylamino) ethyl methacrylate], and combinations thereof.

In embodiments, a natural and/or synthetic polymer and/or glycopolymer comprises moieties including, but not limited to, chitosan, gelatin, dextran, trehalose, cellulose, mannose, cationic dextrans and cyclodextrins, quaternary amines, pyridinium tribromides, histidine, lysine, cysteine, arginine, sulfoniums, phosphoniums, or combinations thereof including, but not limited to, co-block, graft, and alternating polymers.

In embodiments, a signaling agent capable of binding a microorganism surface comprises a binding moiety comprising a glycoprotein selected from mannose-binding lectin, other lectins, annexins, and combinations thereof.

In embodiments, a signaling agent capable of binding to a microorganism surface comprises:
  an antibody; and
  a europium coordination complex.

In embodiments, a signaling agent capable of binding to a microorganism surface comprises a linker group L that comprises NH$_2$-PEG-Biotin (2K), NH$_2$-PEG-Biotin (4K), sulfo-NHS-Biotin, WGA-Biotin, or polymixinB-Biotin.

In embodiments, a signaling agent capable of binding to a microorganism surface comprises a Europium complex comprises:

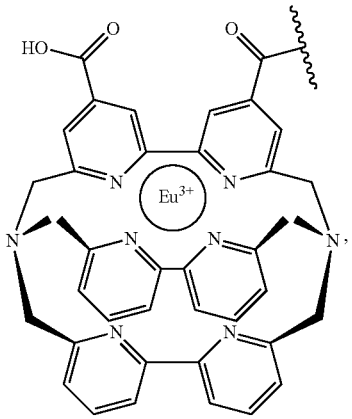

(III)

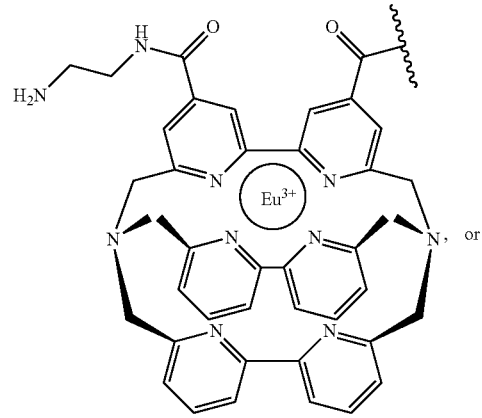

(IV)

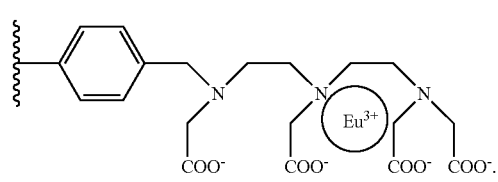

(V)

In embodiments, a signaling agent capable of binding to a microorganism surface comprises a Europium complex comprises:

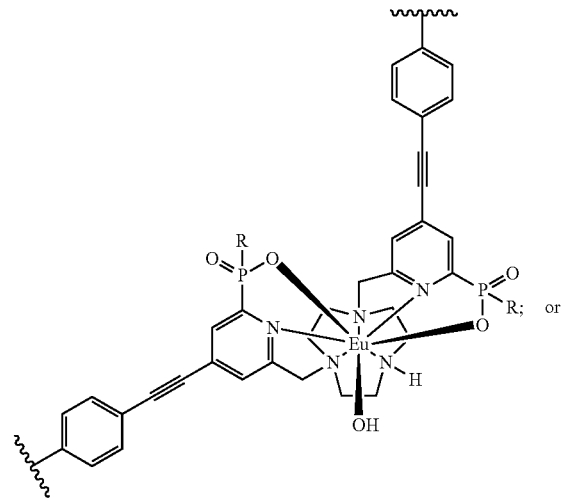

-continued

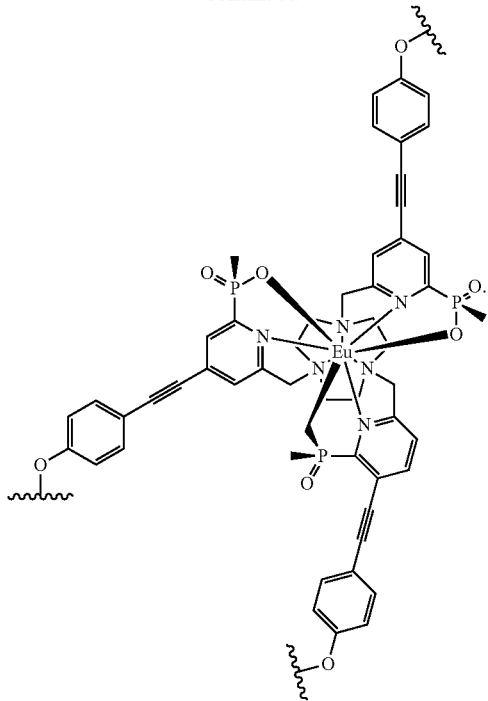

As disclosed in the below working Examples and throughout the Specification and Drawings, the present invention provides, at least:
- >89.9% MIC agreement (±1 dilution) between presently-disclosed methods and CLSI standard with no major/very major errors for seventy-five strains of twelve bacterial species (including β-lactams with gram-negative rods);
- Equivalent MICs between the presently-disclosed method for direct-from-positive-blood culture and CLSI standard blood culture sample processing
- Detection of gram-positive and negative species down to $2 \times 10^3$ CFU/ml;
- Non-specific binding of a microorganism by a signaling agent;
- Use of Europium formulations;
- Semi-automated device use with data output.

Additional teaching relevant to the present invention are described in one or more of the following: EP139675; EP64484; US 2013/0217063; US 2014/0278136; US 2014/0323340; US 2014/0363817; US 2015/0064703; US 2015/0337351; US 2016/0010138; U.S. Pat. Nos. 3,798,320; 4,565,790; 4,647,536; 4,808,541; 4,927,923; 5,457,185; 5,489,401; 5,512,493; 5,527,684; 5,627,074; 5,665,554; 5,695,946; 6,284,470; 6,385,272; 6,844,028; 7,341,841; 7,629,029; 7,868,144; 8,178,602; 8,895,255; PCT/US2016/042589; and WO/2016015027 each of which is incorporated herein by reference in their entireties.

Any of the above aspects and embodiments can be combined with any other aspect or embodiment as disclosed in the Drawings, in the Summary of the Invention, and/or in the Detailed Description, including the below Examples.

Although methods and materials similar or equivalent to those described herein can be used in the practice or testing of the present invention, suitable methods and materials are described below. All publications, patent applications, patents, and other references mentioned herein are incorporated by reference in their entirety. The references cited herein are not admitted to be prior art to the claimed invention. In addition, the materials, methods, and examples are illustrative only and are not intended to be limiting.

EXAMPLES

Example 1

The Present Invention Provides Rapid and Accurate Determination of an Antimicrobial's Minimum Inhibitory Concentration (MIC)

In this example, the present invention for rapidly determining an antimicrobial's minimum inhibitory concentration (MIC) against *Staphylococcus aureus* or *Pseudomonas aeruginosa* was compared to a standard method requiring an overnight incubation of a *S. aureus* or *P. aeruginosa*.

Figure 5:
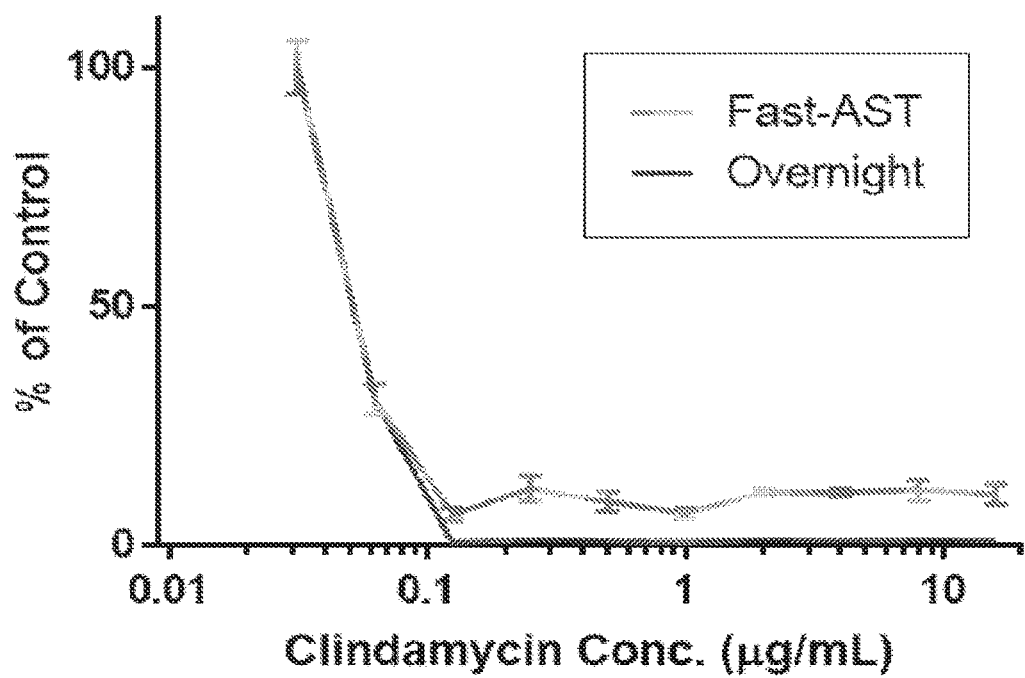
FIG. 5 is a graph showing a comparison of a minimum inhibitory concentration (MIC) determination of clindamycin on *Staphylococcus aureus* (ATCC strain 29213) using the present invention ("fast-AST" technique) and a standard, overnight growth followed by optical density (OD) reading at 600 nm. The data shown for the "fast-AST" is from the five minute point after the start of incubation with detection solution and represents the average and standard deviations of four wells, with values for each assay type relative to an antimicrobial-free control.
Figure 6:
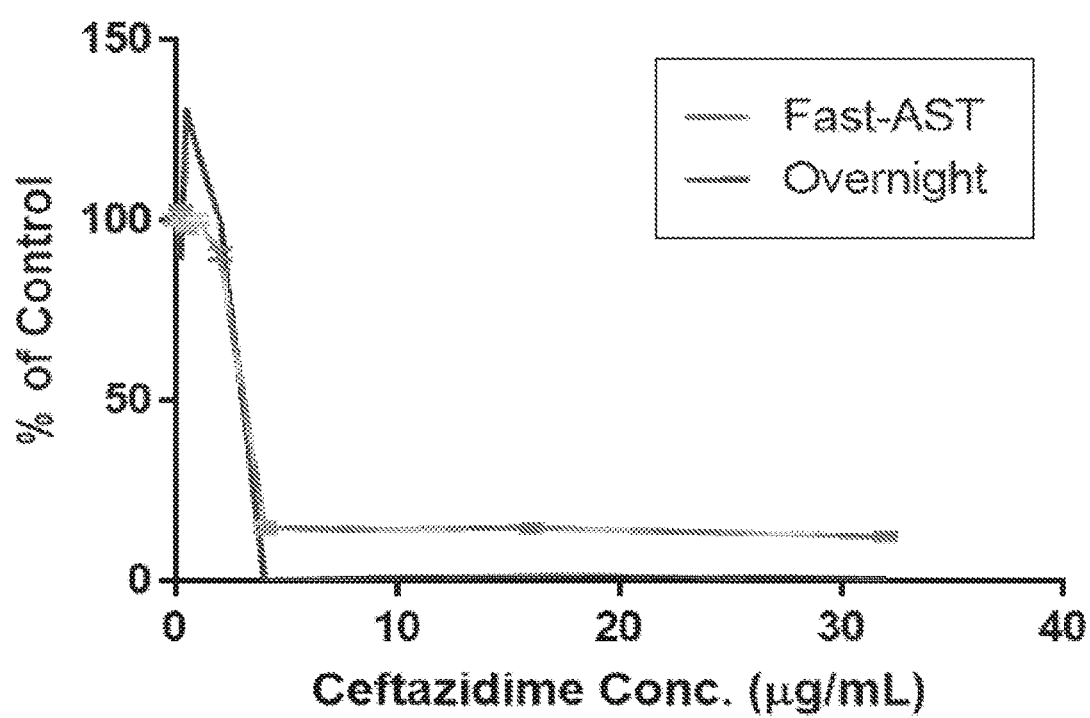
FIG. 6 is a graph showing a comparison of a MIC determination of ceftazidime on *Pseudomonas aeruginosa* (ATCC strain 27853) using the present invention ("fast-AST" technique) and a standard, overnight growth followed by optical density (OD) reading at 600 nm. The data shown represents the average and standard deviations of four wells, with values for each assay type relative to an antimicrobial-free control.

A culture of *Staphylococcus aureus* (ATCC strain 29213) was grown using Mueller-Hinton (MH) broth overnight at 37° C. with vigorous shaking. Concurrently, two sterile 96-well microplates were prepared with serial dilutions of clindamycin from 32 µg/ml to 0.125 µg/ml and a no-clindamycin control, all in MEI broth. The *S. aureus* concentration from the overnight culture was then set to $5 \times 10^5$ CFU/ml using the McFarland standard technique for optical density readings at 600 nm. The microplates, each well containing 200 µL were inoculated with prepared dilutions of antimicrobial and incubated at 37° C. for 3.5 hours for determining antimicrobial susceptibly using a herein-disclosed invention (e.g., the "fast-AST" technique) or incubated at 37° C. overnight (>12 hours) for the $OD_{600}$ control. The "fast-AST" microplate was removed from the shaking incubator after 4 hours and a horseradish peroxidase (HRP) conjugate of a polyclonal rabbit-anti-*S. aureus* antibody (Fitzgerald Industries International, Inc.) was added to each well. The plate was then shaken at room temperature for 20 minutes to allow binding, and afterwards, the microplate was centrifuged at 4,000×g in order to pellet the remaining intact bacteria. The MH broth was then aspirated and sterile broth added for a total of 3 washes. After the final aspiration, a stabilized development solution consisting of 3,3',5,5'-tetramethylbenzidine (TMB) and hydrogen peroxide (ThermoFisher) was added, and the optical density at 650 nm and 450 nm were monitored for 10 minutes with a microplate reader (Vmax, Molecular Devices). After an overnight incubation, the $OD_{600}$ control microplate was removed from the incubator, and the optical density at 600 nm was read directly (Vmax, Molecular Devices). Finally, the MIC was determined per CLSI standards from the data, as shown in FIG. 5. The MIC determined by both techniques is the same: 0.125 µg/ml Similarly, a culture of *Pseudomonas aeruginosa* (ATCC strain 27853) was grown using MH broth overnight at 37° C. with vigorous shaking. Concurrently, two sterile 96-well microplates were prepared with serial dilutions of ceftazidime from 32 µg/ml to 0.125 µg/ml and a no-ceftazidime control, all in MH broth. The *P. aeruginosa* concentration from the overnight culture was then set to $5 \times 10^5$ CFU/ml using the McFarland standard technique for optical density readings at 600 nm. These microplates, each well containing 200 µL, were inoculated with the prepared antimicrobial dilutions and incubated at 37° C. for 3.5 hours for determining antimicrobial susceptibly using a herein-disclosed invention or incubated at 37° C. overnight (>12 hours) for the $OD_{600}$ control. The "fast-AST" microplate was removed from the shaking incubator after 4 hours and a solution of a horseradish peroxidase (HRP) conjugate of a polyclonal rabbit-anti-*P. aeruginosa* antibody (Abcam) was added to each well. The plate was then shaken at room temperature for 20 minutes to allow binding, and afterwards, the microplate was centrifuged at 4,000×g in order to pellet the remaining intact bacteria. The MH broth was then aspirated and sterile broth added for a total of 3 washes. After the final aspiration, a stabilized development solution consisting of 3,3',5,5'-TMB and hydrogen peroxide (ThermoFisher) was added, and the optical density at 650 nm and 450 nm were monitored for 10 minutes with a microplate reader (Vmax, Molecular Devices). The data shown in FIG. 6 depicts from the 5 minute point after the start of incubation with detection solution. After an overnight incubation, the $OD_{600}$ control microplate was removed from the incubator, and the optical density at 600 nm was read directly (Vmax, Molecular Devices). Finally, the MIC was determined per CLSI standards from the data, as shown in FIG. 6. The MIC determined by both techniques is the same: 4 μg/ml.

The accuracy of the present invention in determining MIC is clearly demonstrated in that the slope of the downward region of the data (in FIG. 5 and in FIG. 6) is nearly identical between the present invention and the overnight cultures.

These data show that the present invention is accurately able to determine an antimicrobials' MIC which is at least as accurate as a standard method requiring an overnight incubation of a bacterial culture.

Example 2

The Present Invention Provides Rapid and Accurate Determination of an Antimicrobial's Minimum Inhibitory Concentration (MIC) for Antimicrobial-Resistant Bacteria In this example, the present invention was used to compare the MICs for *P. aeruginosa*, *S. aureus*, and *E. coli* strains that are antimicrobial resistant to, respectively, the MICs for *P. aeruginosa*, *S. aureus*, and *E. coli* strains that are antimicrobial-sensitive.

Figure 7:
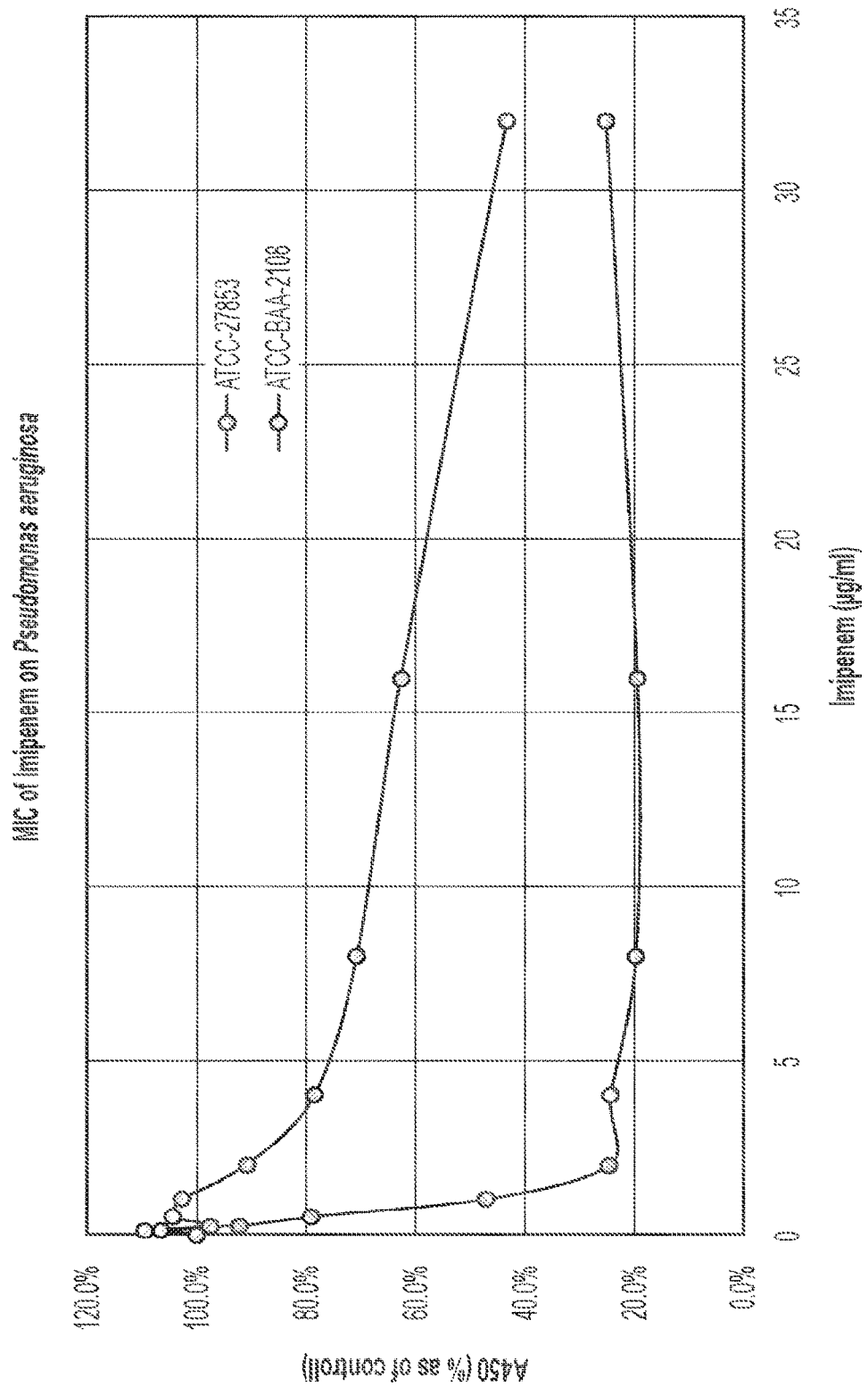
FIG. 7 is a graph showing a MIC determination comparison using the present invention ("fast-AST") for two strains of *Pseudomonas aeruginosa*: a susceptible strain (ATCC strain 27853) and a resistant strain (ATCC strain BAA-2108). The data shown represents the average of four wells, with values for each assay relative to an antimicrobial-free control.

The MIC for the susceptible *P. aeruginosa* strain, ATCC 27853, was determined as described in Example 1, with the key difference that imipenem was used as the antimicrobial (a serial dilution from 32 μg/ml to 0.125 μg/ml was used). The MIC for the resistant *P. aeruginosa* strain, ATCC BAA-2108, was determined similarly. The same 96-well microplate was used for both strains, with 48 wells dedicated to each strain. The experiment was repeated 3 times with similar results, and the resulting data are shown in FIG. 7. The MIC for the susceptible strain is 2 μg/ml; the MIC for the resistant strain is 32 μg/ml.

For *S. aureus*, the same procedure as described above in Example 1 was used, with the exceptions that methicillin was used as the antimicrobial and a resistant strain, ATCC 43300, was used. For *E. coli*, the same procedure as described above for *P. aeruginosa* was used, except *E. coli* susceptible (25922) and resistant (35218) strains were used and ampicillin was used as the antimicrobial, and a HRP-conjugate of a polyclonal rabbit-anti-*E. coli* antibody (Abcam) was used as the chemical moiety that allows the signaling agent to bind the bacterium. The "fast-AST" values after a five-minute incubation with detection solution were compared with $OD_{600}$ overnight controls, and the data is compiled in FIG. 8.

These data show that the present invention is accurately able to differentiate an antimicrobial's MIC for a strain of bacteria that is resistant to the antimicrobial and a strain of the same bacteria that is sensitive to the antimicrobial.

Example 3

The Present Invention Provides a Detectible Signal at Microbial Concentration that is Two-Hundred Fold Less Concentrated than is Required for a Standard Method In this example, the microbial concentration required to provide a detectable signal in present invention for was compared to a standard method requiring an overnight incubation of a *S. aureus*.

*S. aureus* was cultured overnight as described in Example 1. A serial dilution of the overnight colony was made in a 96-well microplate and the absorbance was read at 600 nm. These values were compared with McFarland standards to obtain the bacteria concentration in CFU/ml. The quantifiable region of the curve is shown, in FIG. 9 ($OD_{600}$); the experiment was repeated three times with similar results. A similar dilution series of *S. aureus* was treated with *S. aureus*-specific signaling agents for 20 min, as described in Example 2. Following Example 2's procedure, the microorganisms were centrifuged and washed three times, and a detection solution was added.

Figure 9:
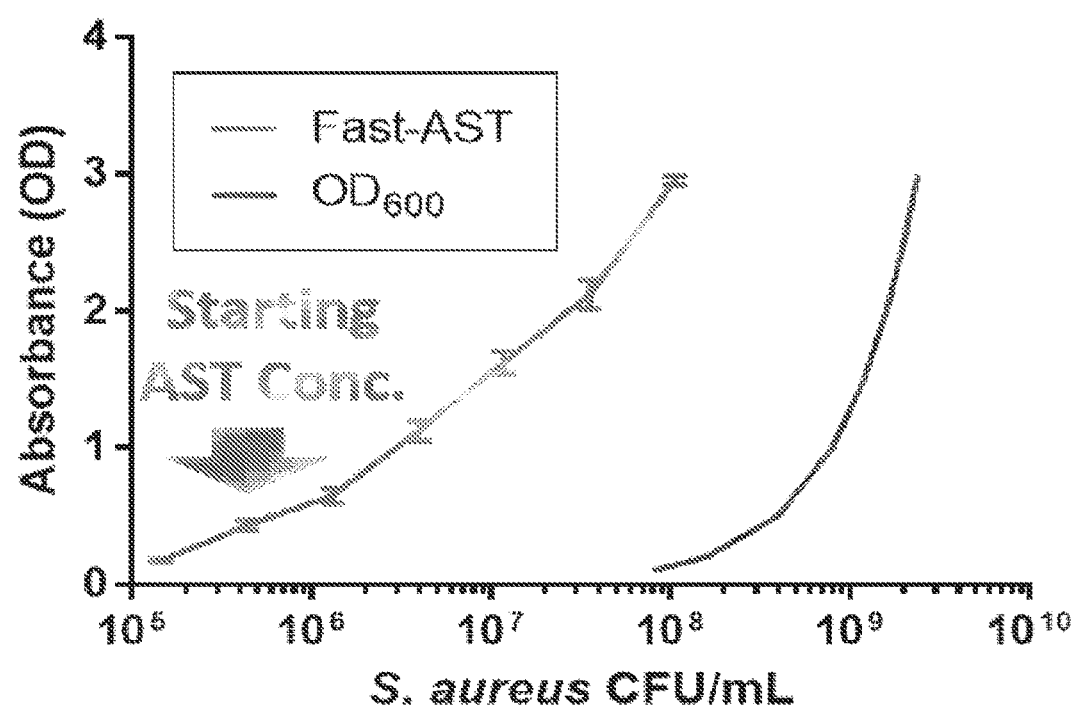
FIG. 9 is a graph showing a comparison of raw optical signal vs. *Staphylococcus aureus* concentration (in CFU/ml) for two techniques: the present invention ("fast-AST" amplification technique) and the standard optical density at 600 nm technique ($OD_{600}$).

In FIG. 9, the resulting absorbance is shown vs. the McFarland standard-determined *S. aureus* concentration. The "fast-AST" signal is visible from the starting bacteria concentration of a Clinical Laboratory Standards Institute (CLSI)-standard AST experiment (i.e., $5 \times 10^5$ CFU/ml), as shown by the arrow. In contrast, the optical signal does not enable accurate quantification until $\sim 10^8$ CFU/ml.

These data show that the present invention is able to provide a detectible and usable signal at microbial culture concentration that is two-hundred fold less concentration than that required for a standard method.

Example 4

The Present Invention Provides MICs Values Similar to Those Obtained from the CLSI Reference Method Across Multiple Species and Strains of Pathogenic Bacteria, Yet in Significantly Less Time than Required for the CLSI Method In this example, the present invention for rapidly determining an antimicrobial's MIC for a plurality of pathogenic bacteria was compared to the Clinical Laboratory Standards Institute (CLSI) method.

Figure 10:
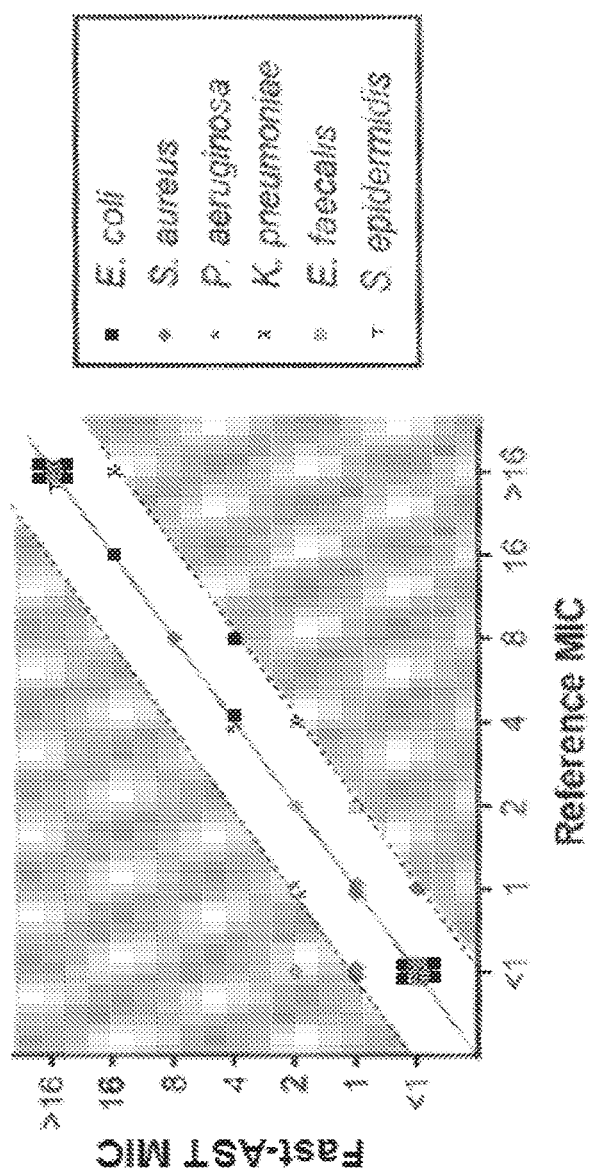
FIG. 10 is a graph showing the MIC results for the present invention (the "fast-AST" method) compared to the Clinical Laboratory Standards Institute (CLSI) reference method for seven pathogenic bacterial species.

As shown in FIG. 10, MIC determinations for six bacteria were obtained after 3.5-hour incubations, whereas the CLSI AST reference method determinations were obtained after sixteen hour incubations (for ampicillin-treated cultures) or twenty-four hour incubations (for oxacillin-treated cultures). The drug, signaling agent/chemical moiety ("antibody-HRP conjugate"), and bacteria strains are listed in FIG. 11. A for the signaling agent/chemical moiety, wheat germ agglutinin (WGA) HRP conjugate was used for *S. epidermidis* testing, and the "fast-AST" assay follows the procedure of Example 2 above. All clinical isolates were de-identified samples and were sub-cultured a minimum of two times before use. A total of eighty-seven individual samples were tested, including, but not limited to, the following bacterial species: *E. coli*, *S. aureus*, *P. aeruginosa*, *K pneumoniae*, *E. faecalis*, Coagulase-Negative *Staphylococci*, *P. mirabilis*, *E. faecium*, *E. clocae*, and *A. baumannii*. It is noteworthy that the bacterial species tested in this example (except *P. mirabilis*) are together responsible for >90% of positive blood cultures in many clinical laboratories. Thus, the present invention has clear clinical relevance to human infectious diseases. The MIC values between the present invention and the CLSI method are highly similar, yet the present invention requires a three and half hour incubation whereas the CLSI method requires sixteen hour or twenty-four hour incubations.

These data show that the present invention is accurately able to determine an antimicrobials' MIC which is at least as accurate as the CLSI method, yet takes significantly less time to determine the MIC; thus, the present invention greatly reduces time before a patient is provided an appropriate treatment regimen, i.e., a specific antimicrobial and at a particular dosage.

Example 5

With *S. aureus* and *K. pneumoniae* Samples, Across a Wide Variety of Antimicrobials, the Present Invention Provides MICs Values Similar to Those Obtained from the CLSI Reference Method, Yet in Significantly Less Time In this example, the present invention was used to rapidly determine a plurality of antimicrobials' MICs when treating *S. aureus* (a gram-positive bacterium) or *K. pneumoniae* (a gram-negative bacterium) and compared to MIC values obtained by the CLSI method.

Commercial, full-panel dried antimicrobial plates, Sensi-Titre® (ThermoFisher) were used in the method of the present invention as described above in Example 2, where bacterial viability was assessed at four hours. Representative *S. aureus* and *K. pneumoniae* results are shown in FIG. 12A to FIG. 12C. There was excellent agreement between MIC values obtained from the present invention "fast-AST" and the CLSI-obtained results for all experiments except for the erythromycin experiment with *S. aureus* and the tetracycline and imipenem experiments with *K. pneumonia*; however, according to the FDA, the discrepancies between the present invention and the CLSI results are "minor errors", see, FIG. 12C.

These data show that the present invention is accurately able to determine, for two dissimilar bacterial species, a plurality of antimicrobials' MIC which are at least as accurate as the CLSI method, yet takes significantly less time to determine the MIC; thus, the present invention greatly reduces time before a patient is provided an appropriate treatment regimen, i.e., a specific antimicrobial and at a particular dosage.

Example 6

Using Multiple *S. aureus* and *E. coli* Clinical Strains, Across a Wide Variety of Antimicrobials, the Present Invention Provides MICs Values Similar to Those Obtained from the CLSI Reference Method, Yet in Significantly Less Time In this example, the present invention was used to rapidly determine a plurality of antimicrobials' MICs when treating *S. aureus* (a gram-positive bacterium) or *E. coli* (a gram-negative bacterium) and compared to MIC values obtained by the CLSI method.

Figure 15:
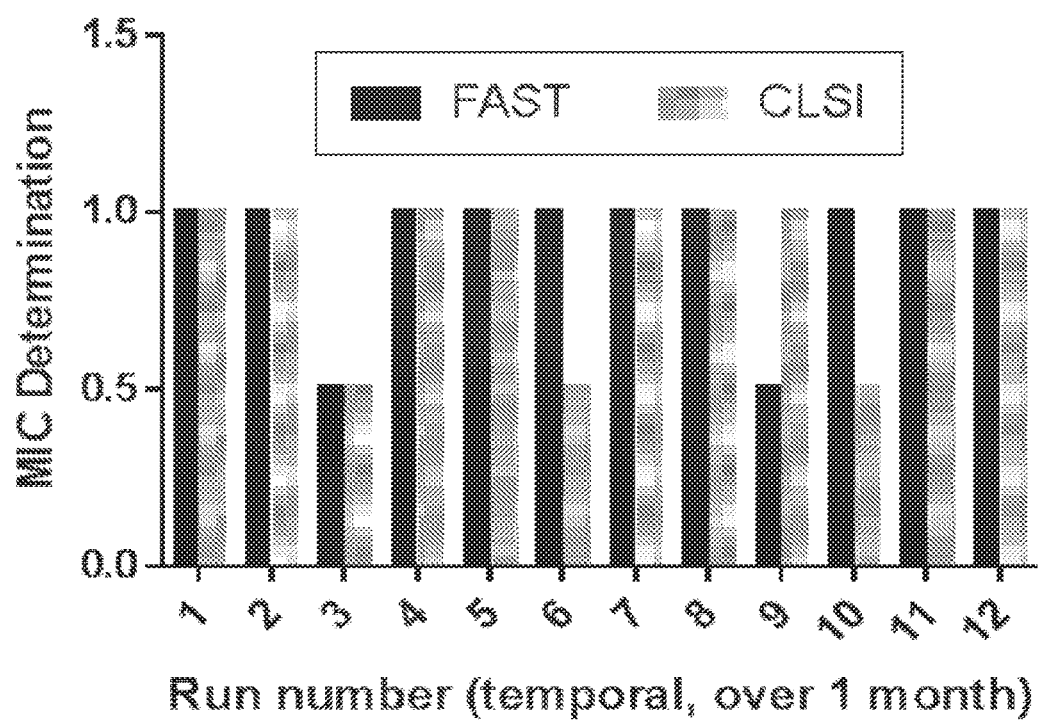
FIG. 15 is a graph showing that the present invention ("fast-AST") consistently produces MIC results similar to those obtained by the CLSI standard reference method over the course of one month on the same clinical species of *S. aureus*.

As in Example 5, SensiTitre® plate (ThermoFisher) was used to perform these experiments. The same procedure was used as described in Example 2, except 50 µL of inoculum was added to each well, according to ThermoFisher's instructions. The CLSI reference method was performed for twenty-four hours (oxacillin and vancomycin) and eighteen hours (levofloxacin) and for all experiments using the present invention ("fast-AST" method) was performed in four hours (including a three and half hour incubation). Results are shown in FIG. 13A to FIG. 13C and FIG. 14A to FIG. 14D. The dark lines in FIG. 13A to FIG. 13C and FIG. 14A to FIG. 14D show the CLSI breakpoints for each antimicrobial. Essential Agreement "EA" and Categorical Agreement "CA" are defined as by the FDA in their Class II Guidance Document for Automated AST Systems. Additionally, for one clinical species of *S. aureus*, multiple "fast-AST" assays and CLSI standard reference assays, as described above, were run over the course of one month to determine consistency of results; see FIG. 15.

These data show that the present invention ("fast-AST" procedure) provides consistent results with the CLSI reference method when tested with multiple antimicrobials on *S. aureus* and *E. coli* clinical strains, yet takes significantly less time to determine the MIC; thus, the present invention greatly reduces time before a patient is provided an appropriate treatment regimen, i.e., a specific antimicrobial and at a particular dosage.

Example 7

The Present Invention Provides Rapid and Accurate Determination of a Plurality of Antimicrobials' MICs for an Antimicrobial-Resistant Bacterium In this example, the present invention was used to determine the MICs for a plurality of antimicrobials for *E. coli* strains that are antimicrobial resistant to the MICs for *E. coli* strains that are antimicrobial-sensitive.

Figure 16:
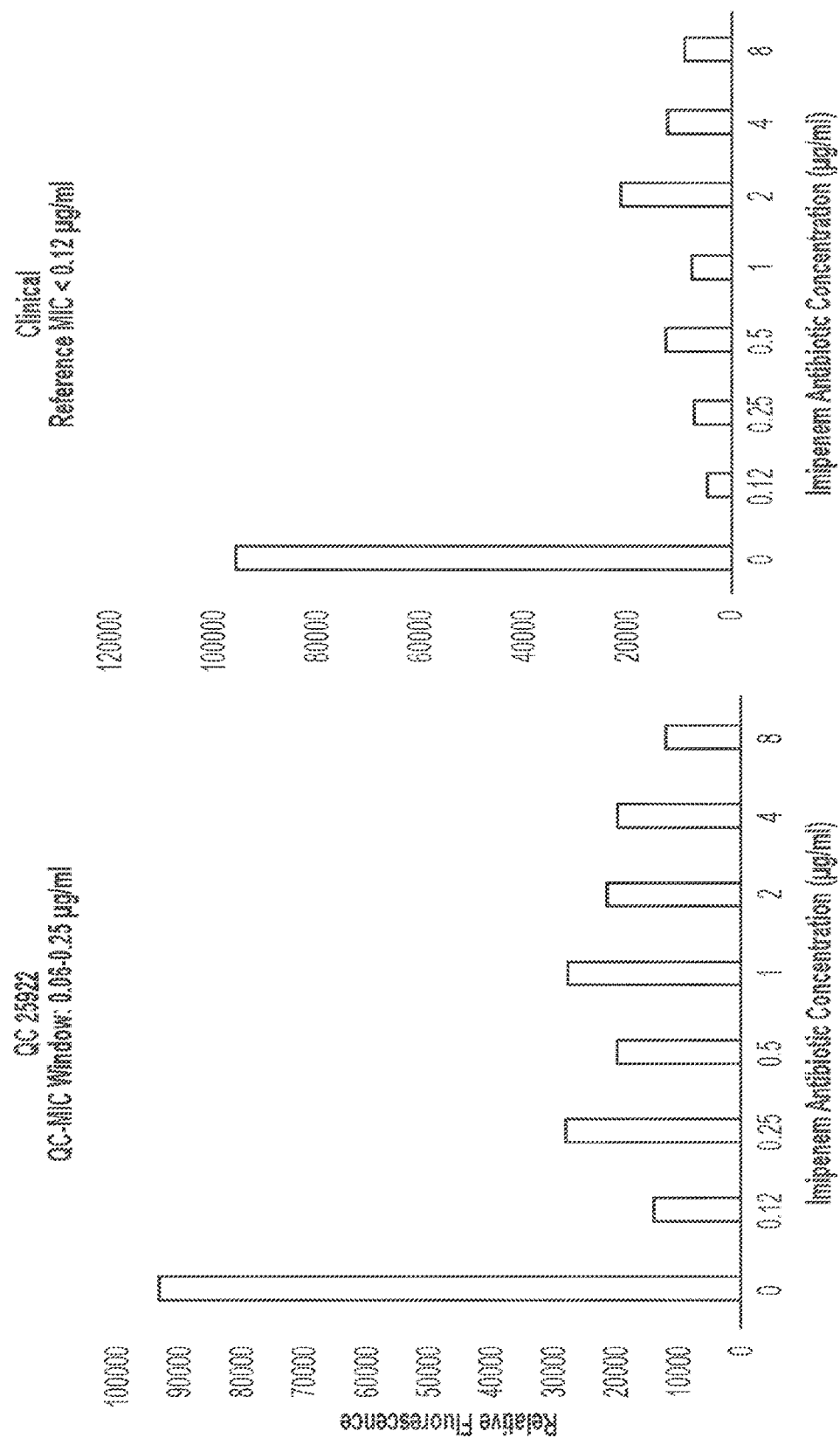
FIG. 16 to FIG. 23 are graphs comparing sensitives for a plurality of antimicrobials for a chemically sensitive *E. coli* strain ("QC 25922") and a clinically-relevant antimicrobial-resistant strain ("Clinical"). The antimicrobials used are Imipenem (FIG. 16); Ampicillin (FIG. 17); Ceftazidime (FIG. 18); Gentamicin (FIG. 19); Levofloxacin (FIG. 20); Trimethethoprim/Sulfamethoxazole (SXT) (FIG. 21); Ciprofloxacin (FIG. 22); and Cetriaxone (FIG. 23).
Figure 17:
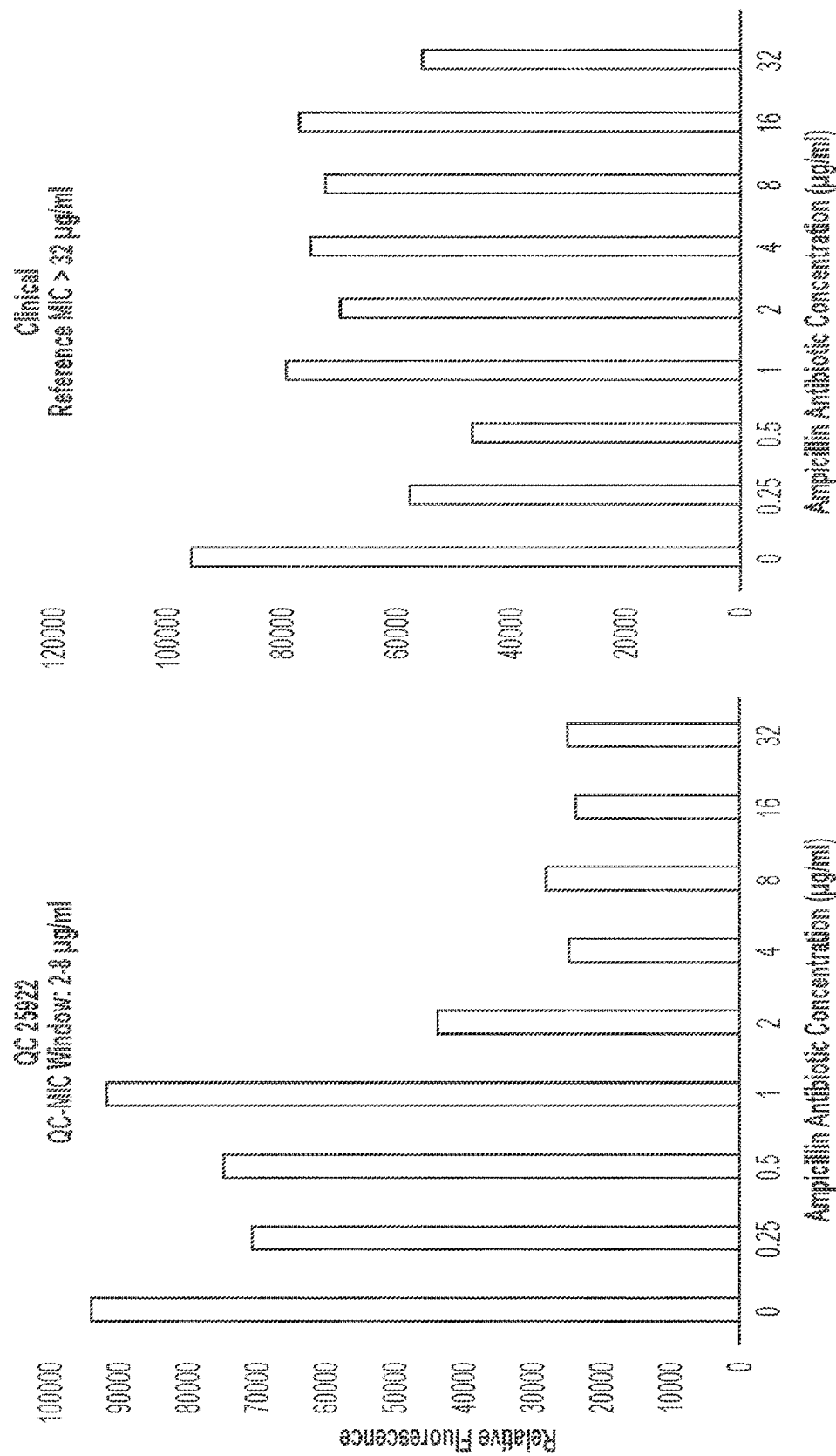
Figure 18:
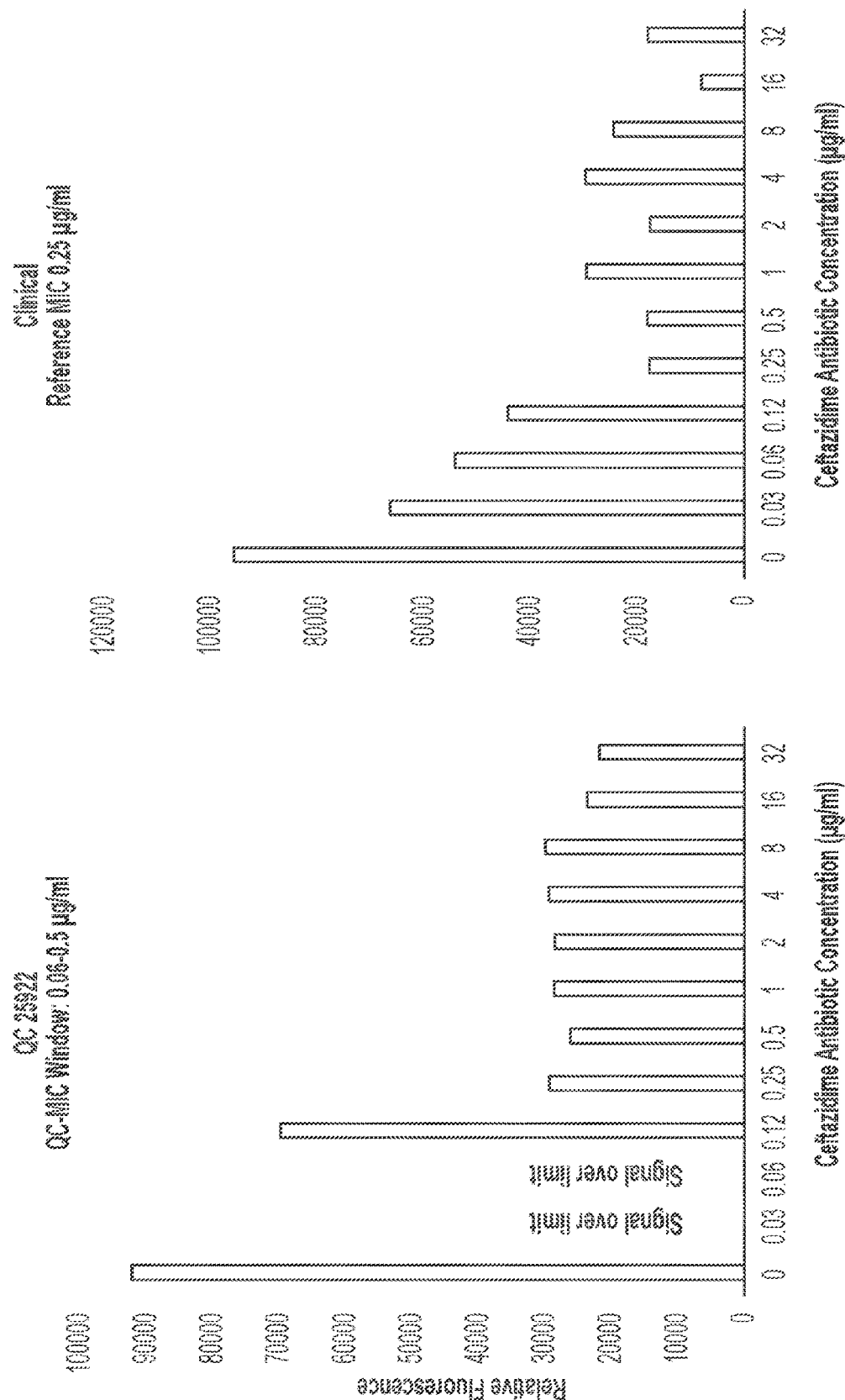
Figure 19:
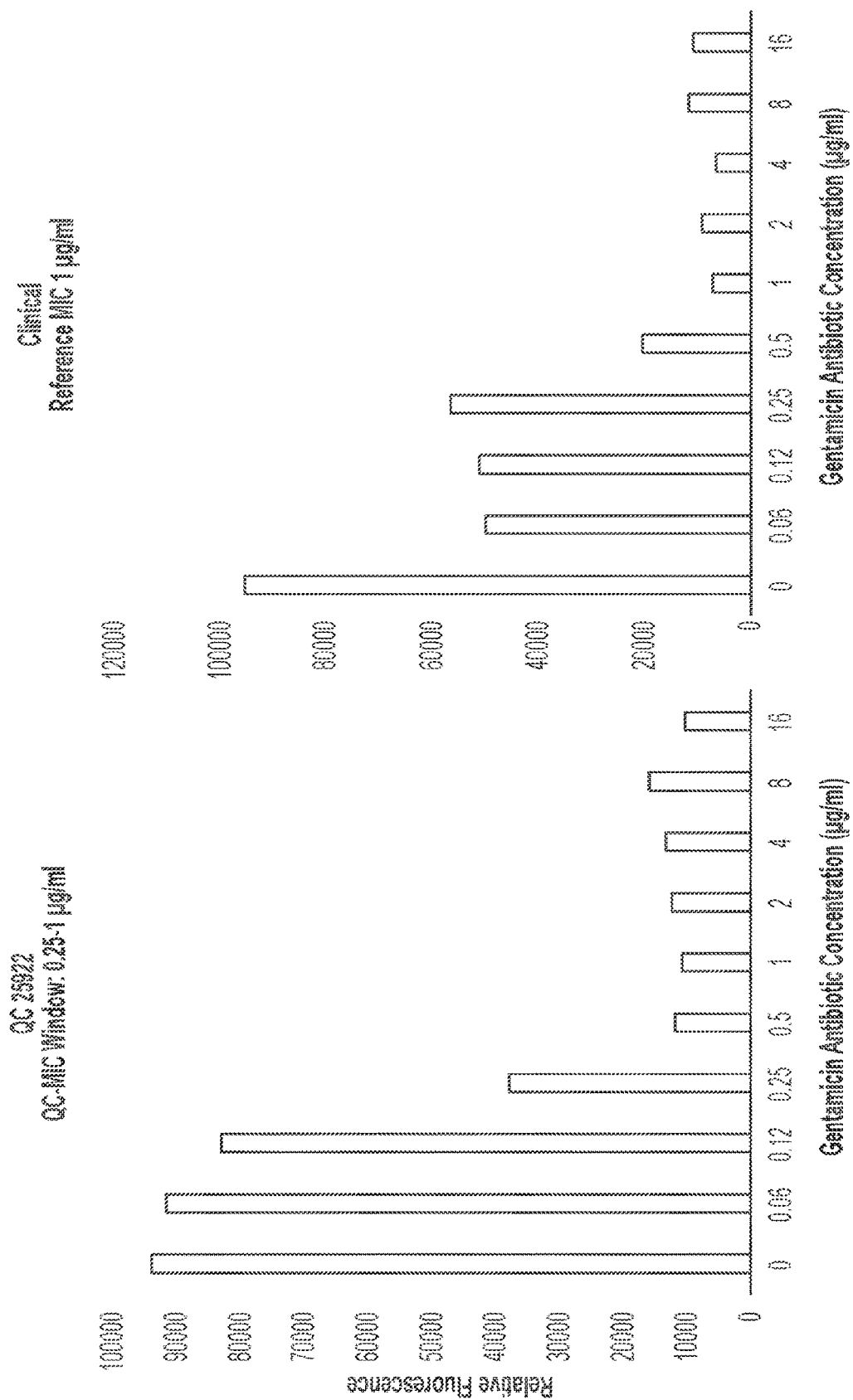
Figure 20:
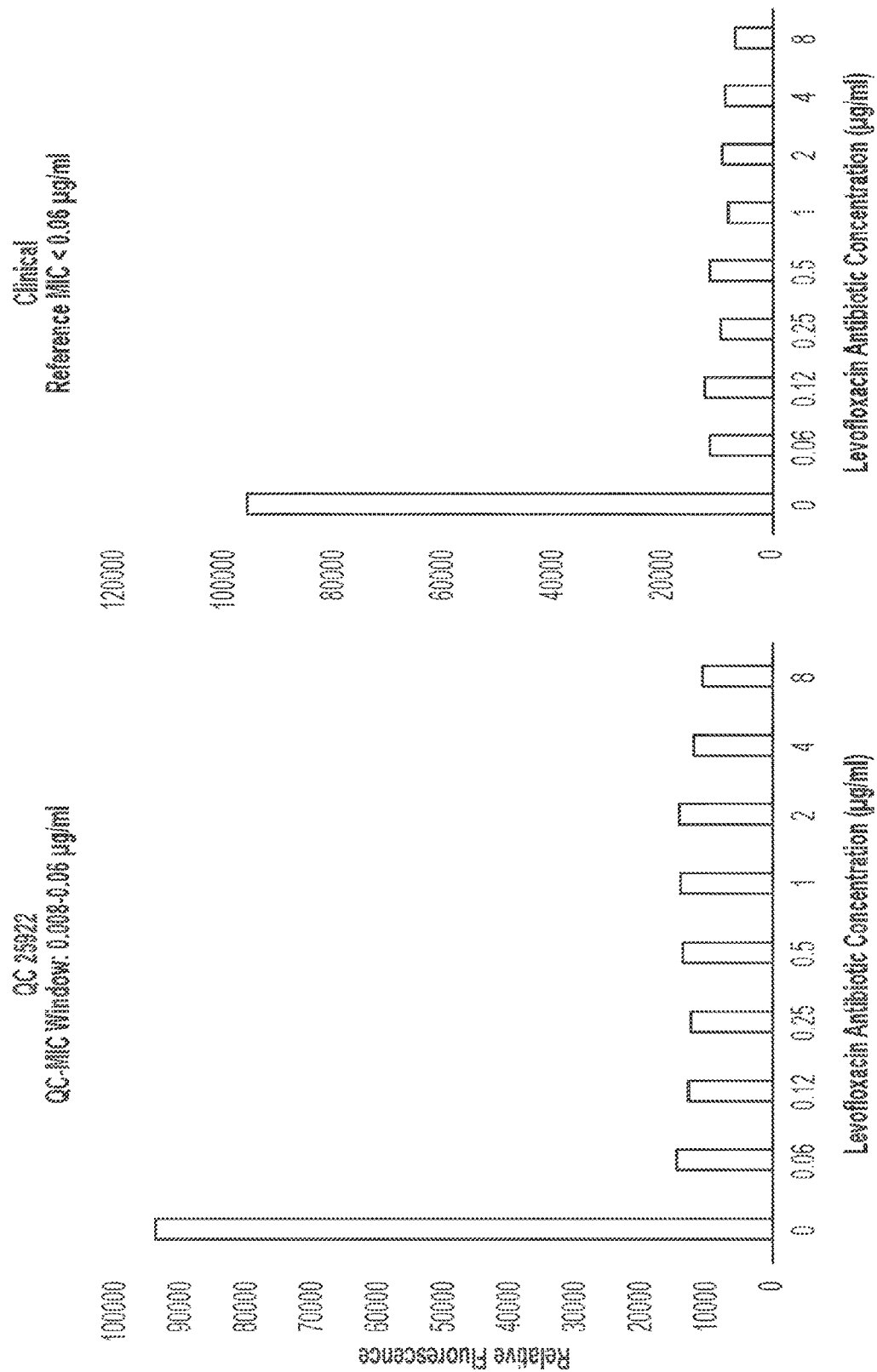
Figure 21:
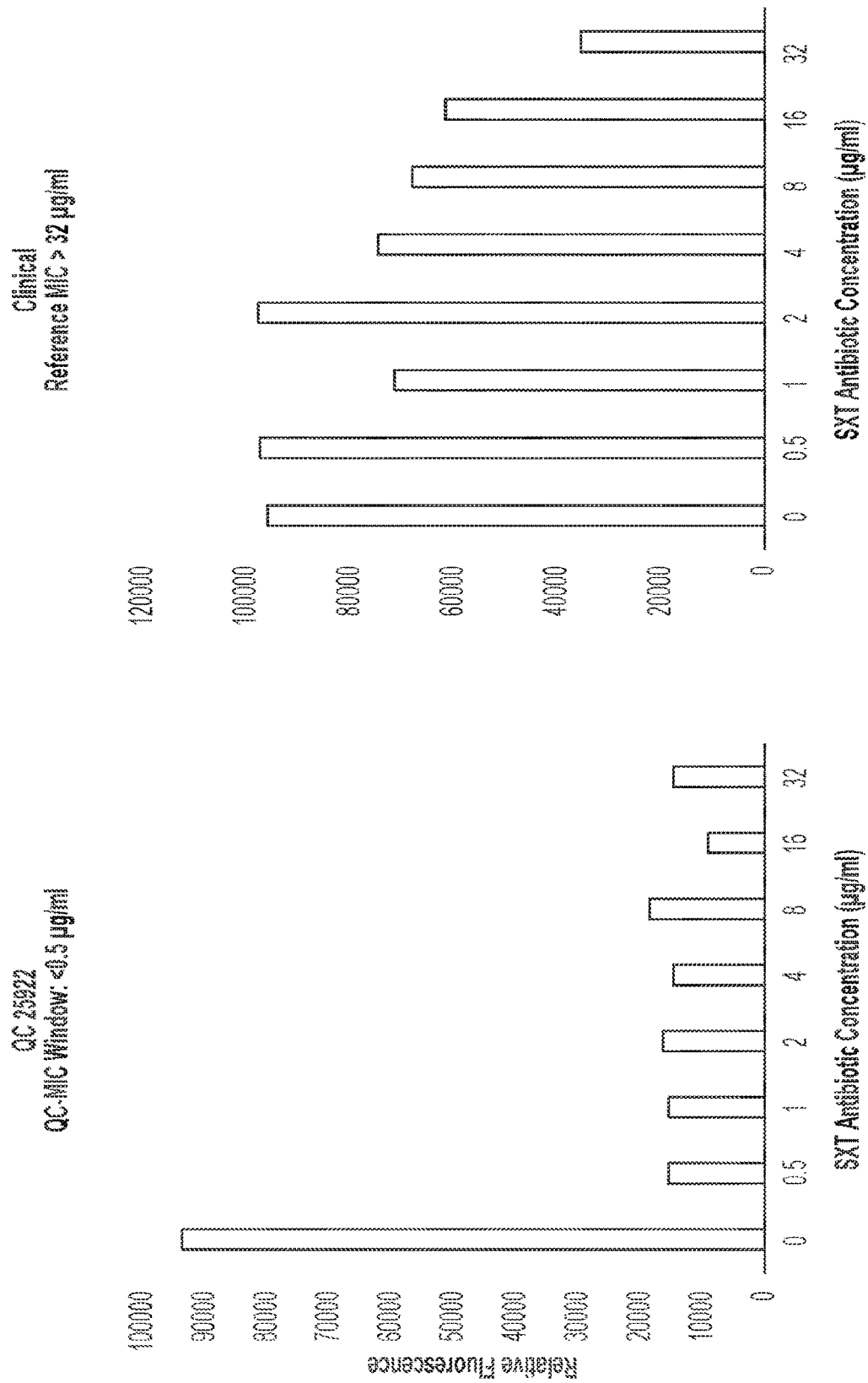
Figure 22:
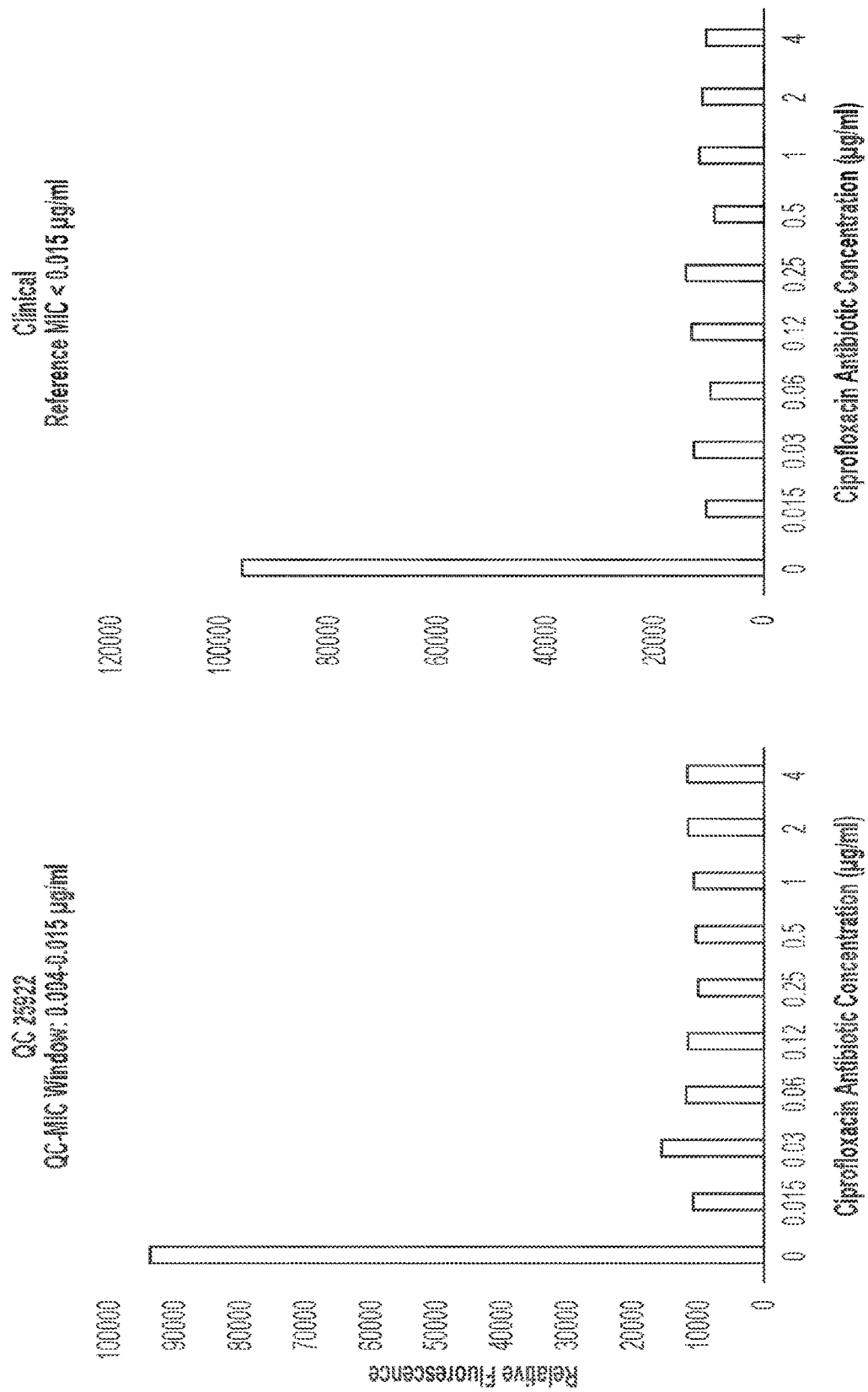
Figure 23:
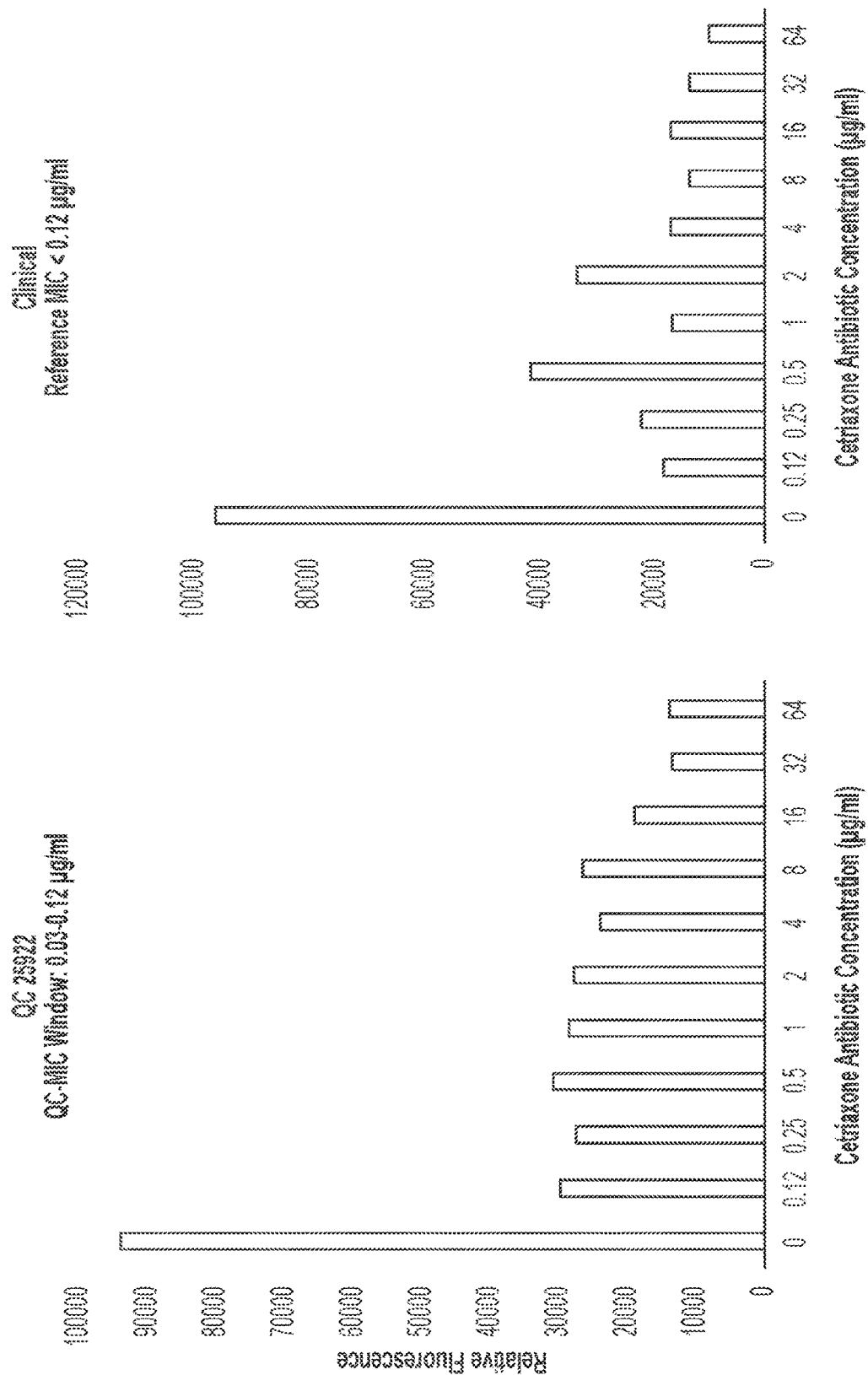

Both *Escherichia coli* (QC strain, ATCC 25922) and clinical resistant *E. coli* ("Clinical") were cultured under standard sterile conditions in Mueller-Hinton (MH) broth overnight at 37° C. with shaking. The *E. coli* concentration from the overnight culture was then set to $5 \times 10^5$ CFU/ml using the McFarland standard technique for optical density readings at 600 nm. Concurrently, two sterile 96-well microplates were prepared with serial dilutions of a specified antimicrobial (see below) and a no-antimicrobial (saline) control, all in MH broth. The microplates, each well containing 200 µL, were inoculated with the prepared antimicrobial dilutions and incubated at 37° C. for 3 hours, 45 minutes for determination using the present invention (the "fast-AST" technique). The "fast-AST" microplates were removed from the shaking incubator after 3 hours, 45 minutes and centrifuged for 2.5 minutes at 2500 g in order to pellet. The MH broth was then aspirated and 1004 of water was added to each well of both microplates. Then, 104 of the chemical moiety (here, Europium-Cryptate formulation) was added to each well (to 20 ng/well) and 10 µL of 5% Glutaraldehyde (as the signaling agent) was added to each well. The two microplates were then shaken at 300 rpm for 30 minutes. After, both plates were centrifuged for 2.5 minutes at 2500 g to pellet. The solution was aspirated and a wash of 200 µL PBS-tween was added to each well, followed by a centrifugation to pellet. After aspiration of solution, a second identical wash of 200 µL PBS-tween occurred, followed by a final centrifugation to pellet. The plate was then read using time resolved fluorescence on a BioTek H1 plate reader. This process was carried out with the following antimicrobial preparations: Imipenem at diluted concentrations from 8 µg/ml to 0.12 µg/ml (FIG. 16);

Ampicillin at diluted concentrations from 32 μg/ml to 0.25 μg/ml (FIG. 17); Ceftazidime at diluted concentrations from 32 μg/ml to 0.03 μg/ml (FIG. 18); Gentamicin at diluted concentrations from 16 μg/ml to 0.06 μg/ml (FIG. 19); Levofloxacin at diluted concentrations from 8 μg/ml to 0.06 μg/ml (FIG. 20); Trimethethoprim/Sulfamethoxazole (SXT) at diluted concentrations from 32 μg/ml to 0.5 μg/ml (FIG. 21); Ciprofloxacin at diluted concentrations from 4 μg/ml to 0.015 μg/ml (FIG. 22); and Cetriaxone at diluted concentrations from 64 μg/ml to 0.12 μg/ml (FIG. 23).

As seen in FIG. 16 to FIG. 23, *Escherichia coli* (QC strain, ATCC 25922) and the clinical resistant *E. coli* ("Clinical") had similar MICs for Imipenem, Ceftazidime, Gentamicin, Levofloxacin, Ciprofloxacin, and Cetriaxone whereas the two strains had dissimilar MICs for Ampicillin and Trimethethoprim/Sulfamethoxazole (SXT). Accordingly, the data shows that clinical resistant *E. coli* strain is resistant to Ampicillin and Trimethethoprim/Sulfamethoxazole (SXT). Thus, if a patient presents with an infection with this (or a similar strain), Ampicillin and Trimethethoprim/Sulfamethoxazole (SXT) should not be administered; instead, Imipenem, Ceftazidime, Gentamicin, Levofloxacin, Ciprofloxacin, and Cetriaxone should be administered.

These data show that the present invention is accurately able to differentiate an antimicrobial's MIC for a clinically-relevant strain of bacteria that is resistant to one or more antimicrobials and the antimicrobial's MIC for a strain of the same bacteria that is sensitive to the antimicrobial; thus, the present invention, in a greatly reduced amount of time relative to standard methods, can provide a patient with an appropriate treatment regimen, i.e., a specific antimicrobial and at a particular dosage.

Example 8

The Present Invention Provides Rapid and Accurate Determination of a Plurality of Antimicrobials' MICs for an Antimicrobial-Sensitive Bacterium In this example, the present invention was used to determine the MICs for a plurality of antimicrobials for an *S. aureus* strain that is antimicrobial sensitive.

*S. aureus* (QC strain 29213) was cultured under standard sterile conditions in Mueller-Hinton (MH) broth overnight at 37° C. with shaking. The *S. aureus* concentration from the overnight culture was then set to $5 \times 10^5$ CFU/ml using the McFarland standard technique for optical density readings at 600 nm. Concurrently, two sterile 96-well microplates were prepared with serial dilutions of a specified antimicrobial (see below) and a no-antimicrobial (saline) control, all in MH broth.

Figure 24:
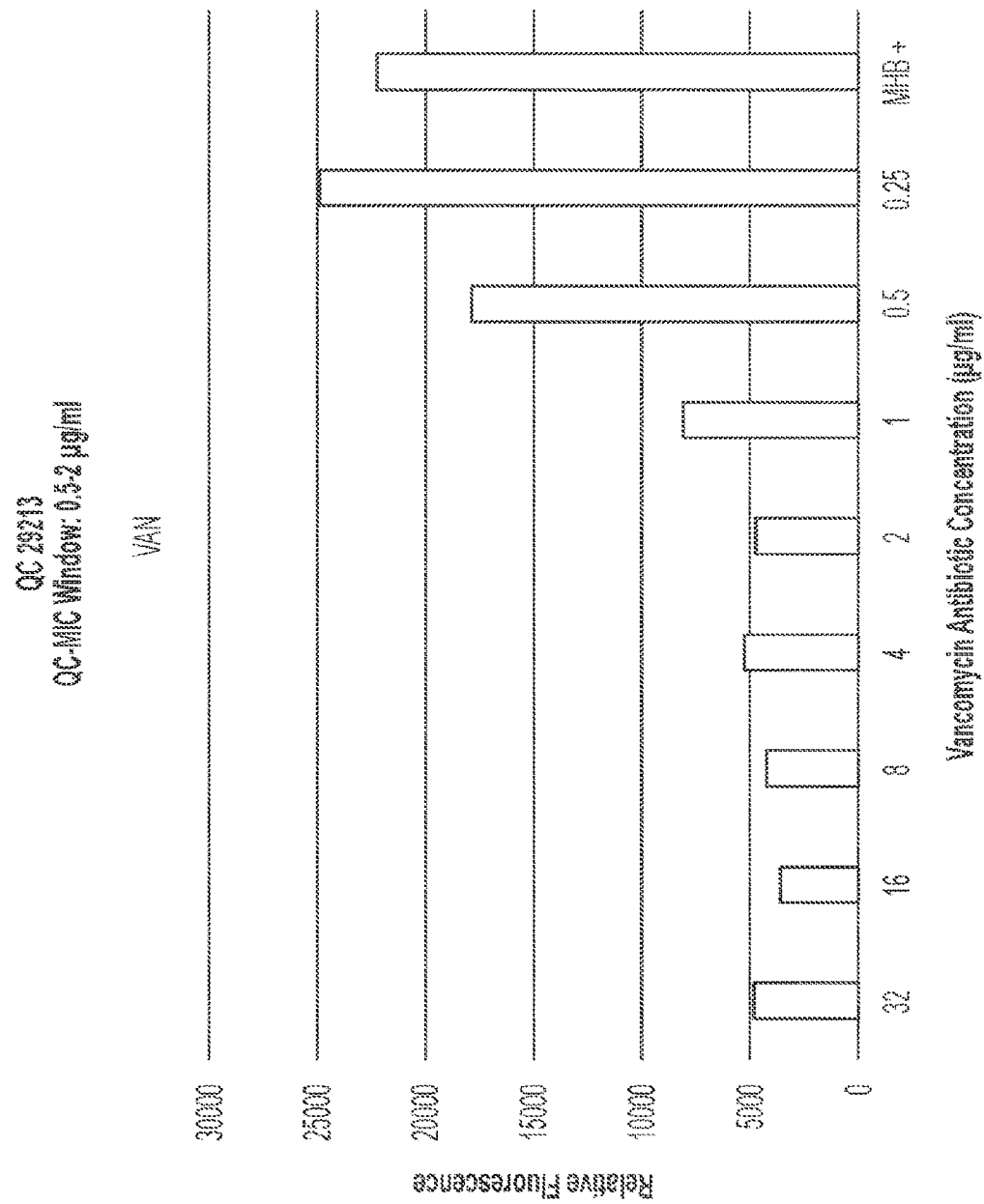
FIG. 24 to FIG. 26 are graphs comparing sensitives for a plurality of antimicrobials for a chemically sensitive *S. aureus* ("QC strain 29213") strain. The antimicrobials used are Vancomycin (FIG. 24); Penicillin (FIG. 25); and Teicoplanin (FIG. 26).

The microplates, each well containing 100 μL, were inoculated with the prepared antimicrobial dilutions and incubated at 37° C. for 3 hours, 45 minutes for determination using the present invention (the "fast-AST" technique). The "fast-AST" microplates were removed from the shaking incubator after 3 hours, 45 minutes and centrifuged for 2.5 minutes at 2500×g in order to pellet. The MH broth was then aspirated and 100 μL of 25 mM PBS was added to each well of both microplates. Then, 104 of the chemical moiety (here, Europium-Cryptate formulation) was added to each well (to 20 ng/well) and 10 μL of 0.005% Glutaraldehyde (as the signaling agent) was added to each well. The two microplates were then shaken at 300 rpm for 30 minutes. After, both plates were centrifuged for 2.5 minutes at 2500×g to pellet. The solution was aspirated and a wash of 200 μL, PBS-tween was added to each well, followed by a centrifugation to pellet. After aspiration of solution, a second identical wash of 200 μL PBS-tween occurred, followed by a final centrifugation to pellet. 200 μL PBS-tween was added to each well. The plate was then read using time resolved fluorescence on a BioTek H1 plate reader. This process was carried out with the following antimicrobial preparations: Vancomycin at diluted concentrations from 32 μg/ml to 0.25 μg/ml (FIG. 24); Penicillin at diluted concentrations from 8 μg/ml to 0.0625 μg/ml (FIG. 25); and Teicoplanin at diluted concentrations from 16 μg/ml to 0.0125 μg/ml (FIG. 26).

Figure 25:
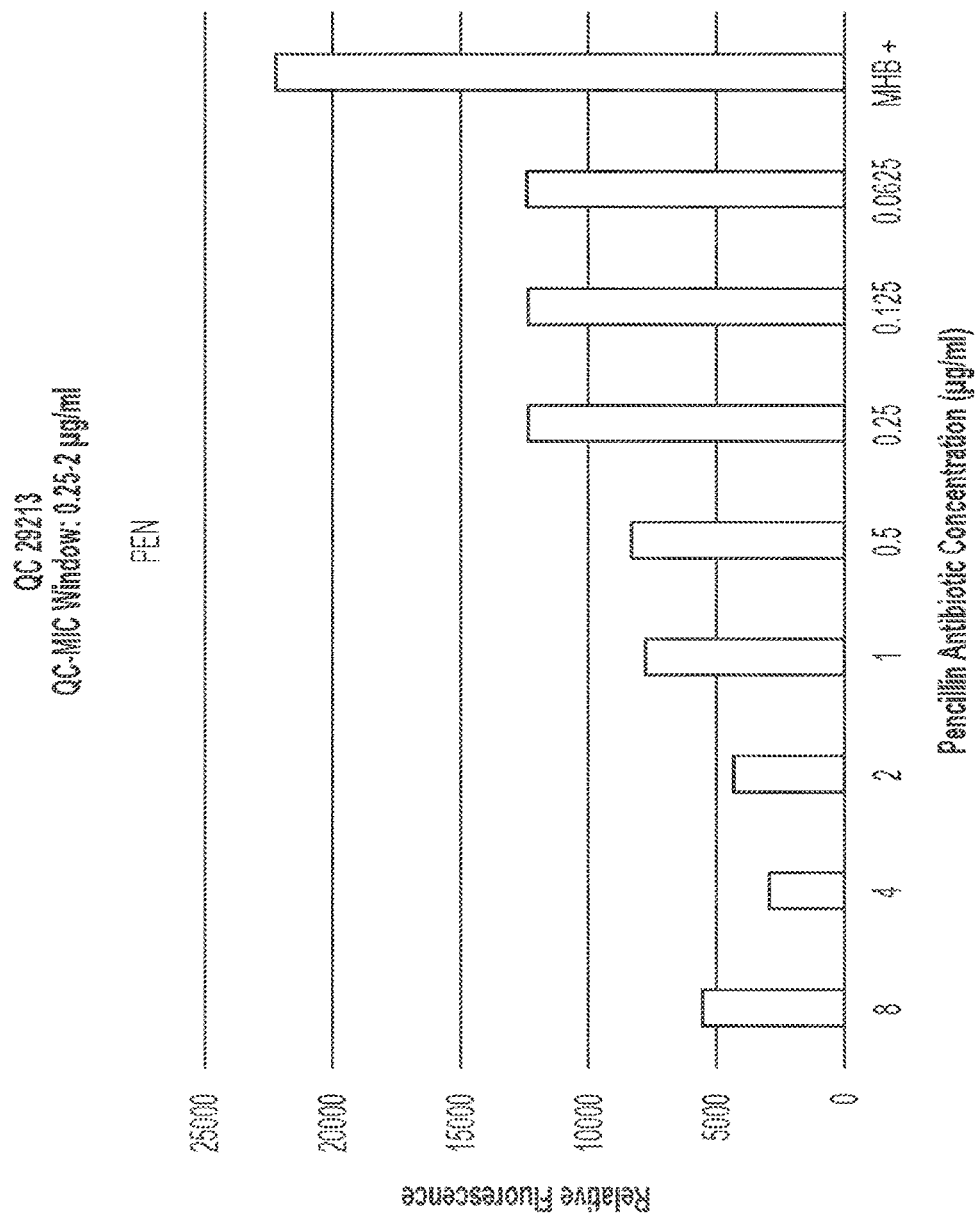
Figure 26:
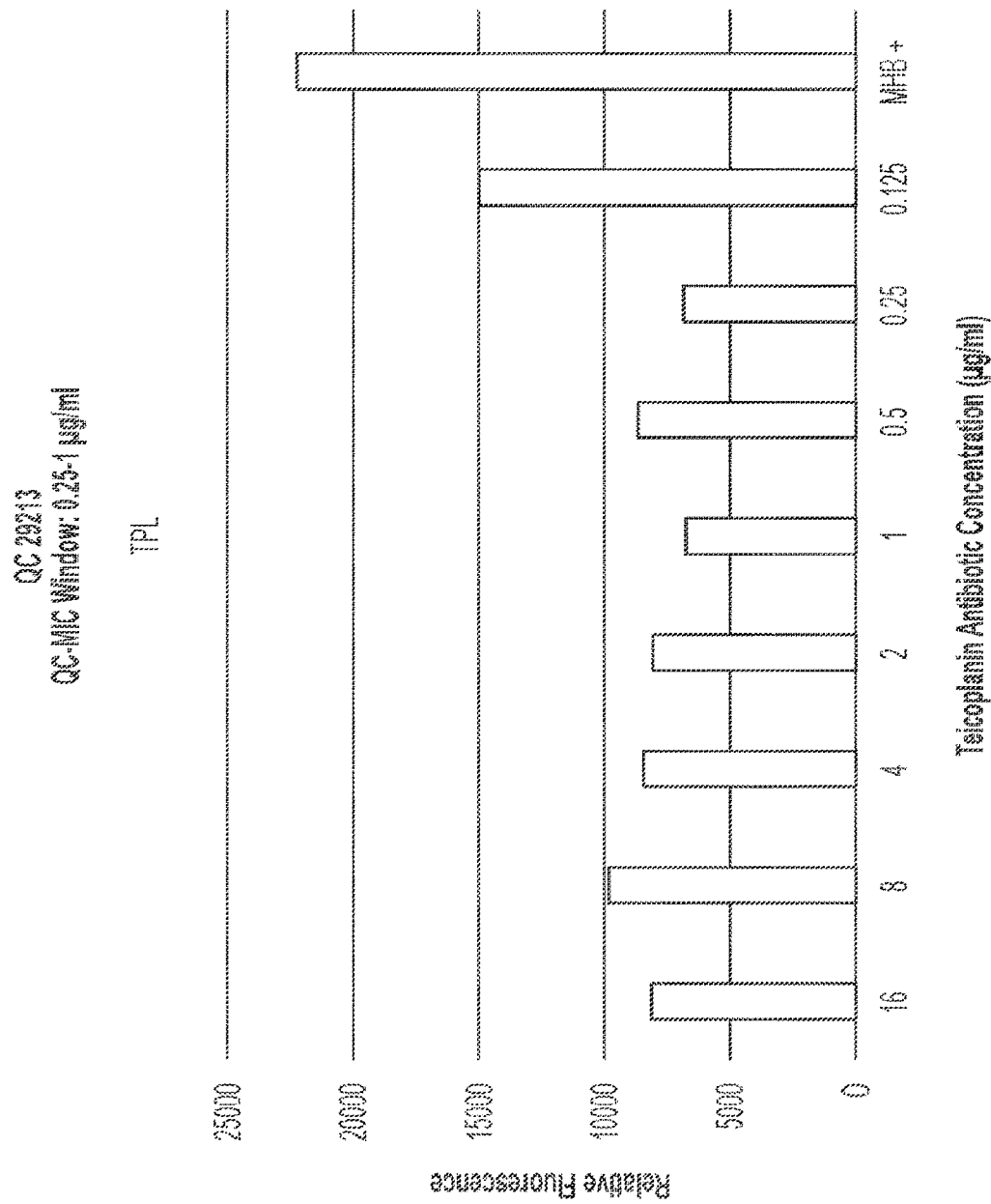

As seen in FIG. 24 to FIG. 26, *S. aureus* (QC strain 29213) the present invention determined MICs that were similar to those obtained from a standard CLSI reference method: Vancomycin: 0.5-2 μg/ml; Penicillin: 0.25-2 μg/ml; and Teicoplanin 0.25-1 μg/ml.

These data show that the present invention is accurately able to determine a plurality of antimicrobial's MICs; thus, the present invention, in a greatly reduced amount of time relative to standard methods, can provide a patient with an appropriate treatment regimen, i.e., a specific antimicrobial and at a particular dosage.

Example 9

The Present Invention Provides Rapid and Accurate Determination of an Antimicrobial's MIC Directly from Blood Culture Samples and without the Need for Sub-Culturing and an Overnight Growth Incubation In this example, the present invention was used for rapidly determining an antimicrobial's MIC directly from a blood culture sample.

One clinical sample for each of *E. coli*, *S. aureus*, and *K. pneumoniae* were obtained. The isolates were shipped on agar slants, sub-cultured, and stored at −80° C. The samples were removed from the freezer, allowed to warm to room temperature, and streaked on a 5% sheep blood-trypic soy agar (TSA) petri dish (ThermoFisher). The petri dish was placed in an incubator at 35° C. overnight. A single colony was picked and the streaking process was repeated on a new plate, followed by a second, 35° C. overnight incubation. A total of three to five colonies were picked and dispersed into 1 mL of sterile saline (Hardy Diagnostics) and the concentration was determined by optical density measurement at 600 nm (Molecular Devices M2). The sample was diluted in two steps to 2 CFU/ml in 40 mL of sterile cation adjusted Mueller Hinton Broth (MHB, Hardy Diagnostics) in a covered flask.

The flask was loaded into a shaker incubator overnight at 35° C. to mimic the performance of a BD BACTEC® blood culture system. The flask was put at 4° C. after 10 hours, at which point the *E. coli* concentration was determined to be $\sim 1 \times 10^8$ CFU/ml. This is the approximate concentration at which commercial blood culture systems, such as the BD BACTEC and bioMerieux BacT/Alert, register positive blood cultures. The 10-hour incubation time was determined by streaking blood culture samples on 5% sheep blood TSA-petri dishes, incubating these at 35° C. overnight, and determining the colony count.

The sub-culture "control" sample was taken by streaking this "positive" blood culture onto a TSA plate and incubating overnight at 35° C. A standard CLSI broth microdilution reference method was then performed, as described previously.

Centrifugation-based separation was then performed by following the SepsiTyper (Bruker Daltonics) protocol.

Briefly, 1 mL of lysis buffer (Bruker Daltonics) was added to 5 mL of the MHB broth with $1\times10^8$ CFU/ml *E. coli*. The mixture was aliquoted into six microfuge tubes, vortexed for 10 seconds, and then spun at 13,000 rpm for 2 min. The supernatant was removed and discarded, 1 mL of washing buffer (Bruker) was added to each tube, and the tubes were centrifuged at 13,000 rpm for 1 min. The supernatant was again removed and discarded. Each pellet was resuspended in 500 µL of sterile saline by pipetting up-and-down. The solutions were mixed and the bacteria concentration was determined using a Promega Bactitre-Glo™ bacteria cell viability kit.

Figure 27:
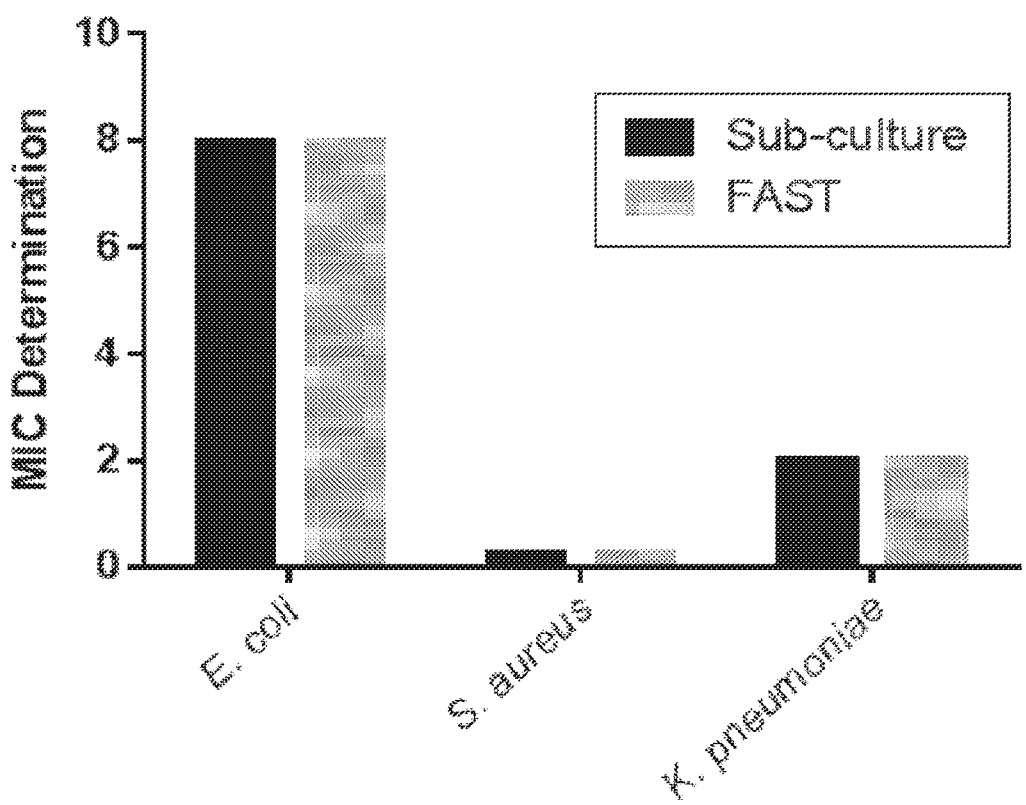
FIG. 27 and FIG. 28 are graphs showing MIC results using a method of the present invention directly on a clinical sample and compared to clinical results obtained with a Beckman-Coulter MicroScan Walkaway (in which a subculturing step is performed prior to overnight growth).
Figure 28:
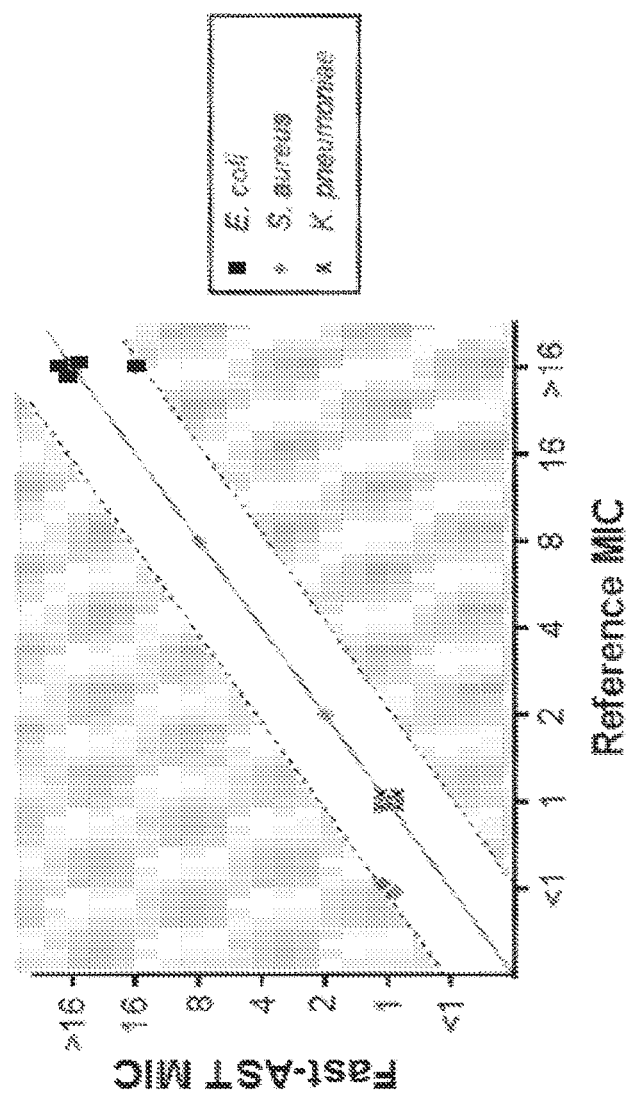

The samples were diluted into MHB at a concentration of $\sim5\times10^5$ CFU/ml. A "fast-AST" assay (as described in Example 2) was then performed, and the MIC determinations were compared. The "fast-AST" method on clinical samples provided similar MIC values as a standard method which requires sub-culturing, see, FIG. 27 and FIG. 28.

These data show that the present invention ("fast-AST" procedure), when used directly on clinical samples, provides consistent results with a standard MIC-determining method which requires a sub-culturing step prior to an overnight growth; thus, the present invention greatly reduces time before a patient is provided an appropriate treatment regimen, i.e., a specific antimicrobial and at a particular dosage.

Example 10

Streptavidin Conjugated to Europium Binds to Biotinylated Wheat Germ Agglutinin, which Specifically Binds to Gram Positive Bacteria In this example, Europium was used as a chemical moiety in signaling agents that comprise wheat germ agglutinin, which specifically binds to gram-positive bacteria.

Figure 29:
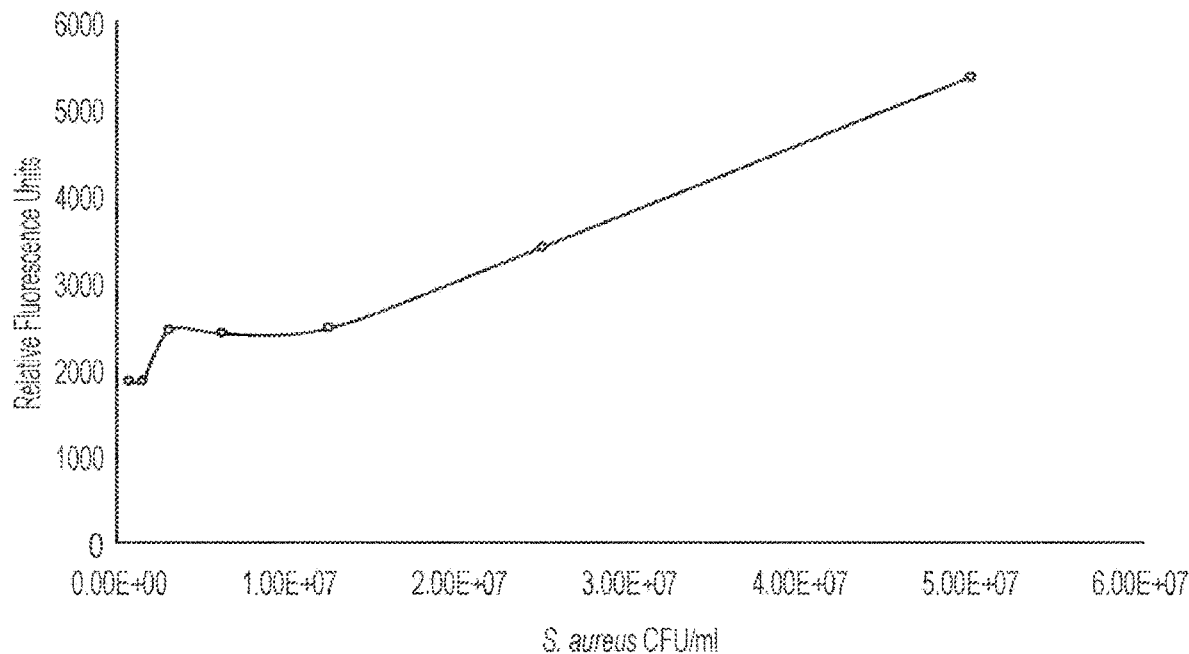
FIG. 29 is a graph showing the detected fluorescence (via a signaling agent comprising Europium and use of wheat germ agglutinin, which specifically binds gram positive bacteria) of a gram-positive bacterial solution relative to the concentration of bacteria in the solution.

Bacteria (*S. aureus*) were inoculated across a 96-well plate in concentrations ranging from $1\times10^5$ to $1\times10^9$ in MES buffer at pH 6. To each well containing the bacteria, and the corresponding control wells, 2 µg of biotinylated wheat germ agglutinin (Sigma) was added and the reaction solution was allowed to incubate for 15 minutes in order to facilitate the labeling of the exterior of the bacteria within the well with the chosen reporter. Then, a commercially-available streptavidin-Europium (e.g., from Perkin-Elmer) was added to a final concentration per well of 0.4 µg/ml. After incubation for a further 15 min, the test plate was centrifuged, using a Thermo Scientific Heraeus Multifuge X3, at a speed of 2500×g for 2.5 minutes in order to pellet the bacteria in the bottom of the plate while leaving any unassociated reporter in the supernatant. The plate was then aspirated, using a BioTek Multiflo X plate washer, to remove the supernatant and unreacted reporter, before the addition of wash buffer. This wash procedure was repeated two additional times in order to thoroughly remove any unreacted reporter. Finally, to the aspirated wells, was added the reading buffer before the addition of Delfia Enhancement Solution. The plate was then incubated for 15 minutes to allow for the europium enhancement before measurement of the europium using time resolved fluorescence on a BioTek H1 plate reader, as shown in FIG. 29.

These data show that the use of Europium as a chemical moiety in a signaling agent is accurately able to quantify bacterial concentrations in a solution.

Example 11

Streptavidin Conjugated to Europium Binds to Biotinylated Polymixin B, which Specifically Binds to Gram Negative Bacteria In this example, Europium was used as a chemical moiety in signaling agents that comprise Polymixin B, which specifically binds to gram-negative bacteria.

Figure 30:
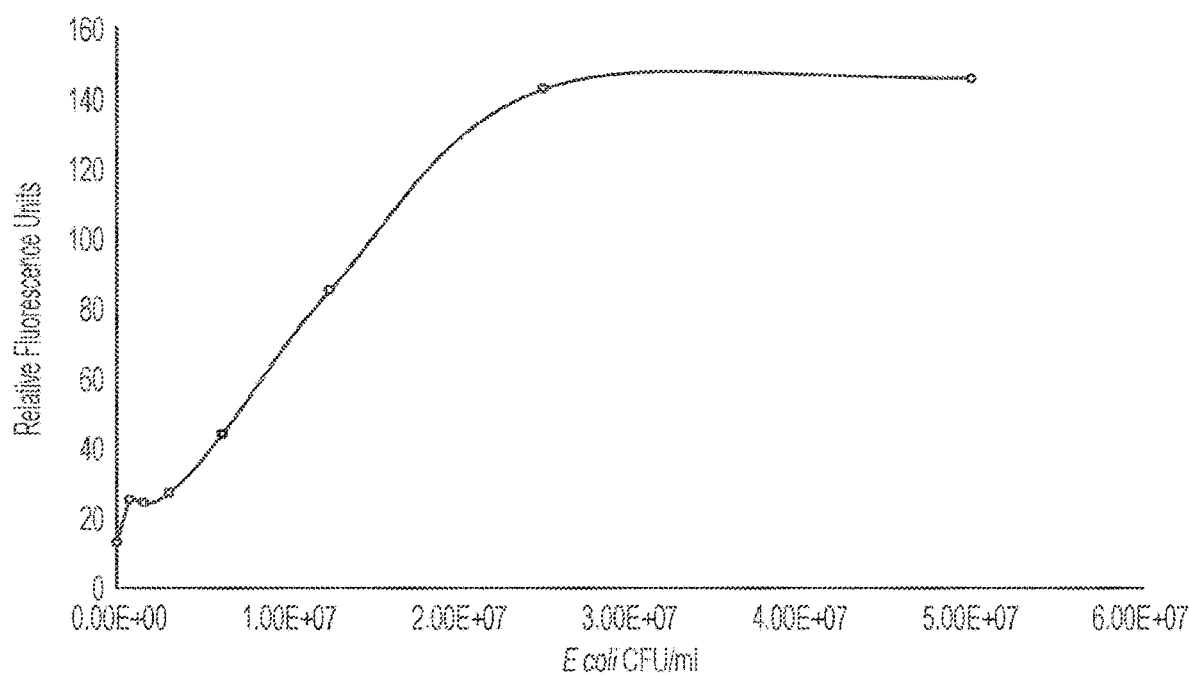
FIG. 30 is a graph showing the detected fluorescence (via a signaling agent comprising Europium and use of Polymixin B, which specifically binds gram negative bacteria) of a gram-negative bacterial solution relative to the concentration of bacteria in the solution.

Bacteria (*E coli*) were inoculated across a 96-well plate in concentrations ranging from $1\times10^5$ to $1\times10^9$ in MES buffer at pH 6. To each well containing the bacteria, and the corresponding control wells, biotinylated polymixin (Hycult Biosciences) was added for a final dilution of 1:200 and the reaction solution was allowed to incubate for 15 minutes in order to facilitate the labeling of the exterior of the bacteria within the well with the chosen reporter. Then, a commercially-available streptavidin-Europium (e.g., from Perkin-Elmer) was added to a final concentration per well of 0.4 µg/ml. After incubation for a further 15 min, the test plate was centrifuged, using a Thermo Scientific Heraeus Multifuge X3, at a speed of 2500×g for 2.5 minutes in order to pellet the bacteria in the bottom of the plate while leaving any unassociated reporter in the supernatant. The plate was then aspirated, using a BioTek Multiflo X plate washer, to remove the supernatant and unreacted reporter, before the addition of wash buffer. This wash procedure was repeated two additional times in order to thoroughly remove any unreacted reporter. Finally, to the aspirated wells, was added the reading buffer before the addition of Delfia Enhancement Solution. The plate was then incubated for 15 minutes to allow for the europium enhancement before measurement of the europium using time resolved fluorescence on a BioTek H1 plate reader, as shown in FIG. 30.

These data show that the use of Europium as a chemical moiety in a signaling agent is accurately able to quantify bacterial concentrations in a solution.

Example 12

Europium Detector Provides Larger Signal Range and, Therefore, More Accurate MIC Data This example compared the ability of Europium and HRP, as chemical moieties in signaling agents (comprising an antibody that specifically binds to bacteria) to accurately determining MICs.

Using 96-well plates containing cation-adjusted Mueller Hinton broth and appropriate antimicrobial dilutions, bacteria were prepared by diluting colonies into saline to reach a McFarland value of 0.5, which was verified using a spectrophotometer. This was diluted 1:20 into saline and 10 µl of inoculum was added to each well. Bacterial antimicrobial testing plates were incubated at 35° C., shaking at 150 rpm for 3 hours and 45 minutes. After this incubation, cationic magnetic beads and anti-*S. aureus* antibodies (conjugated to either horseradish peroxidase or Europium; custom conjugation performed by Cisbio Assays) were added to each well and incubated for 20 minutes. Using an automated plate washer, magnetic beads were captured and the contents of each well were washed three times with PBS-Tween20 (0.1%). Then, wells were imaged directly using time resolved fluorescence (Europium) or TMB was added and allowed to incubate for 15 minutes, after which the reaction was stopped by addition of 1 M sulfuric acid and absorbance at 450 nm was measured for each well.

Figure 31:
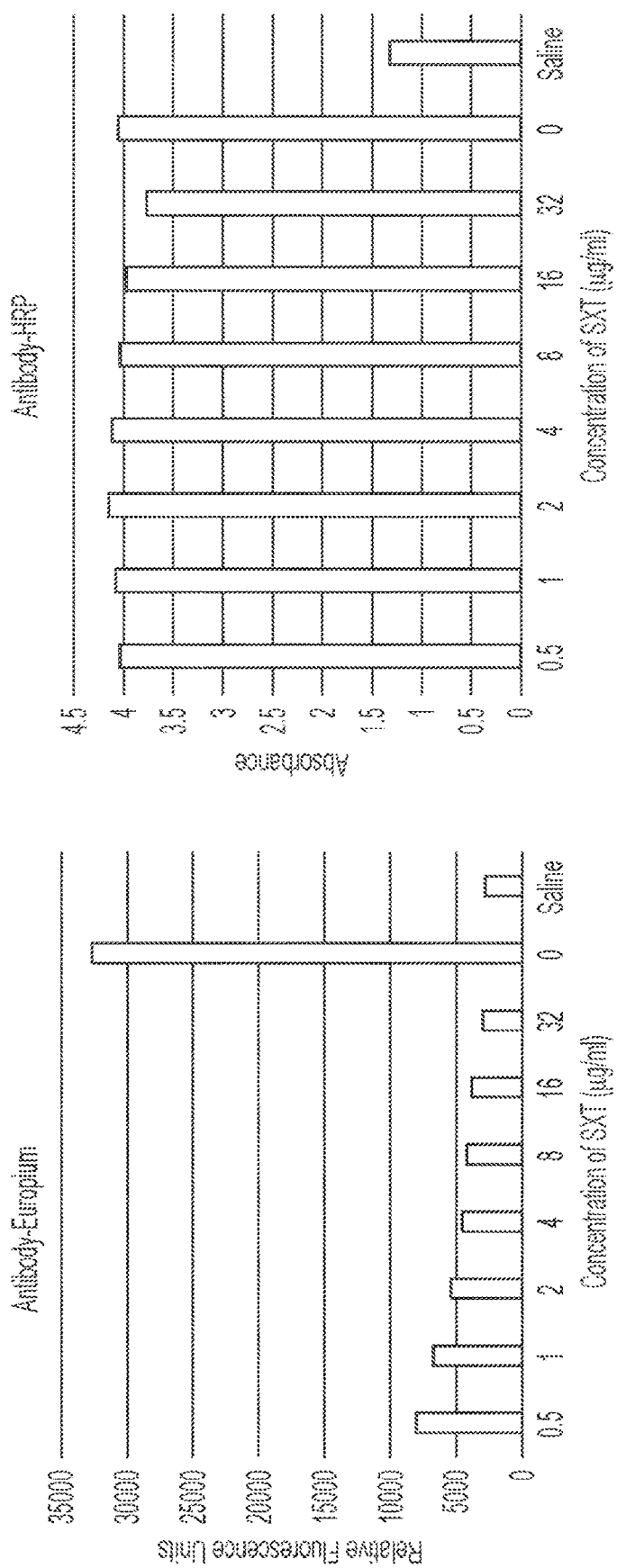
FIG. 31 are graphs that compare MIC values obtained when an antibody-bound Europium formulation is used as signaling agent to MIC values obtained when an antibody-horse radish peroxidase (HRP) is used as signaling agent. The MIC for SXT for this clinical *S. aureus* strain was ≤0.5 µg/ml by CLSI overnight method.

As shown in FIG. 31, using Europium as chemical moiety determined SXT's MIC more accurately than the MIC determined using HRP as chemical moiety.

These data show that the use of Europium as a chemical moiety in a signaling agent is accurately able to determine an antimicrobial's MIC.

Example 13

Embodiments of Europium Formulations, which Non-Specifically Label Bacteria, are Effective at Detecting Bacteria and Quantifying Bacteria Concentrations In this example, Europium formulations are non-specifically bound to bacteria.

Bacteria (*E coli*) were inoculated across a 96-well plate in concentrations ranging from 1e5 to 1e9 in MES buffer at pH 6 (Europium Cryptate-diamine) or HEPES pH 7.5 (EuropiumN1-amino). To each well containing the bacteria, and the corresponding control wells, EuropiumCryptate-diamine (Compound (3); Cisbio) or Europium N1-amino (Compound (6); PerkinElmer) was added at 66 ng/well, then EDC/NHS (at 0.1 and 0.3 mg/ml) or glutaraldehyde (0.5% final concentration) were added as indicated.

(3)

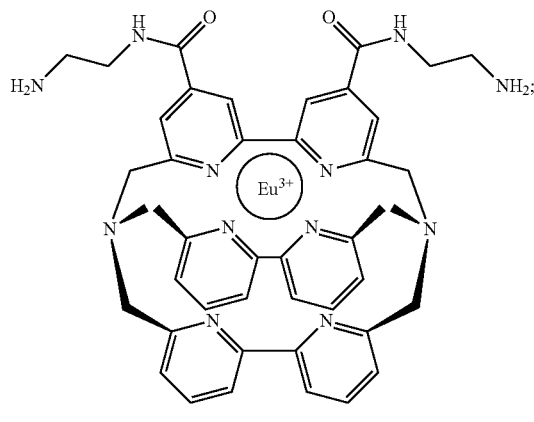

Europium-cryptate-diamine (Eu-Cryptate-diamine)

(6)

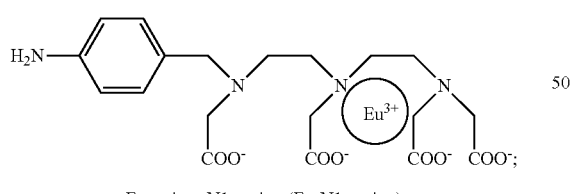

Europium-N1-amino (Eu-N1-amino)

Figure 32:
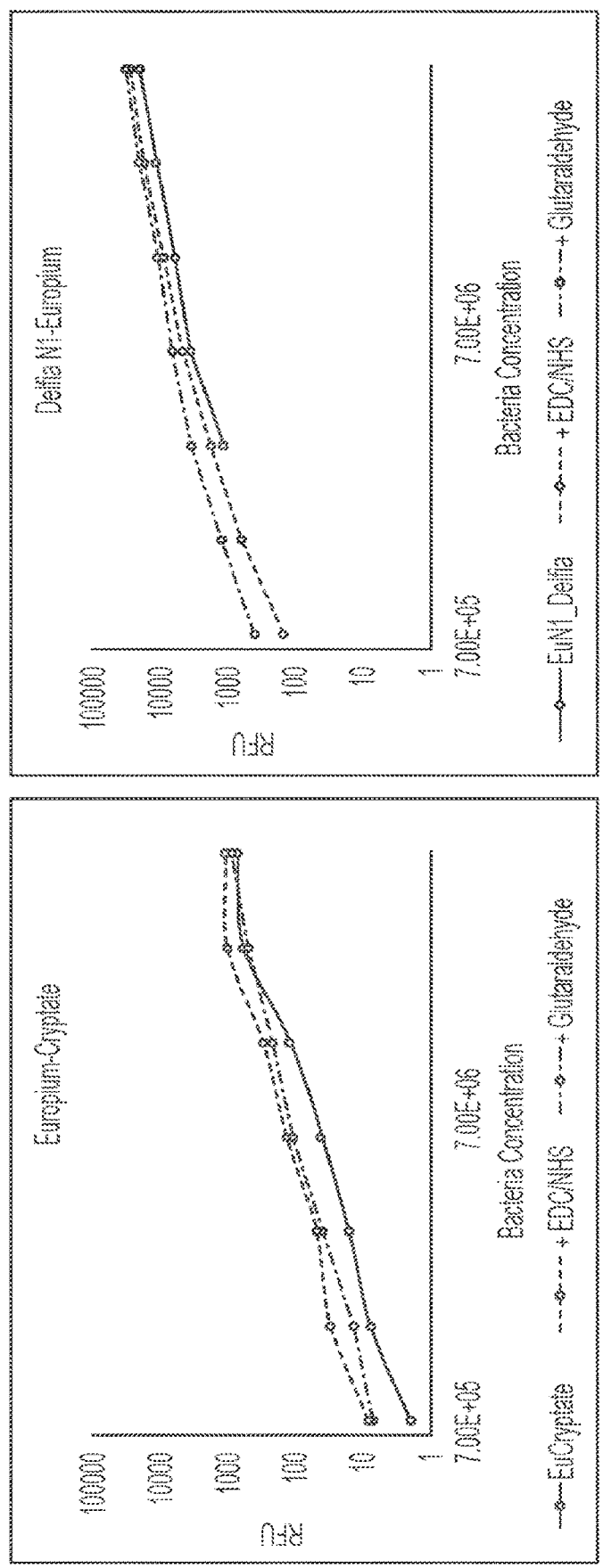
FIG. 32 are graphs showing the relative fluorescence units (RFU) obtained for specific bacterial concentrations for two Europium formulations that are non-specifically bound to bacterial surfaces.

The reaction solution was allowed to incubate for 30 minutes in order to facilitate the labeling of the exterior of the bacteria within the well with the chosen reporter. Then, the test plate was centrifuged, using a Thermo Scientific Heraeus Multifuge X3, at a speed of 2500×g for 2.5 minutes in order to pellet the bacteria in the bottom of the plate while leaving any unassociated reporter in the supernatant. The plate was then aspirated, using a BioTek Multiflo X plate washer, to remove the supernatant and unreacted reporter, before the addition of wash buffer. This wash procedure was repeated one (Eu-Cryptate-diamine) or two (EuropiumN1-amino) additional times in order to thoroughly remove any unreacted reporter. Wells containing Europium Cryptate-diamine were reconstituted in reading buffer and read using time resolved fluorescence on a BioTek H1 plate reader, as shown in FIG. 32. Finally, to the aspirated wells treated with Europium N1-amino, was added the reading buffer before the addition of Delfia Enhancement Solution. The plate was then incubated for 15 minutes to allow for the europium enhancement before measurement of the europium using time resolved fluorescence on a BioTek H1 plate reader, as shown in FIG. 32.

These data show that Europium formulations are accurately able to quantify bacterial concentrations in a solution when the Europium formulations are non-specifically bound to bacteria.

Example 14

Europium can be Attached to Amines via Isothiocyanate or to Carboxylic Acids via NH2 for Non-Specifically Labeling Bacteria when Quantifying Bacteria Concentrations In this example, Europium formulations are non-specifically bound to bacteria.

*Klebsiella pneumoniae* or *E. coli* were inoculated across a 96-well plate in concentrations ranging from $1 \times 10^5$ to $1 \times 10^9$ in MES buffer at pH 6 (Europium Cryptate-diamine; Compound (3)) or HEPES pH 7.5 (EuropiumITC; Compound (4)). To each well containing the bacteria, and the corresponding control wells, Europium Cryptate-diamine (Cisbio) or Europium ITC (PerkinElmer) was added at 66 ng/well, then EDC/NHS (at 0.1 and 0.3 mg/ml) to wells containing Europium Cryptate.

(3)

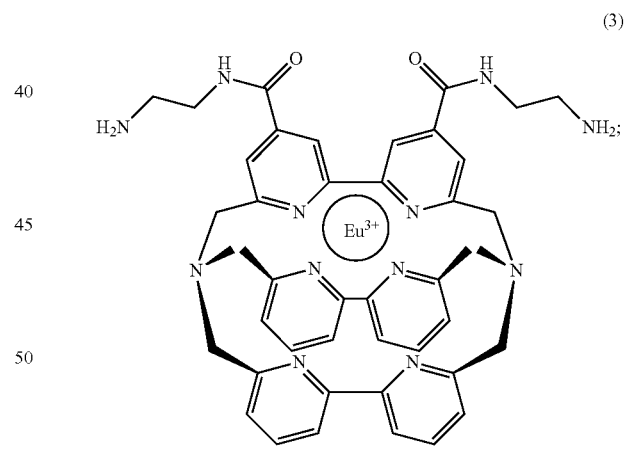

Europium-cryptate-diamine (Eu-Cryptate-diamine)

(4)

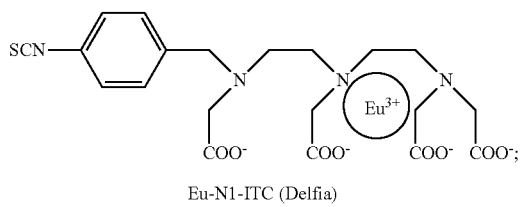

Eu-N1-ITC (Delfia)

Figure 33:
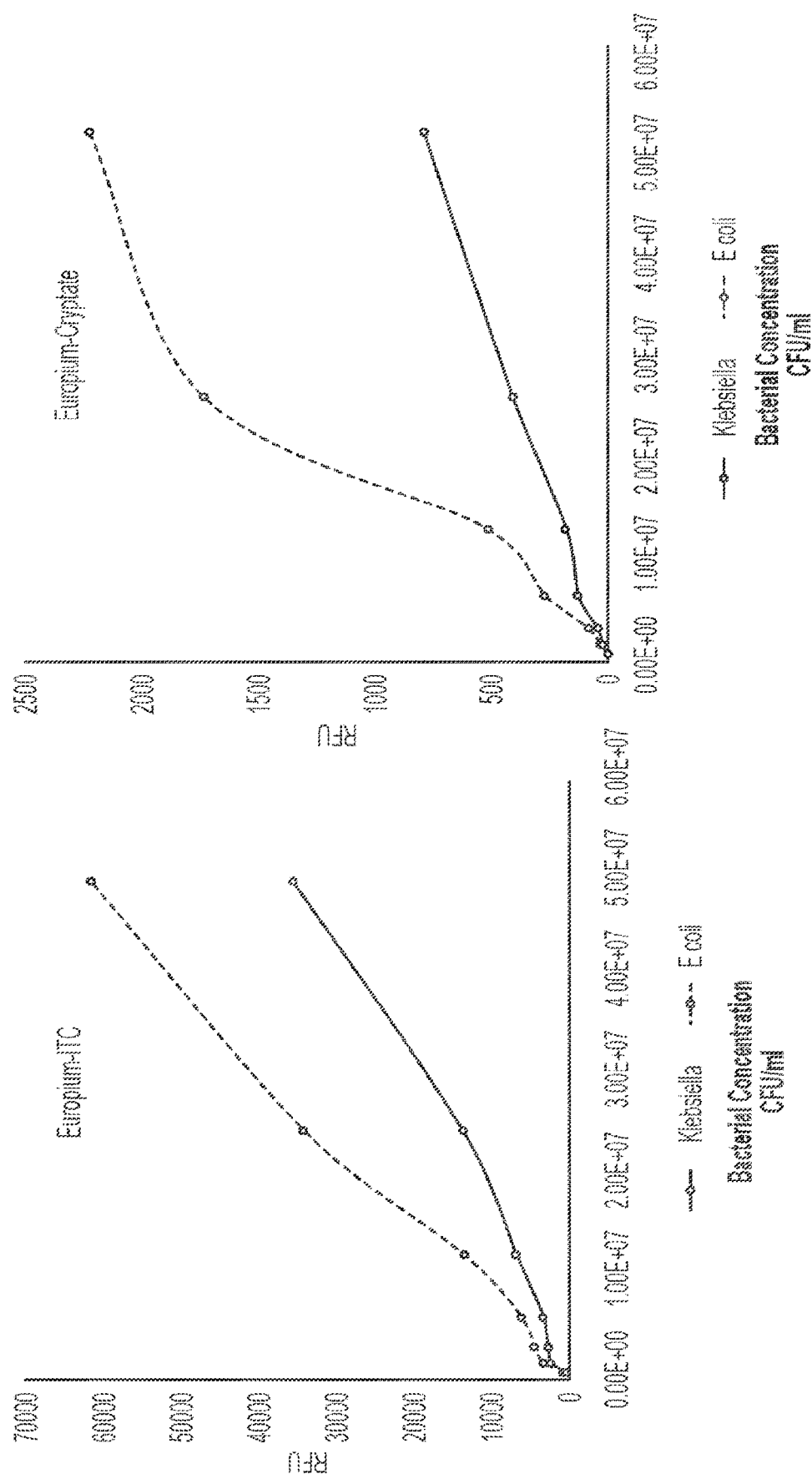
FIG. 33 are graphs showing the RFU obtained for specific bacterial concentrations of two bacterial species for two Europium formulations that are non-specifically bound to bacterial surfaces.

The reaction solution was allowed to incubate for 30 minutes in order to facilitate the labeling of the exterior of the bacteria within the well with the chosen reporter. Then, the test plate was centrifuged, using a Thermo Scientific Heraeus Multifuge X3, at a speed of 2500×g for 2.5 minutes in order to pellet the bacteria in the bottom of the plate while leaving any unassociated reporter in the supernatant. The plate was then aspirated, using a BioTek Multiflo X plate washer, to remove the supernatant and unreacted reporter, before the addition of wash buffer. This wash procedure was repeated one (EuropiumCryptate-diamine) or two (PerkinElmer) additional times in order to thoroughly remove any unreacted reporter. Wells containing EuropiumCryptate-diamine were reconstituted in reading buffer and read using time resolved fluorescence on a BioTek H1 plate reader, as shown in FIG. 33. Finally, to the aspirated wells treated with Eu—N1, was added the reading buffer before the addition of Delfia Enhancement Solution. The plate was then incubated for 15 minutes to allow for the europium enhancement before measurement of the europium using time resolved fluorescence on a BioTek H1 plate reader, as shown in FIG. 33.

These data show that Europium formulations are accurately able to quantify bacterial concentrations in a solution when the Europium formulations are non-specifically bound to bacteria.

Example 15

Glutaraldehyde can be Used to Non-Specifically Link Europium-Cryptate to the Bacterial Surface In this example, Europium formulations are non-specifically bound to bacteria with glutaraldehyde.

*Klebsiella pneumoniae, E coli*, or *Staph aureus* were inoculated across a 96-well plate in concentrations ranging from $1\times10^5$ to $1\times10^9$ in MES buffer at pH 6. To each well containing the bacteria, and the corresponding control wells, Europium Cryptate-diamine (Compound (3); Cisbio) was added at 66 ng/well, then a 5% solution of glutaraldehyde to wells containing Europium Cryptate.

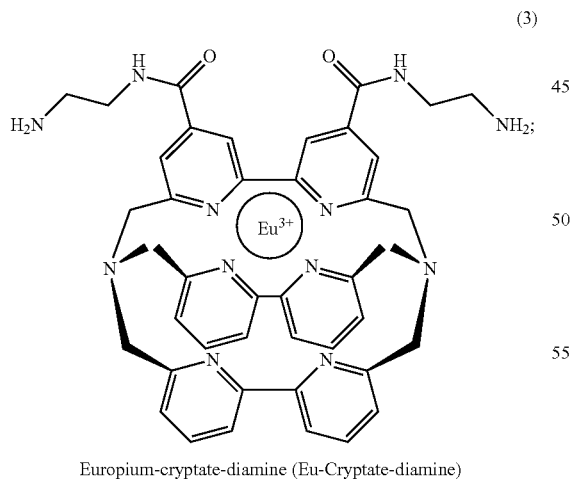

Europium-cryptate-diamine (Eu-Cryptate-diamine)

Figure 34:
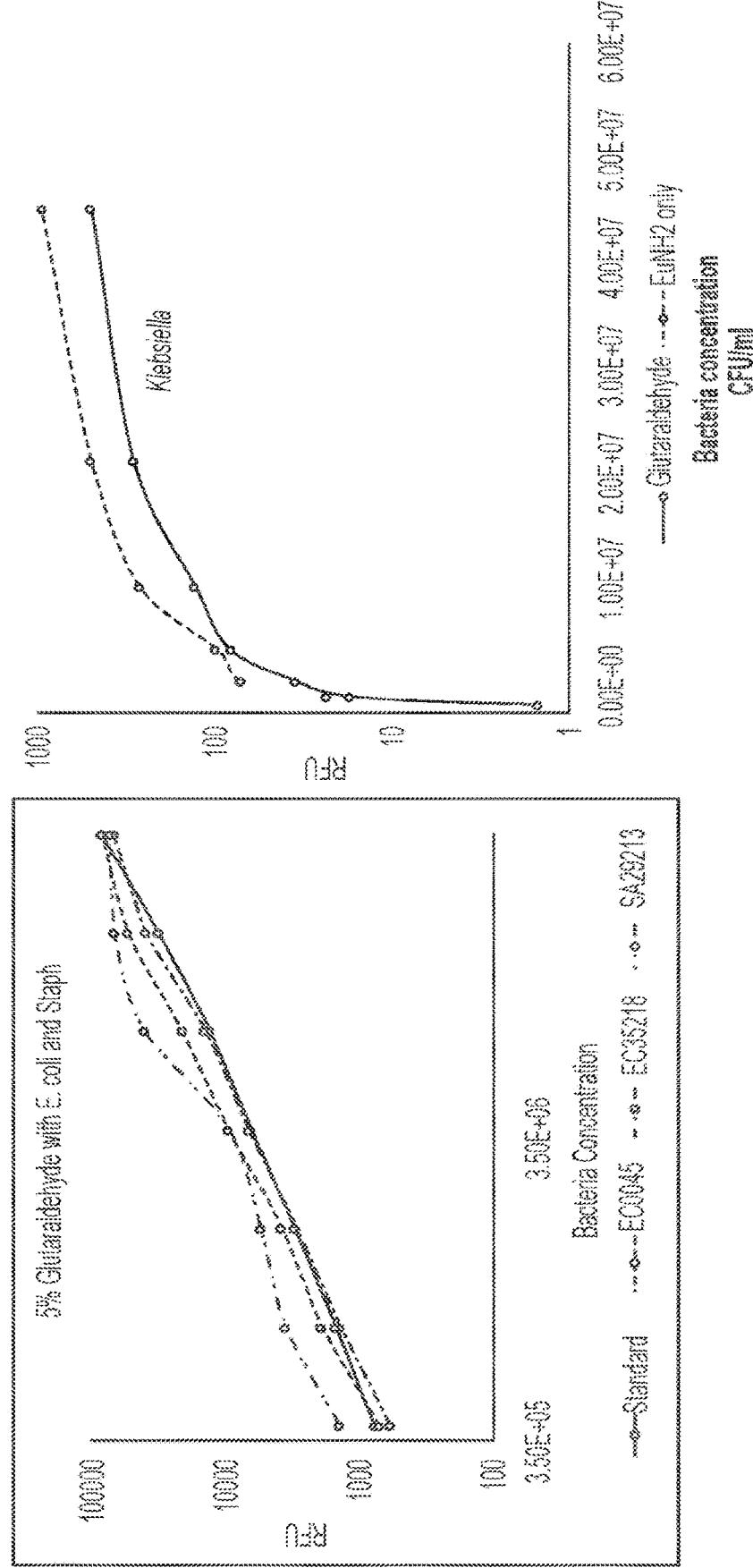
FIG. 34 and FIG. 35 are graphs showing the RFU obtained for specific bacterial concentrations of various bacterial species for a Europium formulation that is non-specifically bound to bacterial surfaces.

The reaction solution was allowed to incubate for 30 minutes in order to facilitate the labeling of the exterior of the bacteria within the well with the chosen reporter. Then, the test plate was centrifuged, using a Thermo Scientific Heraeus Multifuge X3, at a speed of 2500×g for 2.5 minutes in order to pellet the bacteria in the bottom of the plate while leaving any unassociated reporter in the supernatant. The plate was then aspirated, using a BioTek Multiflo X plate washer, to remove the supernatant and unreacted reporter, before the addition of wash buffer. This wash procedure was repeated once to thoroughly remove any unreacted reporter. Wells containing EuropiumCryptate-diamine were reconstituted in reading buffer and read using time resolved fluorescence on a BioTek H1 plate reader, as shown in FIG. 34.

These data show that Europium formulations are accurately able to quantify bacterial concentrations in a solution when the Europium formulations are non-specifically bound to bacteria.

Example 16

EDC/NHS can be Used to Non-Specifically Couple Europium-Cryptate to the Bacterial Surface In this example, Europium formulations are non-specifically bound to bacteria with EDC/NHS.

*Klebsiella pneumoniae* or *E coli* were inoculated across a 96-well plate in concentrations ranging from $1\times10^5$ to $1\times10^9$ in MES buffer at pH 6. To each well containing the bacteria, and the corresponding control wells, EuropiumCryptate-diamine (Compound (3); Cisbio) was added at 66 ng/well, then EDC/NHS (at 0.1 and 0.3 mg/ml) to wells containing Europium Cryptate.

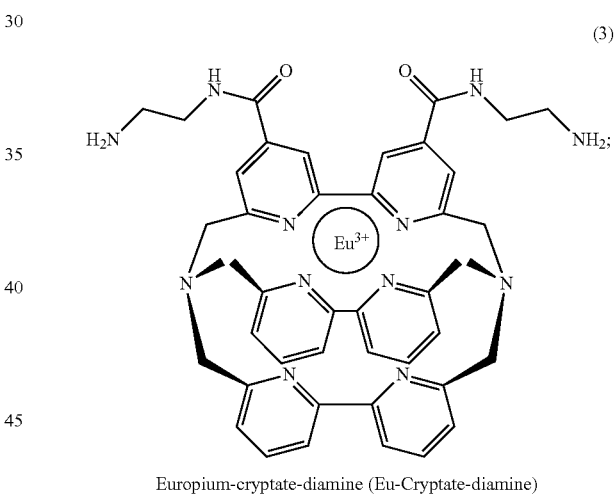

Europium-cryptate-diamine (Eu-Cryptate-diamine)

Figure 35:
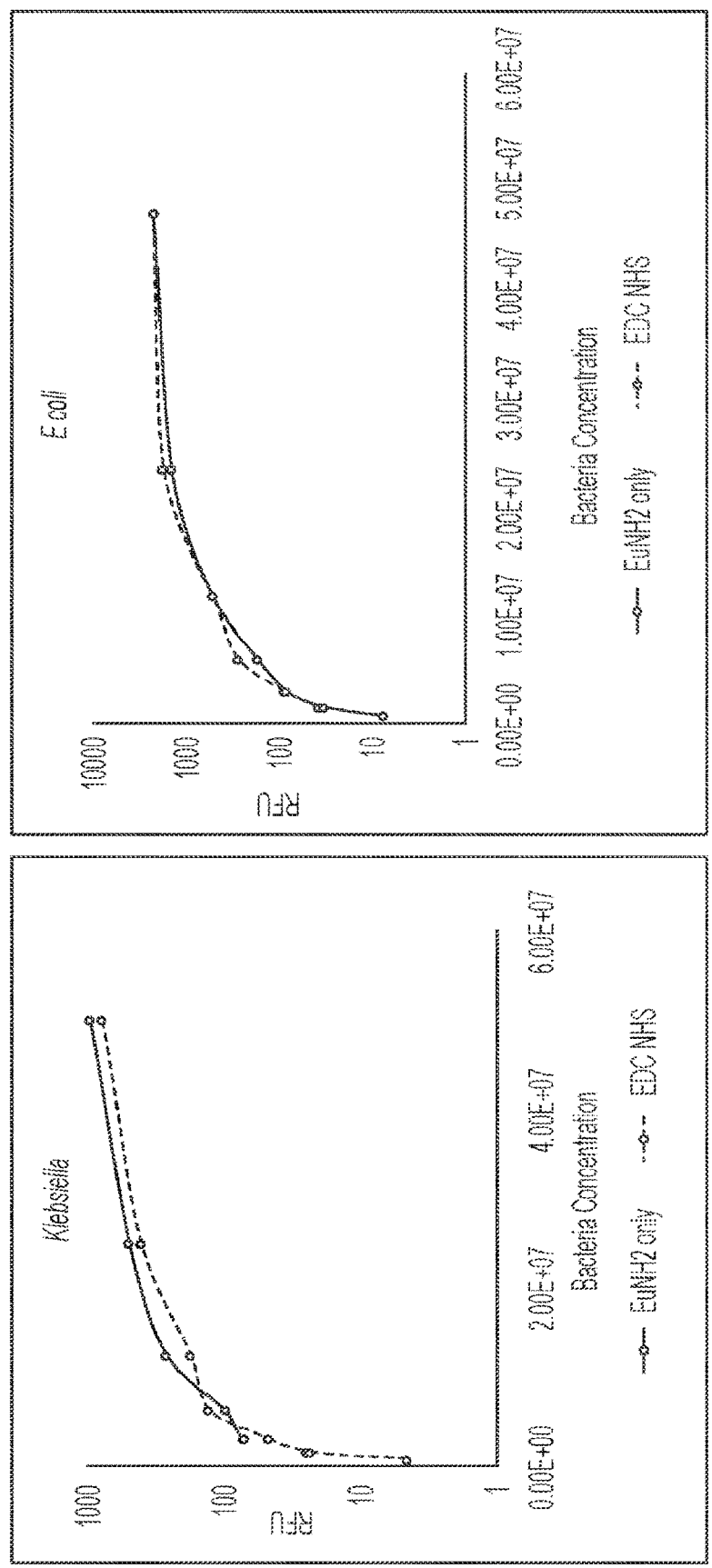

The reaction solution was allowed to incubate for 30 minutes in order to facilitate the labeling of the exterior of the bacteria within the well with the chosen reporter. Then, the test plate was centrifuged, using a Thermo Scientific Heraeus Multifuge X3, at a speed of 2500×g for 2.5 minutes in order to pellet the bacteria in the bottom of the plate while leaving any unassociated reporter in the supernatant. The plate was then aspirated, using a BioTek Multiflo X plate washer, to remove the supernatant and unreacted reporter, before the addition of wash buffer. This wash procedure was repeated once to thoroughly remove any unreacted reporter. Wells containing EuropiumCryptate-diamine were reconstituted in reading buffer and read using time resolved fluorescence on a BioTek H1 plate reader, as shown in FIG. 35.

These data show that Europium formulations are accurately able to quantify bacterial concentrations in a solution when the Europium formulations are non-specifically bound to bacteria.

Example 17

Effect of Glutaraldehyde Wash Cycles on Non-Specifically, Cryptate Labeled Bacteria In this example, Europium formulations are non-specifically bound to bacteria with various washes comprising glutaraldehyde.

*E coli* or *Staph aureus* were inoculated across a 96-well plate in concentrations ranging from $1\times10^5$ to $1\times10^9$ in MES buffer at pH 6. To each well containing the bacteria, and the corresponding control wells, EuropiumCryptate-diamine (Compound (3); Cisbio) was added at 66 ng/well, then a 5% solution of glutaraldehyde to wells containing Europium Cryptate.

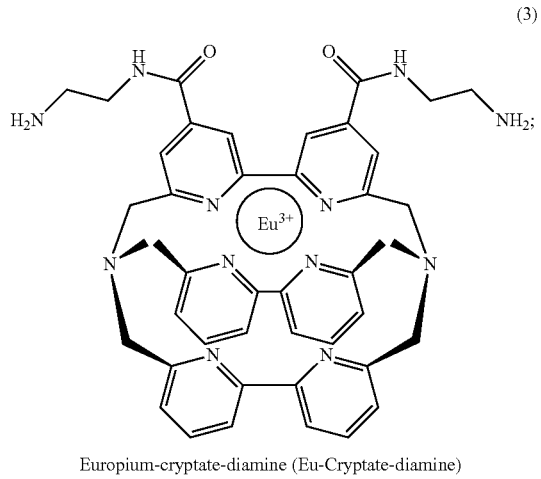

Europium-cryptate-diamine (Eu-Cryptate-diamine) (3)

Figures 36A, 36B:
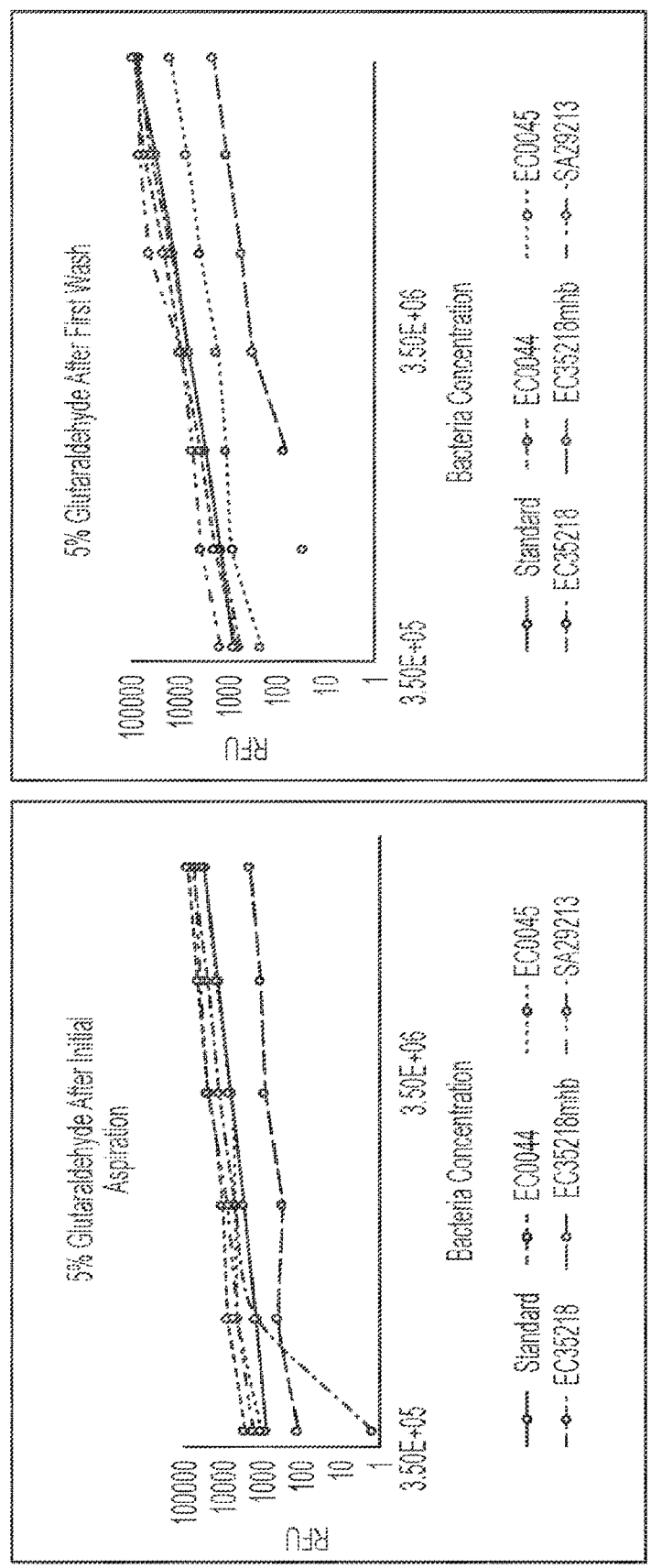
FIG. 36A to FIG. 36C are graphs showing the RFU obtained for specific bacterial concentrations of various bacterial species for a Europium formulation that is non-specifically bound to bacterial surfaces when using various washes comprising glutaraldehyde.
Figure 36C:
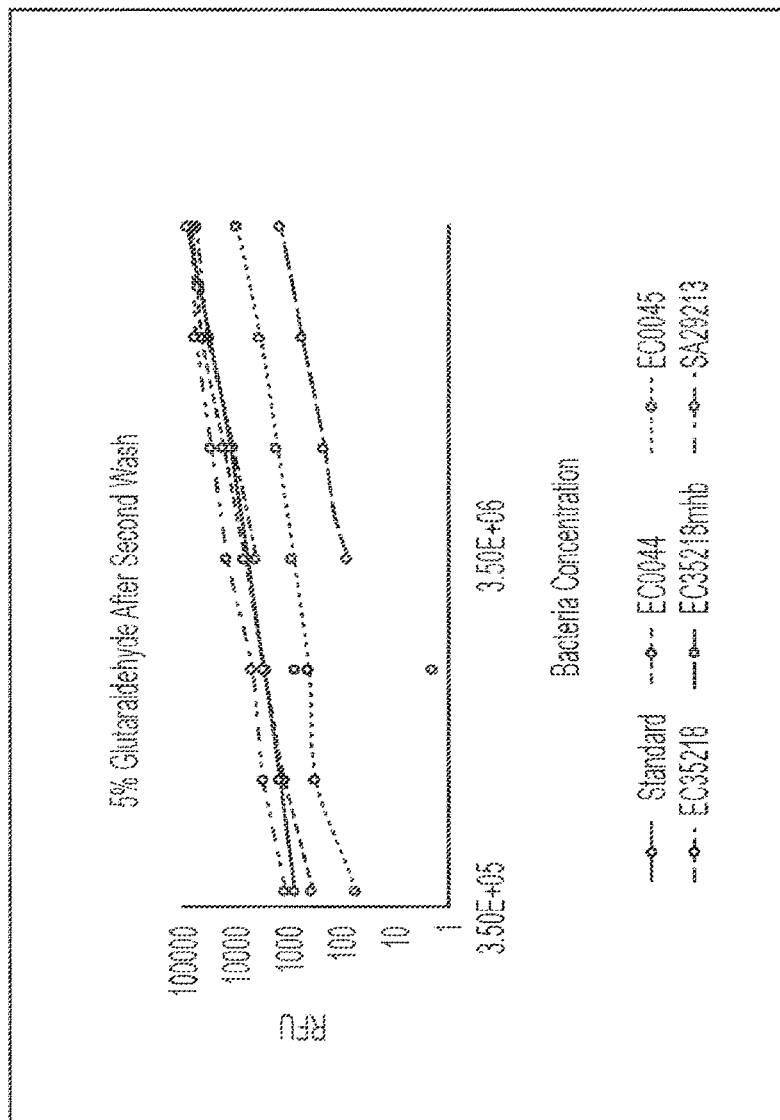

The reaction solution was allowed to incubate for 30 minutes in order to facilitate the labeling of the exterior of the bacteria within the well with the chosen reporter. Then, the test plate was centrifuged, using a Thermo Scientific Heraeus Multifuge X3, at a speed of 2500×g for 2.5 minutes in order to pellet the bacteria in the bottom of the plate while leaving any unassociated reporter in the supernatant. The plate was then aspirated, using a BioTek Multiflo X plate washer, to remove the supernatant and unreacted reporter, before the addition of wash buffer. This wash procedure was repeated twice to investigate the effect of multiple washes on overall data quality. Wells containing EuropiumCryptate-diamine were reconstituted in reading buffer and read using time resolved fluorescence on a BioTek H1 plate reader, as shown in FIG. 36A to FIG. 36C.

These data show that Europium formulations can be non-specifically bound to bacteria using various washes comprising glutaraldehyde.

Example 18

A Two-Step Tagging Process Using $NH_2$-PEG-Biotin Followed by Streptavidin-Europium (Eu-SAv) can Non-Specifically Label Bacteria In this example, Europium formulations are non-specifically bound to bacteria using a two-step process.

Figure 37:
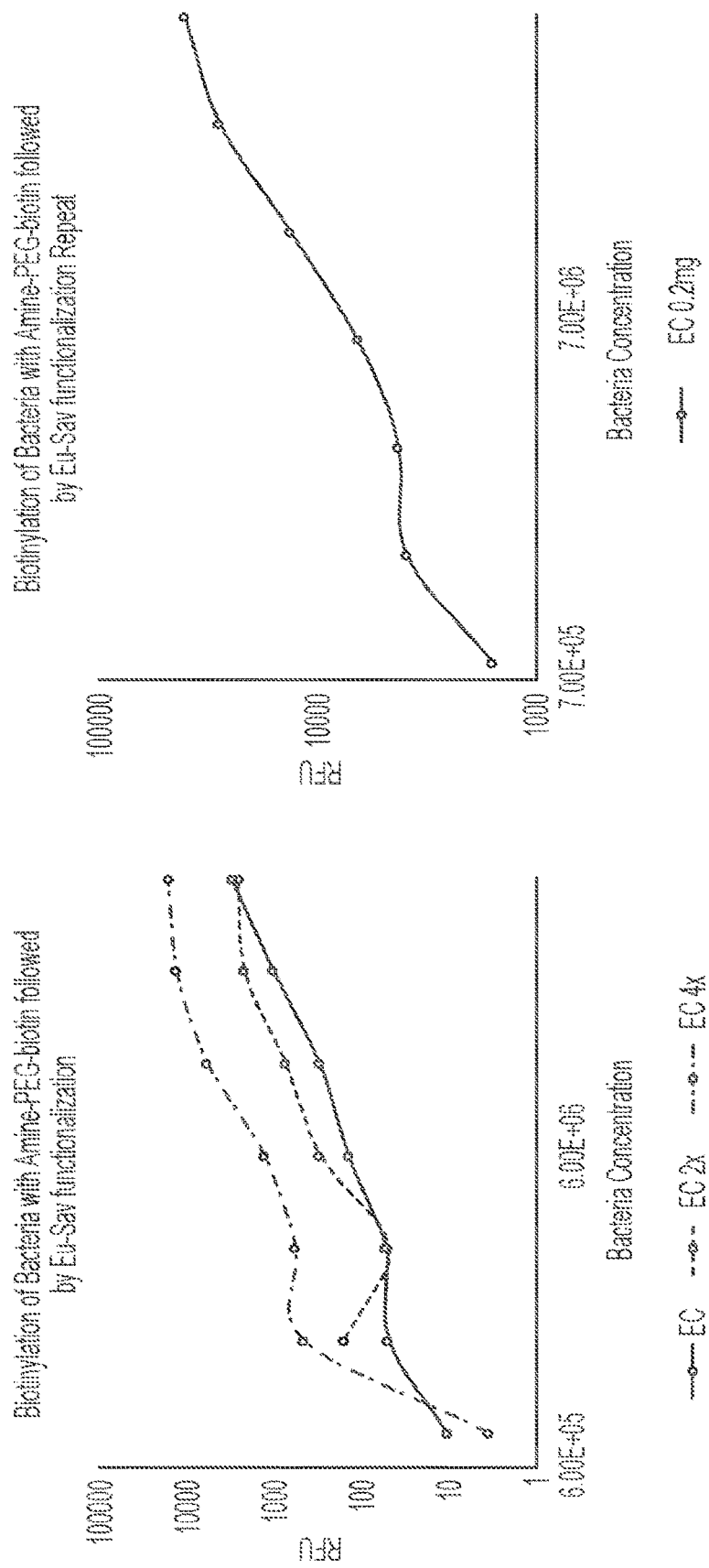
FIG. 37 are graphs showing the RFU obtained for specific bacterial concentrations of *E. coli* for a Europium formulation that is non-specifically bound to bacterial surfaces using a two-step process comprising NH2-PEG-Biotin followed by streptavidin-europium (Eu-SAv).

*E coli* was inoculated across a 96-well plate in concentrations ranging from $1\times10^5$ to $1\times10^9$ in MES buffer at pH 6. To each well containing the bacteria, and the corresponding control wells, Amine-PEG-Biotin (Laysan Bio) was added at 1 mg/well, then EDC/NHS (at 0.1 and 0.3 mg/ml) to wells containing Amine-PEG-Biotin. The reaction solution was allowed to incubate for 15 minutes in order to facilitate the functionalization of the exterior of the bacteria within the well with the biotin species. To each reaction well, streptavidin-europium (Eu-SAv) (PerkinElmer) was added at 400 ng/well. The reaction solution was allowed to incubate for 15 minutes in order to facilitate the coupling between the biotin and streptavidin. Then, the test plate was centrifuged, using a Thermo Scientific Heraeus Multifuge X3, at a speed of 2500×g for 2.5 minutes in order to pellet the bacteria in the bottom of the plate while leaving any unassociated reporter in the supernatant. The plate was then aspirated, using a BioTek Multiflo X plate washer, to remove the supernatant and unreacted reporter, before the addition of wash buffer. This wash procedure was repeated twice to investigate the effect of multiple washes on overall data quality. Wells containing Eu-SAv were reconstituted in reading buffer and read using time resolved fluorescence on a BioTek H1 plate reader, as shown in FIG. 37.

These data show that Europium formulations can be non-specifically bound to bacteria using a two-step process comprising NH2-PEG-Biotin followed by Eu-SAv.

Example 19

A Two-Step Bacteria Tagging Process with NHS-LC-LC-Biotin Followed by Eu-SAv can Non-Specifically Label Bacteria In this example, Europium formulations are non-specifically bound to bacteria using another two-step process.

Figure 38:
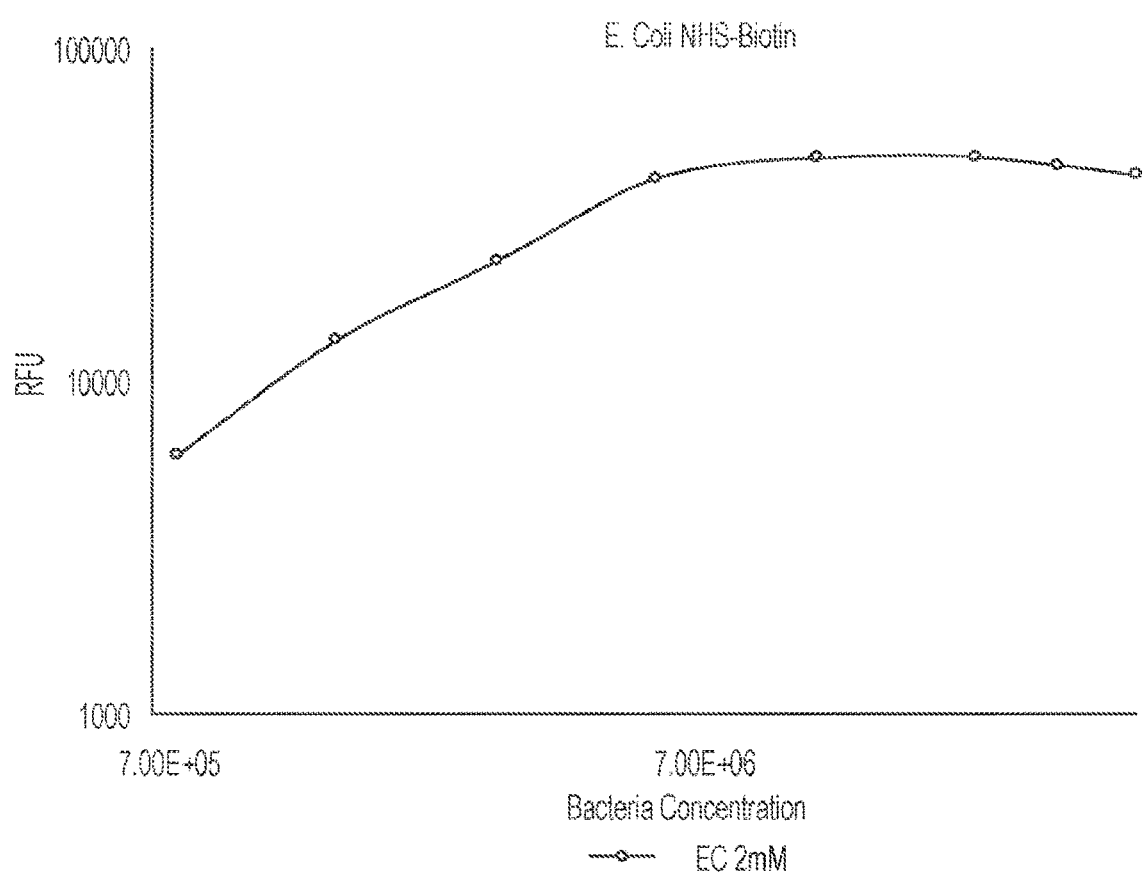
FIG. 38 is a graph showing the RFU obtained for specific bacterial concentrations of *E. coli* for a Europium formulation that is non-specifically bound to bacterial surfaces using a two-step process comprising NHS-LC-LC-Biotin followed by Eu-SAv.

*E coli* was inoculated across a 96-well plate in concentrations ranging from $1\times10^5$ to $1\times10^9$ in MES buffer at pH 6. To each well containing the bacteria, and the corresponding control wells, Amine-LC-LC-Biotin (Thermo-Fisher) was added at 1mg/well, then EDC/NHS (at 0.1 and 0.3 mg/ml) to wells containing Amine-PEG-Biotin. The reaction solution was allowed to incubate for 15 minutes in order to facilitate the functionalization of the exterior of the bacteria within the well with the biotin species. To each reaction well, streptavidin-europium (Perkin-Elmer) was added at 400 ng/well. The reaction solution was allowed to incubate for 15 minutes in order to facilitate the coupling between the biotin and streptavidin. Then, the test plate was centrifuged, using a Thermo Scientific Heraeus Multifuge X3, at a speed of 2500×g for 2.5 minutes in order to pellet the bacteria in the bottom of the plate while leaving any unassociated reporter in the supernatant. The plate was then aspirated, using a BioTek Multiflo X plate washer, to remove the supernatant and unreacted reporter, before the addition of wash buffer. This wash procedure was repeated twice to investigate the effect of multiple washes on overall data quality. Wells containing EuropiumCryptate-diamine were reconstituted in reading buffer and read using time resolved fluorescence on a BioTek H1 plate reader, as shown in FIG. 38.

These data show that Europium formulations can be non-specifically bound to bacteria using a two-step process comprising NHS-LC-LC-Biotin followed by Eu-SAv.

Example 20

Filamentous Bacteria can be Isolated from a Solution Using a Filter System Having Pores Ranging in Size from >0.2 Microns to <10 Microns; Thereby Providing More Accurate Chemical Sensitivity Data This Example illustrates an embodiment using filtering to exclude bacteria that have undergone filamentous growth in response to antimicrobial treatment.

Gram negative rods in particular first undergo filamentous growth in response to sub-inhibitory concentrations of cell wall-acting antimicrobials (such as beta lactams). Although these will eventually be inhibited, metabolic "volume" approaches have significant difficultly in distinguishing antimicrobial resistant bacteria from bacteria that have undergone filamentous growth. When not considered, such filamentous growth improperly identifies a bacterium as more resistant than it really is. Difficulty in determining antimicrobial resistance using a "volume" approach is seen in FIG. 39.

Figure 40:
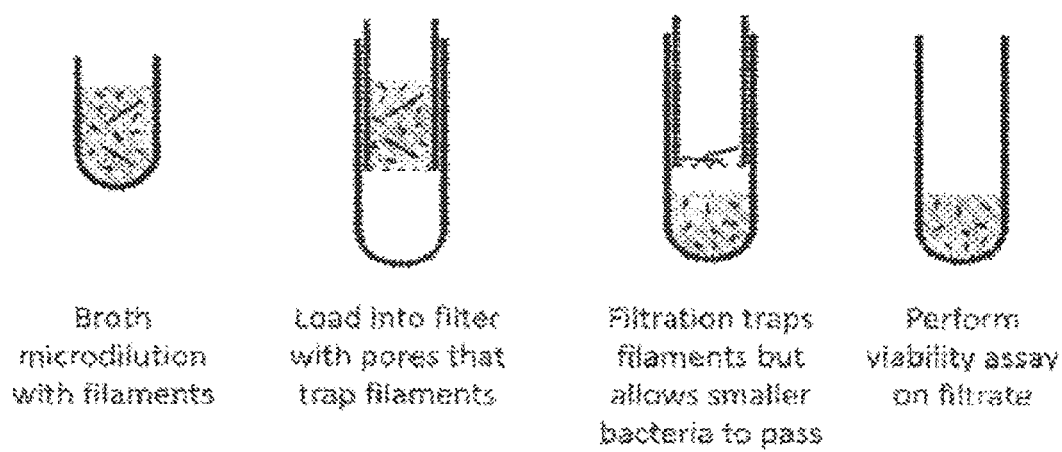
FIG. 40 is a schematic that illustrates a method for minimizing the interference of filamentous microorganisms in AST determinations.

In order to avoid this, in one embodiment, at the end of an incubation period, each broth microdilution is loaded into a filter comprising one or more pre-determined pore sizes (see FIG. 40). The pore sizes are chosen such that a plurality of "normal" bacteria is able to pass through the filter, but filamentous bacteria greater than a certain length are trapped. The pore size may be >0.2 microns and <10 microns.

This filter may be designed for parallel sample processing, such as a 96-, 384-, or 1586-well plate. A filter may be applied during the AST process, as shown in FIG. 40.

This example further illustrates the key advantage of designing a rapid AST platform that determines intact bacteria presence by surface area as opposed to the conventional metabolic approach, which is essentially a volumetric measurement.

Example 21

Methods for Preparing and Using a Signaling Agent Comprising a Fluorescent Nanoparticle In this example, methods for preparing and using a signaling agent comprising a fluorescent nanoparticle are described.

First, 20 mg of fluorescein dilaurate (FL-DL) were weighed into a clear glass scintillation vial and 1000 mg of Ethanol were added. The FL-DL was then dissolved in the vial via vortexing. Afterwards, 10 mg of DSPE-PEG-2k-amine (Laysan Bio) were added to this mixture and dissolved by vortexing. Separately, 40 g of DI water was weighed in a beaker, and a stir-bar was added. The beaker was then placed on a magnetic stirrer and stirred at 200 RPM. Next, the Ethanol solution was added to the beaker in a drop-wise fashion, and the subsequent solution was then introduced into a Microfluidics homogenizer and processed one time at 6000 psi. 200 gm of DI water was then added to the resulting mixture and Tangential Flow Filtration (TFF) was used to purify and concentrate the nanoparticles about 12-fold to 20 mL and were then collected in a glass scintillation vial. This collected nanoparticle formulation was filtered through a 0.2 µm filter, and nanoparticle size and concentration were determined by NanoSight (Malvern), with an average size reading of 102 nm.

The fluorophore-comprising nanoparticles were functionalized with positively charged small molecules to form a signaling agent useful in the present invention.

Both *Escherichia coli* (ATCC 11303) and ampicillin-resistant *E. coli* (ATCC 39936) were cultured under standard sterile conditions in LB broth at 37° C. Concentrations were determined by measuring absorbance at 600 nm (McFarland), and a concentration of $5 \times 10^5$ CFU/ml was set by dilution. Ampicillin was then weighed into sterile water and added in appropriate concentrations to sterile 3 mL microfuge tubes. Bacteria and nanoparticles at a concentration of $8 \times 10^8$ nanoparticles/ml were both added to these ampicillin-coated sterile microfuge tubes. The tubes were then capped and placed at 37° C. for 1.5 hours with continuous shaking, after which they were opened and each was passed through a 0.2 µm filter. Next, 100 µL of each filtrate was added to a well of a 96-well plate and 150 µL of a development solution (5% tetramethylammonium hydroxide in ethanol) was added to each well. After 5 minutes the plate was read at 490 nm excitation/530 nm emission in a SpectraMax M2 microplate reader (Molecular Devices).

Figure 41:
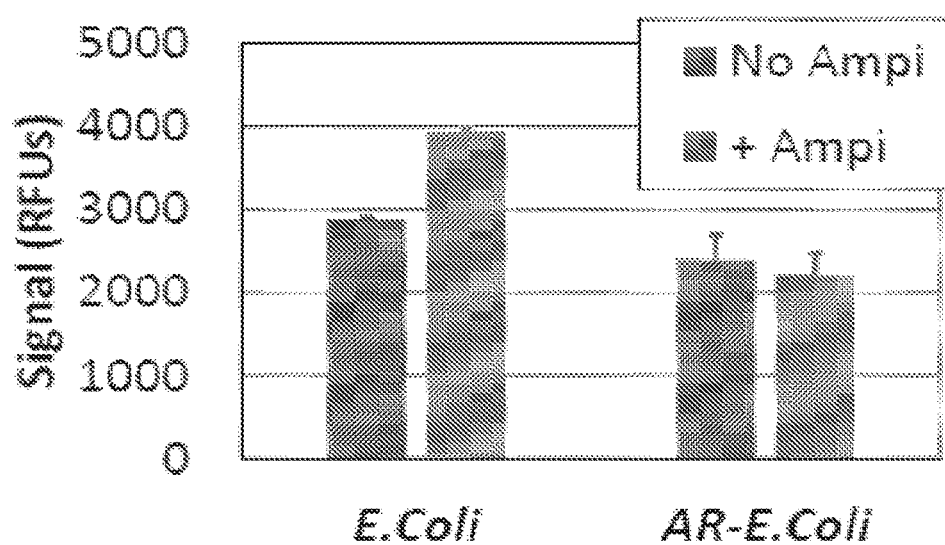
FIG. 41 is a graph showing the result of an assay using signaling agent comprising a fluorescent nanoparticle for *E. coli* and ampicillin-resistant *E. coli* treated with and without 100 µg/ml ampicillin (a concentration well above the MIC).

FIG. 41 shows the result of an assay using the above-prepared signaling agent comprising a nanoparticle. Here, *Escherichia coli* and ampicillin-resistant *E. coli* treated with and without 100 µg/ml ampicillin, a concentration well above the MIC. An assay for free signaling agents, which are not associated with intact bacteria, was performed after intact bacteria were removed by filtration through a 0.2 µm filter. Control groups containing no ampicillin show low fluorescent signals as does the ampicillin-resistant *E. coli* group treated with ampicillin. The *E. coli* treated with ampicillin above the MIC show a significant increase in fluorescence, indicating efficacy of this antimicrobial.

Figure 42:
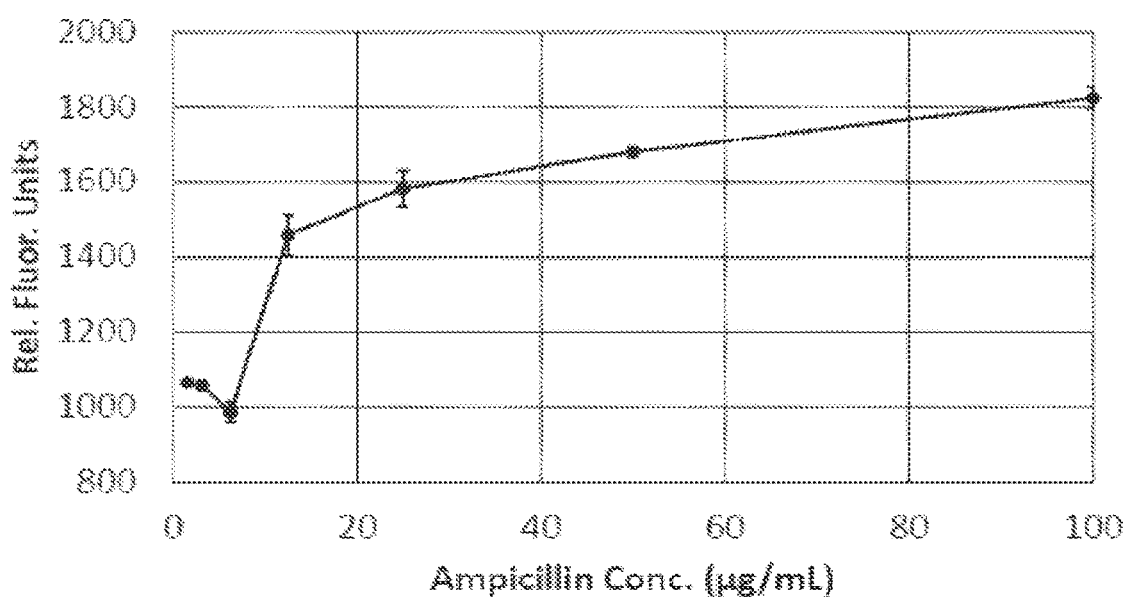
FIG. 42 is a graph showing the result of an assay using signaling agent comprising a fluorescent nanoparticle for *E. coli* and with varying ampicillin concentrations. Error bars shows the standard deviation of three replicates.

FIG. 42 shows the result of an assay for *E. coli* for varying ampicillin concentrations. The fluorescent signal is low when the ampicillin concentration is below the MIC, ~15 µg/ml, and it rises at this value, indicating the efficacy of the antimicrobial in this range

Example 22

The Present Invention can be Performed Using Magnetic Beads to Isolate Intact Bacteria In this example, magnetic beads, which are associated with an agent capable of binging intact bacteria, are used to isolate intact bacteria from a solution.

Magnetic beads reactive to *E. coli* were prepared from N-hydroxysuccinimidyl ester-activated 1 micron magnetic beads according to the manufacturer's instructions (ThermoFisher). Briefly, the supplied beads were magnetically captured and the storage solution was aspirated. The beads were then washed with ice-cold 0.1 M hydrochloric acid, followed by the addition of a polyclonal goal-anti-lipopolysaccharide (LPS) antibody (Antibodies-Online Inc.). The reaction was shaken for 2 hours, with vortexing every 5 minutes for the first 30 minutes, per the manufacturer's instructions. The beads were then washed thoroughly and stored in phosphate buffered saline, pH 7.4, at 4° C. until use.

Signaling agents comprise a moiety capable of binding to a microorganism (e.g., an antibody that binds to *E. coli*) and a chemical moiety capable of providing a signal or contributing to production of a signal (e.g., horseradish peroxidase (HRP)).

Figure 43:
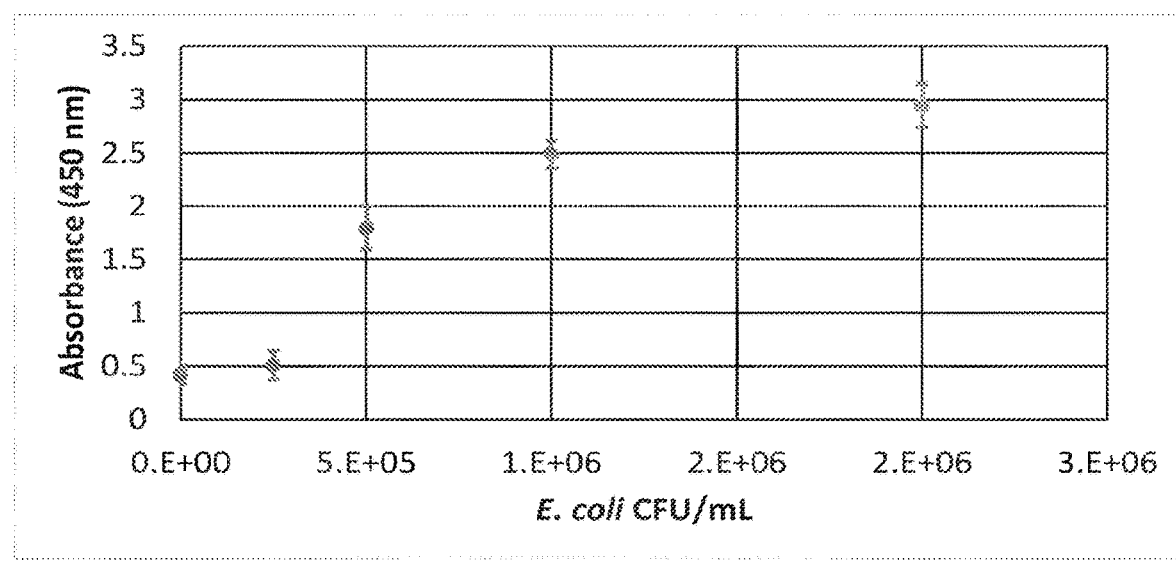
FIG. 43 is a graph showing the ability of *E. coli*-functionalized magnetic beads are capable of binding and isolating intact bacterium from a solution.

The anti-LPS magnetic beads and anti-*E. coli* signaling agents were added simultaneously to a McFarland standard-determined dilution series of *E. coli* in MH broth. The reaction was allowed to proceed for 20 min, followed by magnetic bead capture with a 96-well microplate magnetic stand (V&P Scientific). The wells were washed three times, followed by the addition of the detection solution described in Example 1. The optical densities at 450 nm and 650 nm were read for 10 min. The value at 5 min is plotted in FIG. 43.

The procedure of Example 1 was then used through the addition of signaling agents and functionalized magnetic beads. However, here, the *S. aureus* strain was ATCC 12600 and three antimicrobials were used: certazidime, oxacillin, and vancomycin.

Figure 44:
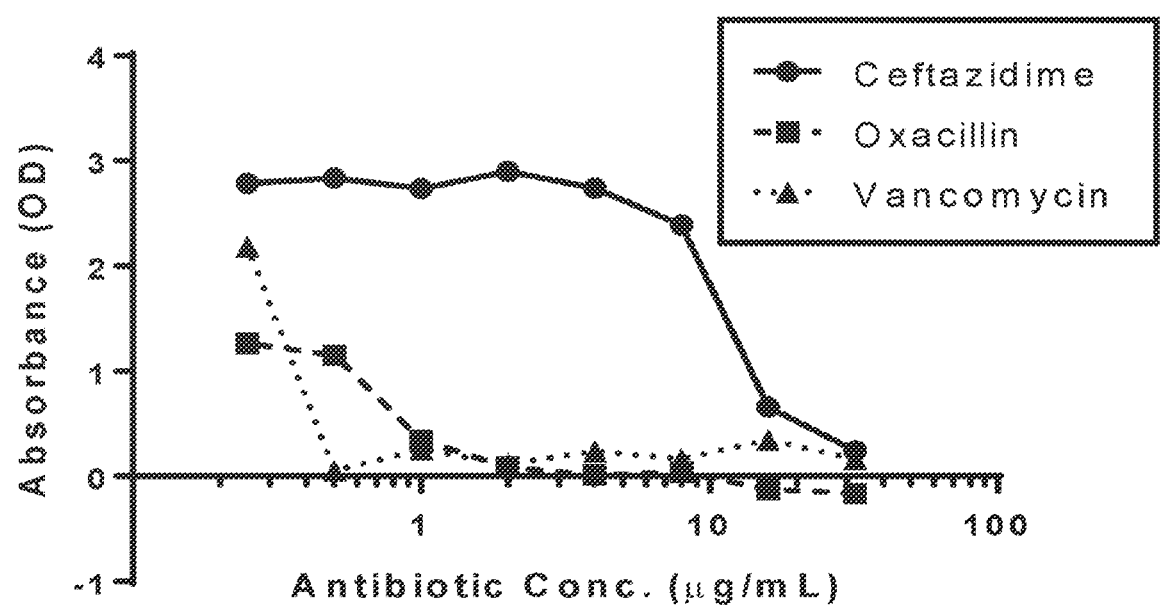
FIG. 44 is a graph showing the number of intact bacteria that are isolated by functionalized magnetic beads from solutions comprising varying amounts of an antimicrobial.

After the incubation period, magnetic beads with fixed cationic charges of 0.5 μm size (ChemiCell Fluidmag) were added concurrently with the signaling agents. The pH was adjusted to ~8.4 by the addition of 50 μL of borate buffer. The microplate was agitated on an orbital shaker for 20 minutes. The microplate was then placed on a magnetic capture plate comprising 24 neodymium N52 magnetics. The MH broth was then aspirated and PBS with 0.1% Tween-20 added for a total of three washes. After the final aspiration, a stabilized development solution consisting of 3,3',5,5'-tetramethylbenzidine (TMB) and hydrogen peroxide (ThermoFisher) was added, and the optical density at 650 nm and 450 nm were monitored for ten minutes with a microplate reader (Vmax, Molecular Devices). The data shown in FIG. 44 depicts from the five-minute point after the start of incubation with detection solution. As expected increasing amounts of the antimicrobials, which cause bacterial cell lysis, reduces the number of intact bacteria.

These data show that functionalized magnetic particles can capture intact bacteria and enable quantification of the intact bacteria (when bound to a signaling agent) following an antimicrobial treatment. Such magnetic capture may be used together with or in place of other separation techniques in order to collect intact bacteria for use in the present invention.

Example 23

Centrifugation of Bacterial Solutions Provides More Accurate Counts of Intact Bacteria when Compared to Isolation of Intact Bacteria by Functionalized Magnetic Beads In this example, the method for isolating intact bacteria using functionalized magnetic beads (as described in Example 21+) is compared to a method for isolating intact bacteria using centrifugation.

Capture of intact bacteria using functionalized magnetic beads was performed as described above. For the centrifugation data, bacteria were washed three times by a process of centrifugation at 2500×g for 2.5 minutes, manually aspiration, and addition of PBS-Tween. Magnetic beads were not used for centrifugation washes. Bacteria were treated with varying concentrations of vancomycin ("VAN").

Figure 45:
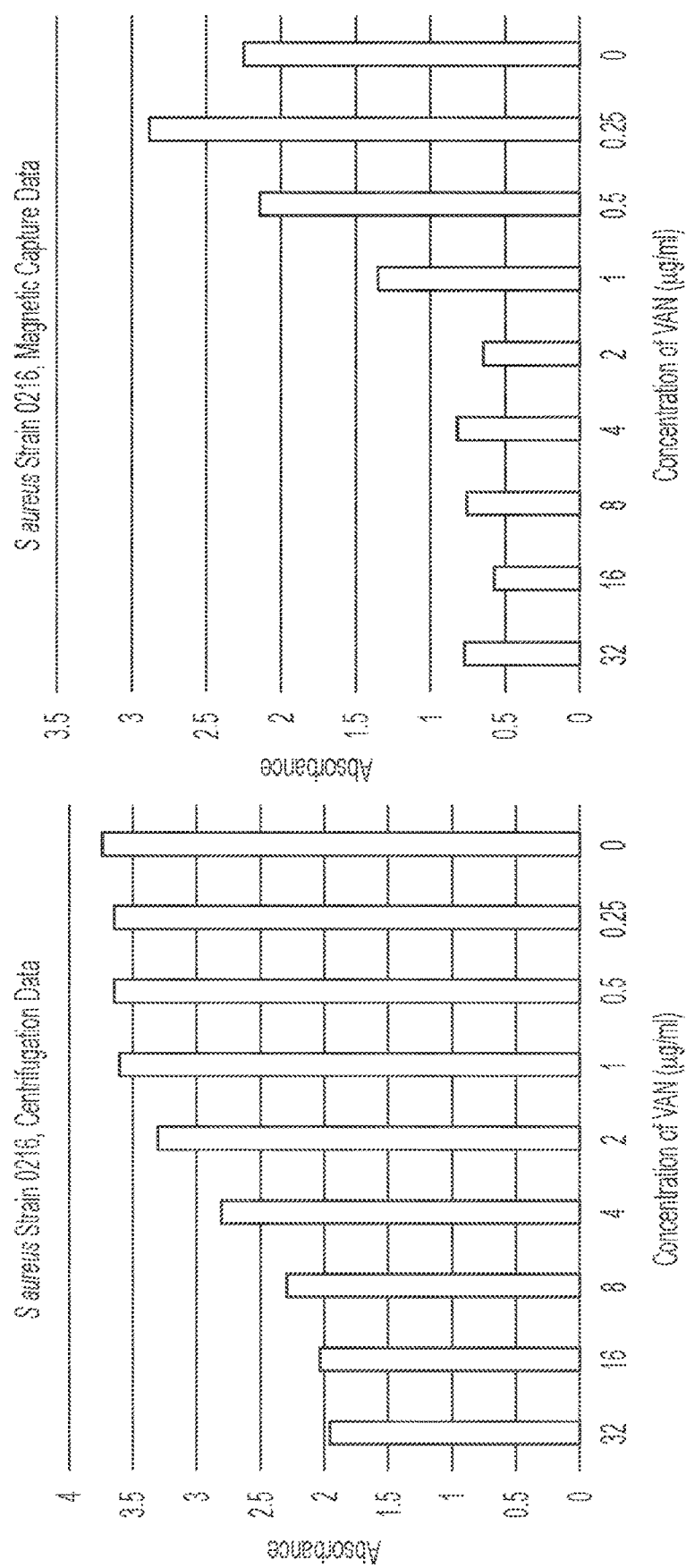
FIG. 45 includes graphs comparing the number of intact bacteria that are isolated by centrifugation versus functionalized magnetic beads from solutions comprising varying amounts of an antimicrobial (here, vancomycin "VAN"). The MIC for VAN for this clinical *S. aureus* strain was 8 µg/ml by CLSI overnight method.

FIG. 45 shows that centrifugation provides much higher and more accurate bacterial numbers and MICs than isolation by functionalized magnetic beads.

These data show that centrifugation of bacterial cultures for isolating intact bacteria is superior to methods using functionalized magnetic particles. Isolation using centrifugation may be used together with (e.g. magnetic isolation) or in place of other separation techniques in order to collect intact bacteria for use in the present invention.

Example 24

Chemical Amplification Via TAML Nanoparticle Amplifier Allows for Signaling with Optimal Sensitivity in the $1\times10^3$ to $1\times10^8$ CFU/Ml Range Using Standard Optical Detection Equipment In this example, methods for preparing and using a signaling agent comprising tetra-amino metalorganic ligand (TAML®) catalysts are described.

Figure 46A:
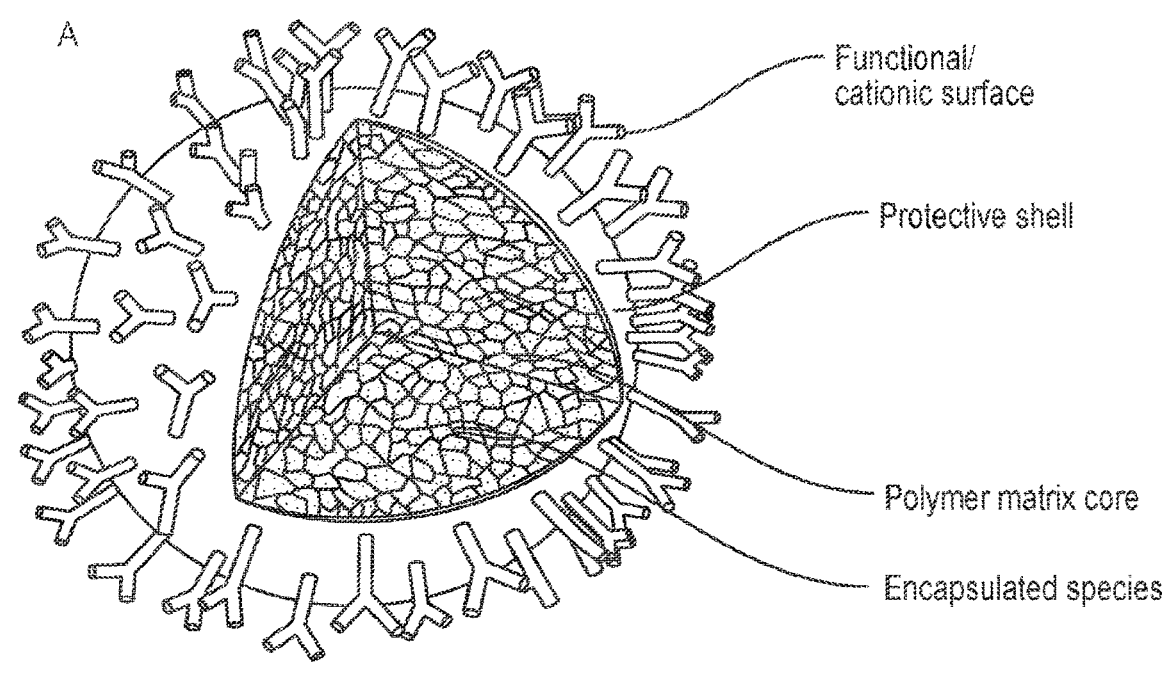
Figure 46B:
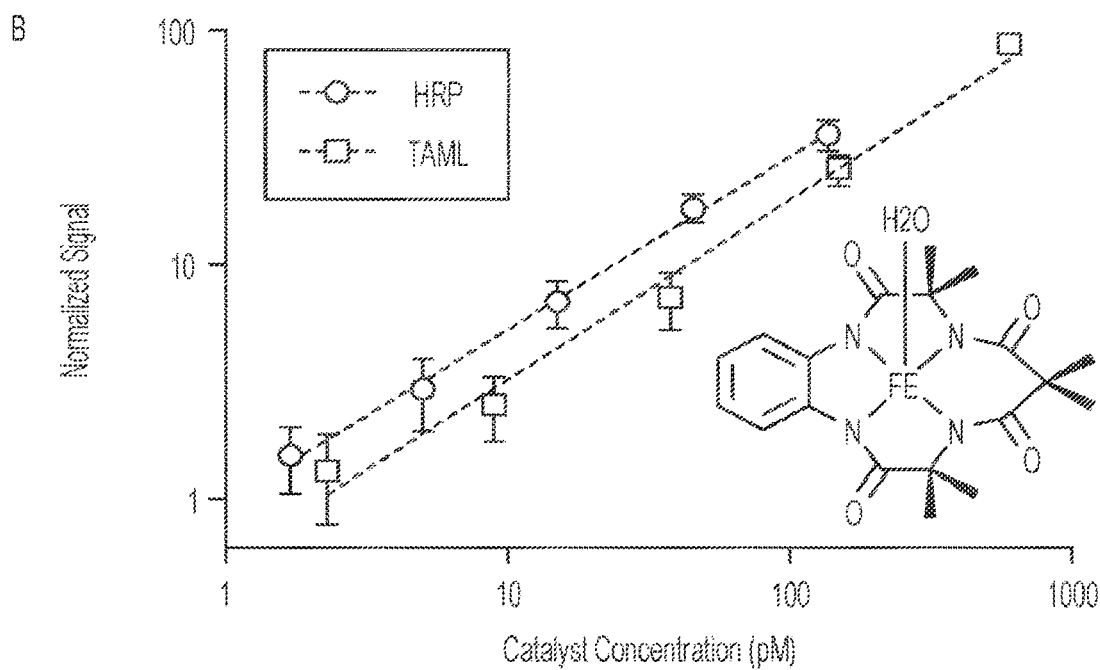
Figure 46C:
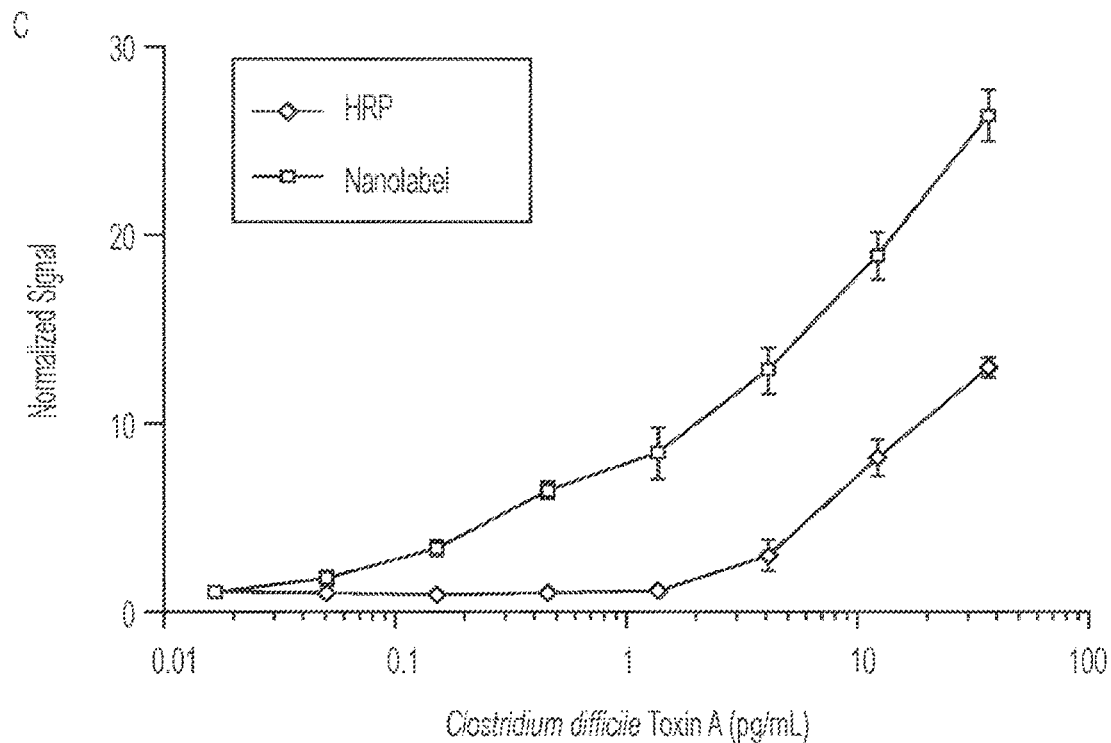

Chemical amplification in enabled with a proprietary nanoparticle amplifier, which adapts cutting-edge nanoparticle formulation techniques from drug delivery and a small-molecule catalyst from green chemistry. Each "nanolabel" comprises $>6\times10^4$ densely packed iron-containing, tetra-amino metalorganic ligand (TAML®) catalysts shielded by a polymer shell functionalized with specific ligands (FIG. 46). Each TAML molecule has molar activities within 5-fold those of horseradish peroxidase, a gold-standard immunoassay enzyme label (FIG. 46B). After specific binding, nanolabels are chemically triggered to release their contents into solution, enabling homogeneous catalysis of the optical signal. The high number of catalysts per binding event enables quantification of as few as 200 intact bacteria (FIG. 46A) and 100-fold sensitivity enhancements over standard enzyme immunoassays (FIG. 46C). In addition to obviating the need for the development of new detection technologies, standard optical detection enables compatibility with standard dried antimicrobial panel microplates, such as Sensi-Titre plates.

The invention claimed is:
1. A method for determining antimicrobial susceptibility of microorganisms comprising:
    (a) incubating a liquid suspension of microorganisms in the presence of an antimicrobial under conditions that promote growth of the microorganisms,
    (b) adding a signaling agent comprising a lanthanide signal amplifier and one or more chemical moieties that binds-non-specifically to a surface of the microorganisms;
    (c) separating the microorganisms bound by the signaling agent from unbound signaling agent; and
    (d) measuring an optical signal from the signaling agent bound to the surface of the microorganisms as compared to one or more controls, thereby measuring a relative surface area of the microorganisms.
2. The method of claim 1, wherein the one or more chemical moieties of the signaling agent is selected from the group consisting of:
    an antibody, lectin, natural peptide, synthetic peptides, bacteriophage, synthetic and/or natural ligands, synthetic and/or natural polymers, synthetic and/or natural glycopolymers, carbohydrate-binding proteins and/or polymers, glycoprotein-binding proteins and/or polymers, charged small molecules, other proteins, bacteriophages, and/or aptamers; and
    an amplifier group 104 that comprises a lanthanide coordination complex.
3. The method of claim 2, wherein the ligand and/or peptide is selected from the group consisting of bis(zinc-dipicolylamine), TAT peptide, serine proteases, cathelicidins, cationic dextrins, cationic cyclodextrins, salicylic acid, lysine, and combinations thereof.

4. The method of claim 1, wherein the antimicrobial susceptibility of the microorganisms is determined in less than 5 hours.

5. The method of claim 1, wherein adding the signaling agent occurs after the incubating step.

6. The method of claim 1, wherein the signaling agent forms a non-covalent interaction with the surface of a microorganism, wherein the non-covalent interaction comprises ionic interactions, van der Waals interactions, hydrophobic interactions, n-n interactions, or hydrogen bonding, or any combination thereof.

7. The method of claim 1, wherein multiple antimicrobials are tested in parallel.

8. The method of claim 1, wherein the determining signal levels comprises measuring the signal levels associated with intact microorganisms.

9. The method of claim 1, wherein the method further comprises a step of determining whether a microorganism is resistant, intermediately resistant or susceptible to one or more antimicrobials and/or determining one or more antimicrobial minimum inhibitory concentrations (MIC) based upon the signal levels associated with intact microorganisms.

10. The method of claim 1 wherein the microorganisms are bacteria, fungi, protozoa, or archaea.

11. The method of claim 1, wherein the microorganisms are obtained from a biological sample from a subject having an infection of the microorganisms and/or are obtained from a culture derived from the biological sample.

12. The method of claim 11, wherein the biological sample is selected from the group consisting of blood or blood components, bronchoalveolar lavage, cerebrospinal fluid, nasal swabs, sputum, stool, throat swabs, vaginal swabs, urine, aft6- or wound swabs, or a combination thereof.

13. The method of claim 1, wherein the one or more controls comprise a positive control measured from microorganisms under otherwise identical conditions but without antimicrobials or with one or more antimicrobials for which the microorganisms are not susceptible.

14. The method of claim 1, wherein the one or more controls comprise a control measured from microorganisms under otherwise identical conditions but without nutrients.

15. The method of claim 1, wherein the one or more controls comprise a control measured from microorganisms under otherwise identical conditions with one or more toxins known to inhibit growth of the microorganisms.

16. The method of claim 1, wherein the separating the microorganisms is performed by centrifugation, magnetic separation, filtration, electrophoresis, dielectrophoresis, precipitation, agglutination, or a combination thereof.

17. A method for determining antimicrobial susceptibility of microorganisms comprising:

(a) incubating, under conditions that promote growth of the microorganisms, a liquid suspension of microorganisms in a cartridge comprising a plurality of chambers defining dilution series for one or more antimicrobials;

(b) adding a signaling agent comprising a lanthanide signal amplifier and one or more chemical moieties to the plurality of chambers, wherein the signaling agent binds non-specifically to a surface of the microorganisms; and (c) measuring an optical signal from the signaling agent bound to the surf ace of the microorganisms in the plurality of chambers as compared to one or more controls, thereby determining the relative surface area of microorganisms.

18. The method of claim 17, wherein the antimicrobial susceptibility of the microorganisms is determined in less than 5 hours.

19. The method of claim 17, further comprising removing unbound signaling agent.

20. The method of claim 17, wherein the one or more controls comprise a positive control measured from microorganisms under otherwise identical conditions but without antimicrobials or with one or more antimicrobials for which the microorganisms are not susceptible.

21. The method of claim 17, wherein the signaling agent forms covalent bond with the surface of the microorganism in the presence of one or more agents that promote coupling, selected from the group consisting of glutaraldehyde, formaldehyde, paraformaldehyde, 1:ethyl-3-(3 dimethylaminopropyl)carbodiimide, N-(3-dimethylaminopropyl)-N'-ethylcarbonate, N,N'-dicyclohexylcarbodiimide, N-cyclohexyl-N'-(2-morpholinoethyl)carbodiimide-methyl-p-toluenesulfonate, diisopropylcarbodiimide, 1[bis(dimethylamino)methylene]-1H-1,2,3-triazolo[4,5-b]pyridinium 3-oxid hexafluorophosphate, Woodward's Reagent, N,N'-carbony 1 diimidazole, acrylates, amides, imides, anhydrides, chlorotriazines, epoxides, isocyanates, isothiocyanates, organic acids, monomers, polymers, silanes, silcates, NHS, sulfa-NHS, and a combination thereof.

22. The method of claim 17, wherein the microorganisms are obtained from a biological sample from a subject having an infection of the microorganisms and/or obtained from a culture derived from the biological sample; and wherein the biological sample is selected from the group consisting of blood or blood components, bronchoalveolar lavage, cerebrospinal fluid, nasal swabs, sputum, stool, throat swabs, vaginal swabs, urine, and wound swabs, or a combination thereof.

* * * * *